United States Patent
Kenmoku et al.

(10) Patent No.: US 7,425,432 B2
(45) Date of Patent: Sep. 16, 2008

(54) POLYHYDROXY ALKANOATE COPOLYMER INCLUDING WITHIN MOLECULE UNIT HAVING VINYL GROUP OR CARBOXYL GROUP IN SIDE CHAIN, AND PRODUCING METHOD THEREFOR

(75) Inventors: Takashi Kenmoku, Fujisawa (JP); Tetsuya Yano, Atsugi (JP); Chieko Mihara, Isehara (JP); Shinya Kozaki, Tokyo (JP); Tsutomu Honma, Atsugi (JP); Tatsuki Fukui, Yokohama (JP); Takeshi Imamura, Chigasaki (JP); Etsuko Sugawa, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 364 days.

(21) Appl. No.: 10/531,689

(22) PCT Filed: Oct. 23, 2003

(86) PCT No.: PCT/JP03/13531
§ 371 (c)(1),
(2), (4) Date: Apr. 15, 2005

(87) PCT Pub. No.: WO2004/044213
PCT Pub. Date: May 27, 2004

(65) Prior Publication Data
US 2006/0211100 A1    Sep. 21, 2006

(30) Foreign Application Priority Data
Oct. 24, 2002  (JP)  ............................. 2002-310250
Oct. 16, 2003  (JP)  ............................. 2003-356748

(51) Int. Cl.
 C12P 11/00  (2006.01)
 C12P 7/72   (2006.01)
 C08G 63/00  (2006.01)
 C08G 63/02  (2006.01)
 C08G 63/68  (2006.01)

(52) U.S. Cl. ................. 435/130; 435/135; 528/271; 528/272; 528/274; 528/293; 528/295

(58) Field of Classification Search .............. 528/271, 528/272, 293; 435/130, 135, 295, 303, 304; 529/295
See application file for complete search history.

(56) References Cited

U.S. PATENT DOCUMENTS 5,614,576 A    3/1997    Rutherford et al. .......... 524/270

(Continued)

FOREIGN PATENT DOCUMENTS

EP    1 113 033 A2    7/2001

(Continued)

OTHER PUBLICATIONS

Katharina Fritzsche et al., "An Unusual Bacterial Polyester with a Phenyl Pendant Group," 191 *Macromol. Chem.* 1957-65 (1990).

(Continued)

*Primary Examiner*—Herbert J Lilling
(74) *Attorney, Agent, or Firm*—Fitzpatrick, Cella, Harper & Scinto

(57) ABSTRACT

The invention provides a PHA copolymer including at least a 3-hydroxy-ω-carboxyalkanoic acid represented by a formula (19) or (32) and simultaneously at least a unit represented by a formula (2) or a formula (3) in a molecule, a precursor PHA copolymer having a corresponding vinyl group or a corresponding alkoxycarbonyl group, a biosynthesis method thereof by microorganisms, and a method of producing a desired PHA copolymer from the precursor PHA copolymer: (wherein k, m, n are integers; $R_{18}$ represents H, Na, K, $R_{27}$? represents (A); $R_1$ represents a substituent on a cyclohexyl group and represents H, CN, $NO_2$, a halogen atom, $CH_3$, $C_2H_5$, $C_3H_7$, $CF_3$, $C_2F_5$, or $C_3F_7$; R includes a residue including a phenyl structure or a thienyl structure; these being independent for each unit).

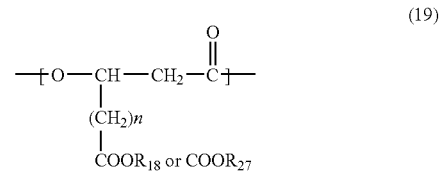

n = 1–8

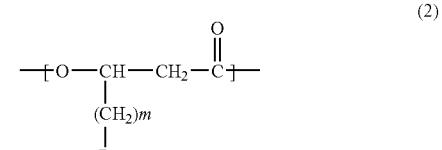

m = 1–8

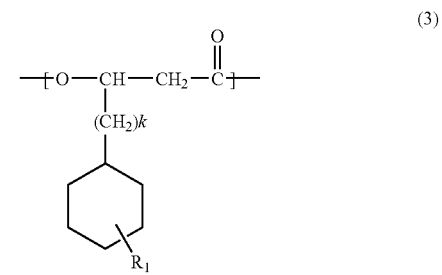

k = 0–8

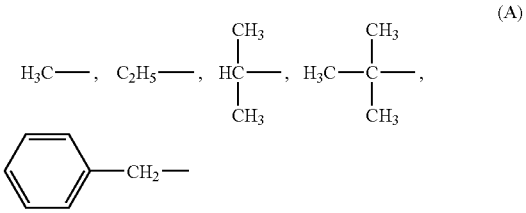

3 Claims, 6 Drawing Sheets

U.S. PATENT DOCUMENTS

| | | | | |
|---|---|---|---|---|
| 5,753,364 | A | 5/1998 | Rutherford et al. | 428/355 R |
| 6,492,147 | B2 | 12/2002 | Imamura et al. | 435/135 |
| 6,521,429 | B2 | 2/2003 | Honma et al. | 435/135 |
| 6,586,562 | B2 | 7/2003 | Honma et al. | 528/361 |
| 6,635,782 | B2 | 10/2003 | Honma et al. | 560/53 |
| 6,645,743 | B1 | 11/2003 | Honma et al. | 435/146 |
| 6,649,380 | B1 | 11/2003 | Yano et al. | 435/135 |
| 6,649,381 | B1 | 11/2003 | Honma et al. | 435/135 |
| 6,777,153 | B2 * | 8/2004 | Yano et al. | 430/110.1 |
| 6,808,854 | B2 * | 10/2004 | Imamura et al. | 430/110.1 |
| 6,869,782 | B2 * | 3/2005 | Kenmoku et al. | 435/130 |
| 6,872,788 | B2 | 3/2005 | Imamura et al. | 525/440 |
| 6,911,521 | B2 | 6/2005 | Kenmoku et al. | 528/295 |
| 7,045,321 | B2 * | 5/2006 | Imamura et al. | 528/272 |
| 2002/0022253 | A1 | 2/2002 | Honma et al. | 435/135 |
| 2002/0052444 | A1 | 5/2002 | Imamura et al. | 525/107 |
| 2002/0081646 | A1 | 6/2002 | Honma et al. | 435/41 |
| 2002/0160467 | A1 | 10/2002 | Honma et al. | 435/135 |
| 2002/0164726 | A1 | 11/2002 | Kenmoku et al. | 435/118 |
| 2003/0013841 | A1 | 1/2003 | Imamura et al. | 528/271 |
| 2003/0073804 | A1 * | 4/2003 | Imamura et al. | 528/274 |
| 2003/0096182 | A1 | 5/2003 | Yano et al. | 430/108.5 |
| 2003/0100084 | A1 | 5/2003 | Honma et al. | 435/135 |
| 2003/0100700 | A1 * | 5/2003 | Imamura et al. | 528/272 |
| 2003/0113368 | A1 | 6/2003 | Nomoto et al. | 424/450 |
| 2003/0180899 | A1 | 9/2003 | Honma et al. | 435/135 |
| 2003/0194789 | A1 | 10/2003 | Honma et al. | 435/135 |
| 2003/0207412 | A1 | 11/2003 | Kenmoku et al. | 435/135 |
| 2003/0208029 | A1 | 11/2003 | Honma et al. | 528/272 |
| 2004/0067576 | A1 | 4/2004 | Honma et al. | 435/252.34 |
| 2004/0092702 | A1 | 5/2004 | Honma et al. | 528/272 |
| 2005/0143574 | A1 | 6/2005 | Minami et al. | 536/126 |
| 2006/0040366 | A1 | 2/2006 | Kenmoku et al. | 435/135 |
| 2006/0079662 | A1 | 4/2006 | Fukui et al. | 528/272 |

FOREIGN PATENT DOCUMENTS

| | | |
|---|---|---|
| EP | 1 130 042 A2 | 9/2001 |
| EP | 1 188 782 A2 | 3/2002 |
| EP | 1 888 836 A2 | 3/2002 |
| EP | 1 201 763 A2 | 5/2002 |
| EP | 1 236 754 A2 | 9/2002 |
| EP | 1 236 755 A2 | 9/2002 |
| EP | 1 245 605 A2 | 10/2002 |
| JP | 59-190945 | 10/1984 |
| JP | 2989175 B1 | 10/1999 |
| JP | 2002-80571 | 3/2002 |
| WO | WO 2004/037889 A1 | 5/2004 |
| WO | WO 2004/097417 A1 | 11/2004 |

OTHER PUBLICATIONS

Y.B. Kim et al., "Preparation and Characterization of Poly(β-Hydroxyalkanoates) Obtained from *Pseudomonas oleovorans* with Mixtures of 5-Phenylvaleric Acid and *n*-Alkanoic Acids," 24 *Macromol.* 5256-60 (1991).

Suzette M. Aróstegui et al., "Bacterial Polyesters Produced by *Pseudomonas oleovorans* Containing Nitrophenyl Groups," *Macromol.* 2889-95 (1999).

Helmut Ritter et al., "Bacterial Production of Polyesters Bearing Phenoxy Groups in Side Chains, 1 Poly(3-Hydroxy-5-Phenoxypentanoate- *co*-3-Hydroxy-9-Phenoxy-Nonanoate) From *Pseudomonas oleovorans*," 195 *Macromol. Chem. Phys.* 1665-72 (1994).

Richard A. Gross et al., "Cyanophenoxy-Containing Microbal Polyesters: Structural Analysis, Thermal Properties, Second Harmonic Generation and In-Vivo Biodegradability," 39 *Polymer International* 205-13 (1996).

Won Ho Park et al., "Epoxidation of Bacterial Polyesters with Unsaturated Side Chains. I. Production and Epoxidation of Polyesters from 10-Undecanoic Acid," 31 *Macromol.* 1480-1486 (1998).

Ohyoung Kim et al., "Bioengineering of Poly(β-hydroxyalkanoates) for Advanced Material Applications: Incorporation of Cyano and Nitrophenoxy Side Chain Substituents," 41 (Supp. 1) *Can. J. Microbiol.* 32-43 (1995).

Young B. Kim et al., "Poly(β-hydroxyalkanoate) Copolymers Containing Brominated Repeating Units Produced by *Pseudomonas oleovorans*," 25 *Macromol.* 1852-57 (1992).

Marieta Constantin et al., "Chemical Modification of Poly(hydroxyalkanoates). Copolymers Bearing Pendant Sugars," 20 *Macromol. Rapid Commun.* 91-94 (1999).

M.Y. Lee et al., "Hydrophilic Bacterial Polyesters Modified with Pendant Hydroxyl Groups," 41 *Polymer* 1703-09 (2000).

J. K. Stille et al., "Tetracyclic Dienes. I. The Diels-Alder Adduct of Norbornadiene and Cyclopentadiene," 81 *J. Am. Chem. Soc.* 4273-75 (Aug. 1959).

G.J.M. de Koning et al., "A Biodegradable Rubber by Crosslinking Poly(hydroxyalkanoate) From *Pseudomonas oleovorans*," 35 (10) *Polymer* 2090-97 (1994).

Lindsay H. Briggs et al., "Degradation of the Lanosterol Side-chain," *J.C.S. Perkin I*, 806-09 (1973).

Harry R. Allcock et al., "Reactions of Steroid Salts with Hexachlorocyclotriphosphazene," 46 *J. Org. Chem.* 13-22 (1981).

*Organic Synthesis*, vol. 4, pp. 695-699 (1963).

Joanne M. Curley et al., "Production of Poly(3-hydroxyalkanoates) Containing Aromatic Substituents by *Pseudomonas oleovorans*," 29 *Macromol.* 1762-66 (1996).

Marie-Maud Bear et al., "Preparation of a Bacterial Polyester with Carboxy Groups in Side Chains," 4 *Chemistry* 289-93 (2001).

Young Baek Kim, "Preparation, Characterization, and Modification of Polyβ-hydroxyalkanoates from *Pseudomonas oleovorans*," Dissertation, University of Massachusetts (1991).

Alexander Steinbüchel et al., "Diversity of Bacterial Polyhydroxyalcanoic Acids," 128 *FEMS Microbiol. Lett.* 219-28 (1995).

Marianela Andújar et al., "Polyesters Produced by *Pseudomonal oleovorans* Containing Cyclohexyl Groups," 30 *Macromol.* 1611-15 (1997).

Carmen Scholz et al., "Growth and Polymer Incorporation of *Pseudomonas oleovorans* on Alkyl Esters of Heptanoic Acid," 27 *Macromol.* 2886-89 (1994).

Carmen Scholz et al., "Production of Poly(β-hydroxyalkanoates) with β-substituents Containing Terminal Ester Groups by *Pseudomonas oleovorans*," 195 *Macromol. Chem. Phys.* 1405-21 (1994).

* cited by examiner

POLYHYDROXY ALKANOATE COPOLYMER INCLUDING WITHIN MOLECULE UNIT HAVING VINYL GROUP OR CARBOXYL GROUP IN SIDE CHAIN, AND PRODUCING METHOD THEREFOR

TECHNICAL FIELD

The present invention relates to a polyhydroxy alkanoate (hereinafter also abbreviated as PHA) copolymer including a novel unit having a double bond and a producing method therefor utilizing microorganisms, also polyhydroxy alkanoate copolymer including a novel unit having a carboxyl group or a salt thereof, derived from the aforementioned copolymer, and a producing method therefor.

Also the present invention relates to a polyhydroxy alkanoate copolymer including a novel unit having an ester group and a producing method therefor utilizing microorganisms, also polyhydroxy alkanoate copolymer including a novel unit having a carboxyl group or a salt thereof, derived from the aforementioned copolymer, and a producing method therefor.

BACKGROUND ART

It has already been reported that various microorganisms produce poly-3-hydroxybutyric acid (PHB) or other poly-3-hydroxyalkanoate (PHA) and accumulate such products therein. Such PHA produced by the microorganisms can be utilized for producing various products. Also the PHA produced by microorganisms, being biodegradable, has the advantage that it can be completely decomposed by the microorganisms. Therefore the PHA produced by microorganisms, when discarded, unlike the various conventional synthesized polymers, would not cause pollution resulting from remaining in the natural environment. Also the PHA produced by microorganisms shows satisfactory affinity to the living tissues and is expected in the applications as the soft material for medical use.

However, for wider application of microorganism-produced PHA, for example for application as functional polymer, PHA having a substituent other than alkyl group in the side chain, namely "unusual PHA", is anticipated to be extremely useful. Examples of hopeful substituents for this purpose include a group containing an aromatic ring (phenyl group, phenoxy group etc.), an unsaturated hydrocarbon group, an ester group, an allyl group, a cyano group, a halogenated hydrocarbon group and an epoxide present on the side chain. Among these, PHA having an aromatic ring is actively investigated as follows:

(a) PHA containing a phenyl group or a partially substituted group thereof:

Makromol. Chem. 191, 1957-1965(1990) and Macromolecules, 24, 5256-5260(1991) report that *Pseudomonas oleovorans* produces PHA containing 3-hydroxy-5-phenylvaleric acid as a unit, from 5-phenylvaleric acid as a substrate.

Macromolecules, 29, 1762-1766(1996) reports that *Pseudomonas oleovorans* produces PHA containing 3-hydroxy-5-(p-tolyl)valeric acid as a unit, from 5-(p-tolyl)valeric acid as a substrate.

Macromolecules, 32, 2889-2895(1999) reports that *Pseudomonas oleovorans* produces PHA containing 3-hydroxy-5-(2,4-dinitrophenyl)valeric acid and 3-hydroxy-5-(p-nitrophenyl)valeric acid as units, from 5-(2,4-dinitrophenyl)valeric acid as a substrate.

(b) PHA containing phenoxy group or a partially substituted group thereof:

Macromol. Chem. Phys., 195, 1665-1672(1994) reports that *Pseudomonas oleovorans* produces a PHA copolymer containing 3-hydroxy-5-hydroxyvaleric acid and 3-hydroxy-9-phenoxynonanoic acid as the units, from 11-phenoxyundecanoic acid as a substrate.

Also Japanese Patent No. 2989175 discloses inventions relating to a homopolymer constituted of a 3-hydroxy-5-(monofluorophenoxy) pentanoate (3H5(MFP)P) unit or a 3-hydroxy-5-(difluorophenoxy) pentanoate (3H5(DFP)P) unit, a copolymer containing either a 3H5(MFP)P unit or a 3H5(DFP)P unit or both, a novel strain of *Pseudomonas putida* capable of producing these polymers, and a method for producing the aforementioned polymers utilizing bacteria of genus *Pseudomonas*. This patent specification teaches, as the effects of such inventions, that PHA polymer having a phenoxy group substituted with 1 or 2 fluorine atoms at the end of the side chain can be biosynthesized from a long-chain fatty acid having a fluorine substituent and that thus produced PHA has a high melting point and is capable of providing stereoregularity and water repellency while maintaining satisfactory working properties.

In addition to the fluorine-substituted PHA having a fluorine substitution on the aromatic ring in the unit, there are also investigated PHA having a cyano group or a nitro group on the aromatic ring in the unit.

Can. J. Microbiol., 41, 32-43(1995) and Polymer International, 39, 205-213(1996) report production of PHA, containing 3-hydroxy-6-(p-cyanophenoxy) hexanoic acid or 3-hydroxy-6-(p-nitrophenoxy) hexanoic acid as the monomer unit, by *Pseudomonas oleovorans* ATCC 29347 strain and *Pseudomonas putida* KT2442 strain, from octanoic acid and 6-(p-cyanophenoxy) hexanoic acid or 6-(p-nitrophenoxy) hexanoic acid as a substrate.

These references relate to PHA having an aromatic ring on the side chain, instead of alkyl groups of the usual PHA, which are effective in obtaining polymer with physical properties resulting from such aromatic ring.

Also as a new category not limited to changes in the physical properties, investigations are also made for producing PHA having an appropriate functional group on the side chain, thereby obtaining PHA with new functions utilizing such substituent.

As a specific method for such purpose, investigations are also made for producing PHA having, in a unit thereof, reactive group such as a bromo group or a vinyl group with a high activity for example in an addition reaction to introduce an arbitrary function group in a side chain of the polymer by a chemical conversion utilizing such active group, in order to obtain PHA of multiple functions.

Macromol. Rapid Commun., 20, 91-94(1999) reports production of PHA having a bromo group in a side chain by *Pseudomonas oleovorans*, and modifying the side chain with a thiolated product of acetylated maltose thereby synthesizing PHA different in solubility and hydrophilicity.

Polymer, 41, 1703-1709(2000) reports producing PHA, having 3-hydroxyalkenic acid with an unsaturated bond (vinyl group) at an end of a side chain as a monomer unit, by *Pseudomonas oleovorans* with 10-undecenoic acid as a substrate, followed by an oxidation reaction with potassium permanganate to synthesize 3-hydroxyalkanoic acid having a diol at the end of the side chain, which PHA is reported to show such a change in solubility in solvents, as becoming soluble in polar solvents such as methanol, an acetone-water (80/20, v/v) or dimethylsulfoxide and insoluble in non-polar solvents such as chloroform, tetrahydrofuran or acetone.

Also Macromolecules, 31, 1480-1486(1996) reports production of a polyester, including a unit having vinyl group in a side chain by *Pseudomonas oleovorans* and epoxylating the vinyl group to obtain a polyester having an epoxy group in the side chain.

Also Polymer, 35, 2090-2097(1994) reports a crosslinking reaction within the polyester molecule utilizing the vinyl group in the side chain of polyester, thereby improving physical properties of polyester.

Macromolecular chemistry, 4, 289-293(2001) reports producing PHA, including 3-hydroxy-10-undecenoic acid as a monomer unit, from 10-undecenoic acid as a substrate, and then executing an oxidation reaction with potassium permanganate to obtain PHA including 3-hydroxy-10-carboxydecanoic acid as a monomer unit, and reports an improvement in a decomposition thereof.

Furthermore, in order to modify physical properties of PHA having an active group in a unit and to actually utilize it as a polymer, it has been studied biosynthesis of a PHA copolymer including a unit having the active group and other units; Macromolecules, 25, 1852-1857(1992) reports production of a PHA copolymer including a 3-hydroxy-ω-bromoalkanoic acid unit and a linear alkanoic acid unit by *Pseudomonas oleovorans* in the presence of an ω-bromoalkanoic acid such as 11-bromoundecanoic acid, 8-bromooctanoic acid or 6-bromohexanoic acid and n-nonanoic acid.

Such PHA having a highly reactive active group such as a bromo group or a vinyl group can be subjected to introduction of various functional groups or chemical modification, and such a group can be a crosslinking point for a polymer, so that it is very useful means for realizing multiple functions in PHA.

Also technologies related to the present invention include a technology of oxidizing a carbon-carbon double bond with an oxidant to obtain a carboxylic acid (Japanese Patent Application Laid-Open No. S59-190945, J. Chem. Soc., Perkin. Trans. 1, 806(1973), Org. Synth., 4, 698(1963), J. Org. Chem., 46, 19(1981), and J. Am. Chem. Soc., 81, 4273(1959).

On the other hand, active investigations are being made for obtaining a multi-functional PHA from PHA including an ester group in a unit.

Macromol. Chem. Phys., 195, 1405-1421(1994) reports production of a polyhydroxy alkanoate including a unit having an ester group in a side chain, employing *Pseudomonas oleovorans* as a production microorganism and an alkanoate ester.

Also University of Massachusetts Ph. D. Dissertation Order Number 9132875 (1991) reports production of a polyhydroxy alkanoate including a unit having a benzylester structure, also employing *Pseudomonas oleovorans* as a production microorganism.

However, the copolymers in the foregoing reports are comprised of a monomer unit having a carboxyl group or an ester group at the end of a side chain and a monomer unit having a linear alkyl group (usual PHA) having a low glass transition temperature. On the other hand, there is no report on copolymers including unusual PHA having on the side chain thereof a substituent other than a linear alkyl group, such as a phenyl structure, a thienyl structure or a cyclohexyl structure. Thus, such polyhydroxy alkanoate and a producing method therefor have been required.

Also PHA having a vinyl group as an active group is a PHA copolymer with a monomer unit having a linear alkyl group (usual PHA), its low glass transition temperature and low melting point are undesirable properties in the working and the use of the polymer.

Because of the above-described situation, there have been a demand for PHA having an active group and a production method therefor, such that PHA can be produced by a microorganism at a high yield, the unit ratio of the active group can be controlled, and its physical properties can be freely regulated not to limit its application as a polymer.

DISCLOSURE OF THE INVENTION

As a result of intensive investigations, the present inventors have found a method of synthesizing a PHA formed by copolymerization of a unit having a vinyl group, an ester group or a carboxyl group of a high reactivity, and a unit having either one of a phenyl structure, a thienyl structure and a cyclohexyl structure which can contribute to an improvement of physical properties of the polymer, and have thus made the present invention.

The present invention is outlined in the following.

[1] A polyhydroxy alkanoate copolymer including at least a 3-hydroxy-ω-alkenoic acid unit represented by a chemical formula (1) in a molecule, and simultaneously at least a 3-hydroxy-ω-alkanoic acid unit represented by a chemical formula (2) or a 3-hydroxy-ω-cyclohexylalkanoic acid unit represented by a chemical formula (3) in the molecule:

[Chemical Formula (1)]

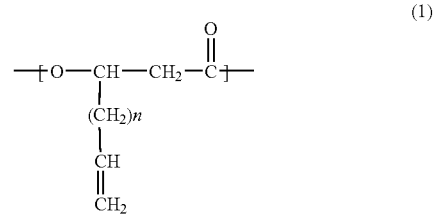

n = 1–8 in which n represents an integer selected within a range indicated in the chemical formula; and in case plural units are present, n is the same or different for each unit;

[Chemical Formula (2)]

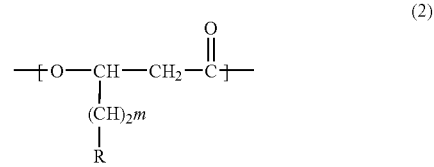

m = 1–8 in which m represents an integer selected within a range indicated in the chemical formula; R represents a residue having any of a phenyl structure or a thienyl structure; and in case plural units are present, m and R are the same or different for each unit;

[Chemical Formula (3)]

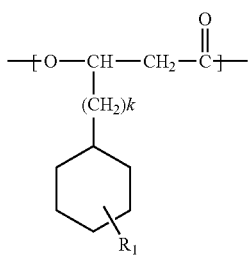

(3)

k = 0–8 in which $R_1$ being a substituent on a cyclohexyl group represents a hydrogen atom, a CN group, a $NO_2$ group, a halogen atom, a $CH_3$ group, a $C_2H_5$ group, a $C_3H_7$ group, a $CF_3$ group, a $C_2F_5$ group, or a $C_3F_7$ group; k represents an integer selected within a range indicated in the chemical formula; and in case plural units are present, $R_1$ and k may be the same or different for each unit.

[2] A polyhydroxy alkanoate copolymer including at least a 3-hydroxy-ω-carboxyalkanoic acid unit represented by a chemical formula (19) or 3-hydroxy-ω-alkoxycarbonylalkanoic acid unit represented by a chemical formula (32) in a molecule, and simultaneously at least a 3-hydroxy-ω-alkanoic acid unit represented by the chemical formula (2) or a 3-hydroxy-ω-cyclohexylalkanoic acid unit represented by the chemical formula (3) in the molecule,

[Chemical Formula (19)]

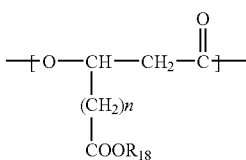

(19)

n = 1–8 in which n represents an integer selected within a range indicated in the chemical formula; $R_{18}$ represents an H atom, a Na atom or a K atom: and in case plural units are present, n and $R_{18}$ may be the same or different for each unit; and

[Chemical Formula (32)]

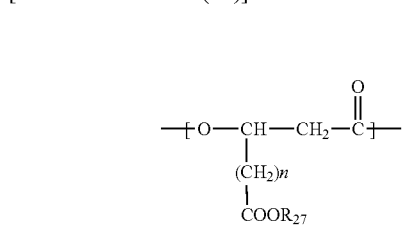

(32)

n = 1–8

$R_{27}$: 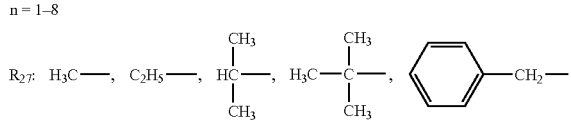

in which n represents an integer selected within a range indicated in the chemical formula; $R_{27}$ represents any of residues indicated in the chemical formula; and in case plural units are present, n and $R_{27}$ may be the same or different for each unit.

[3] A method for producing a polyhydroxy alkanoate copolymer including at least a 3-hydroxy-ω-alkenoic acid unit represented by the chemical formula (1) in a molecule, and simultaneously at least a 3-hydroxy-ω-alkanoic acid unit represented by a chemical formula (2) or a 3-hydroxy-ω-cyclohexylalkanoic acid unit represented by a chemical formula (3) in the molecule, characterized in including a biosynthesis by a production microorganism from at least an ω-alkenoic acid represented by a chemical formula (24) and at least a compound represented by a chemical formula (25) or at least an ω-cyclohexylalkanoic acid represented by a chemical formula (26) as starting materials:

[Chemical Formula (24)]

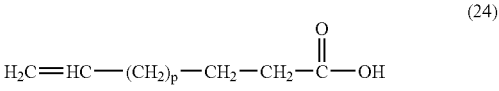

(24)

p = 1–8 in which p represents an integer selected within a range indicated in the chemical formula;

[Chemical Formula (25)]

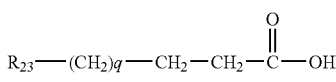

(25)

q = 1–8 in which q represents an integer selected within a range indicated in the chemical formula; and $R_{23}$ includes a residue having a phenyl structure or a thienyl structure;

[Chemical Formula (26)]

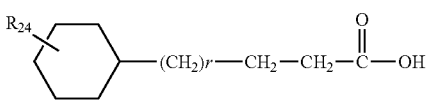

(26)

r = 0–8 in which $R_{24}$ represents a substituent on a cyclohexyl group and represents an H atom, a CN group, a $NO_2$ group, a halogen atom, a $CH_3$ group, a $C_2H_5$ group, a $C_3H_7$ group, a $CF_3$ group, a $C_2F_5$ group, or a $C_3F_7$ group; and r represents an integer selected within a range indicated in the chemical formula.

[4] A method for producing a polyhydroxy alkanoate copolymer including at least a 3-hydroxy-ω-carboxyalkanoic acid unit represented by the chemical formula (19) in a molecule, and simultaneously at least a 3-hydroxy-ω-alkanoic acid unit represented by the chemical formula (2) or a 3-hydroxy-ω-cyclohexylalkanoic acid unit represented by the chemical formula (3) in the molecule comprising the steps of:

preparing a polyhydroxy alkanoate copolymer including at least a 3-hydroxy-ω-alkenoic acid unit represented by the chemical formula (1) in a molecule, and simultaneously at least a 3-hydroxy-ω-alkanoic acid unit represented by the chemical formula (2) or a 3-hydroxy-ω-cyclohexylalkanoic acid unit represented by the chemical formula (3) in the molecule as a starting material, and oxidizing a double bond portion in the polyhydroxy alkanoate represented in the chemical formula (1) to generate the object polyhydroxy alkanoate copolymer.

[5] A method for producing a polyhydroxy alkanoate copolymer, characterized in employing a polyhydroxy alkanoate copolymer including at least a 3-hydroxy-ω-alkoxycarbonylalkanoic acid unit represented by a chemical formula (32) in a molecule, and simultaneously at least a 3-hydroxy-ω-alkanoic acid unit represented by the chemical formula (2) or a 3-hydroxy-ω-cyclohexylalkanoic acid unit represented by the chemical formula (3) in the molecule as a starting material, and executing a hydrolysis in the presence of an acid or an alkali or executing a hydrogenolysis including a catalytic reduction, thereby generating a polyhydroxy alkanoate copolymer including at least a 3-hydroxy-ω-carboxyalkanoic acid unit represented by the chemical formula (19) in a molecule, and simultaneously at least a 3-hydroxy-ω-alkanoic acid unit represented by the chemical formula (2) or a 3-hydroxy-ω-cyclohexylalkanoic acid unit represented by the chemical formula (3) in the molecule.

BEST MODE FOR CARRYING OUT THE INVENTION

Figure 1:
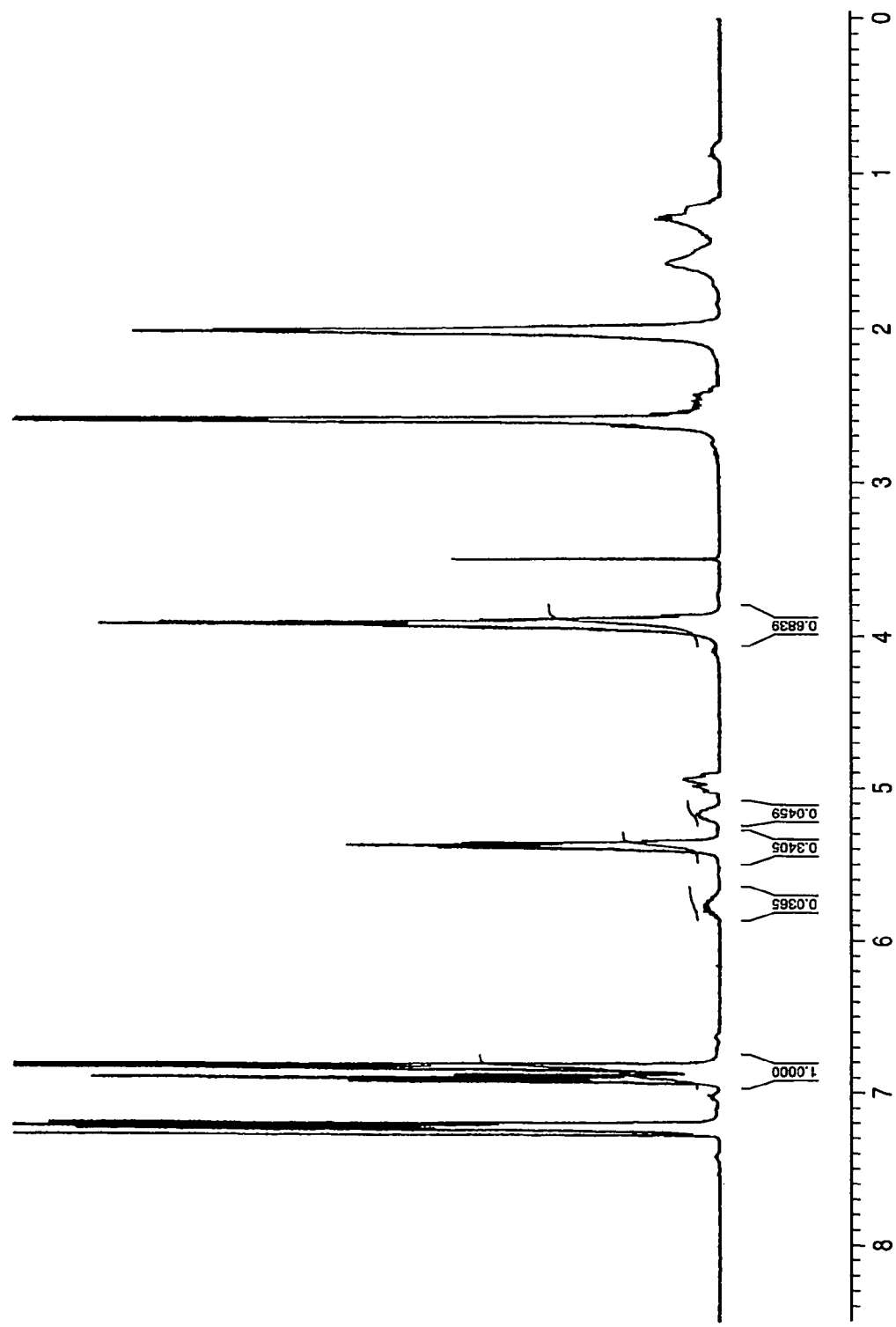
FIG. 1 is a $^1$H-NMR spectrum of a polyester obtained in Example 1.
Figure 2:
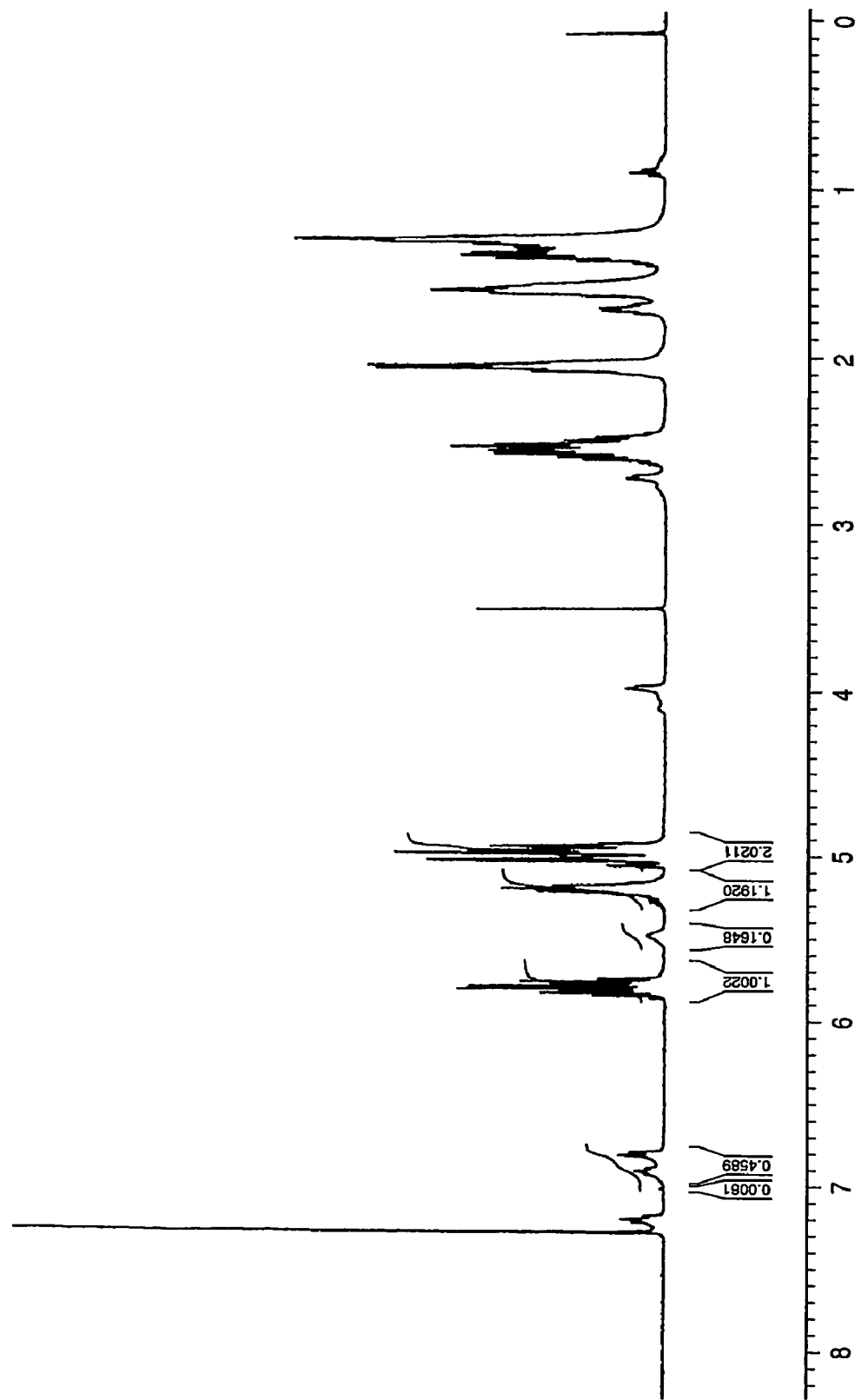
FIG. 2 is a $^1$H-NMR spectrum of a polyester obtained in Example 2.

A polyhydroxy alkanoate copolymer, the final product of the present invention, is a polyhydroxy alkanoate copolymer (hereinafter also called carboxyl PHA) comprising a unit having a carboxyl group on a side chain as represented by a chemical formula (19) and a unit represented by a chemical formula (2) or a chemical formula (3):

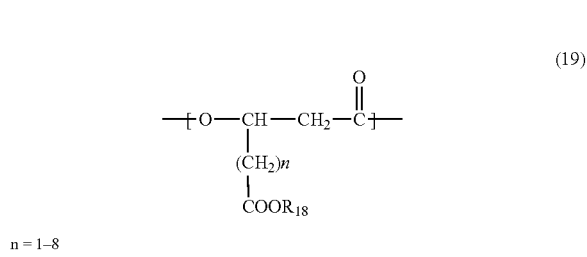

$n = 1-8$ in which n represents an integer selected within a range indicated in the chemical formula; $R_{18}$ represents an H atom, a Na atom or a K atom;

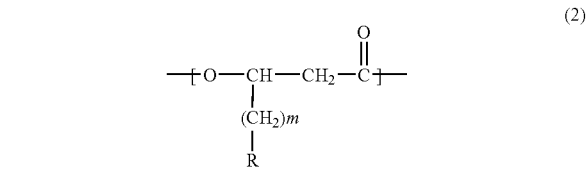

$m = 1-8$ in which m represents an integer selected within a range indicated in the chemical formula; R includes a residue having any of a phenyl structure or a thienyl structure; and in case plural units are present, m and R may be the same or different for each unit;

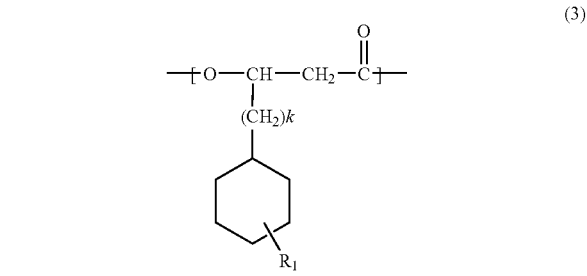

$k = 0-8$ in which $R_1$ represents a substituent on a cyclohexyl group and represents a hydrogen atom, a CN group, a $NO_2$ group, a halogen atom, a $CH_3$ group, a $C_2H_5$ group, a $C_3H_7$ group, a $CF_3$ group, a $C_2F_5$ group, or a $C_3F_7$ group; k represents an integer selected within a range indicated in the chemical formula; and in case plural units are present, $R_1$ and k may be the same or different for each unit.

In the present invention, R in the chemical formula (2) represents a residue having a phenyl structure or a thienyl structure selected from the group consisting of chemical formulas (8), (9), (10), (11), (12), (13), (14), (15), (16), (17) and (18):

the chemical formula (8):

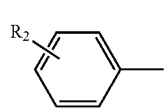
(8)

represents a group of non-substituted or substituted phenyl groups in which $R_2$, a substituent on an aromatic ring and represents an H atom, represents a halogen atom, a CN group, a $NO_2$ group, a $CH_3$ group, a $C_2H_5$ group, a $C_3H_7$ group, a $CH=CH_2$ group, a $COOR_3$ group ($R_3$ represents an H atom, a Na atom or a K atom) which is not included when produced by a microorganism, a $CF_3$ group, a $C_2F_5$ group, or a $C_3F_7$ group; and in case plural units are present, $R_2$ is the same or different for each unit;

the chemical formula (9):

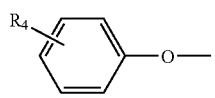
(9)

represents a group of non-substituted or substituted phenoxy groups in which $R_4$ represents a substituent on an aromatic ring and represents an H atom, a halogen atom, a CN group, a $NO_2$ group, a $CH_3$ group, a $C_2H_5$ group, a $C_3H_7$ group, a $SCH_3$ group, a $CF_3$ group, a $C_2F_5$ group, or a $C_3F_7$ group; and in case plural units are present, $R_4$ may be the same or different for each unit;

the chemical formula (10):

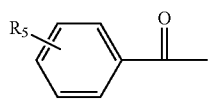
(10)

represents a group of non-substituted or substituted benzoyl groups in which $R_5$ represents a substituent on an aromatic ring and represents an H atom, a halogen atom, a CN group, a $NO_2$ group, a $CH_3$ group, a $C_2H_5$ group, a $C_3H_7$ group, a $CF_3$ group, a $C_2F_5$ group, or a $C_3F_7$ group; and in case plural units are present, $R_5$ may be the same or different for each unit;

the chemical formula (11)

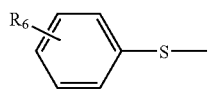
(11)

represents a group of substituted or non-substituted phenylsulfanyl groups in which $R_6$ represents a substituent on an aromatic ring and represents an H atom, a halogen atom, a CN group, a $NO_2$ group, a $COOR_7$ group, a $SO_2R_8$ group ($R_7$ represents either one of H, Na, K, $CH_3$ and $C_2H_5$; and $R_8$ represents either one of OH, ONa, OK, a halogen atom, $OCH_3$ and $OC_2H_5$), a $CH_3$ group, a $C_2H_5$ group, a $C_3H_7$ group, a $(CH_3)_2$—CH group or a $(CH_3)_3$—C group; and in case plural units are present, $R_6$ may be the same or different for each unit;

the chemical formula (12):

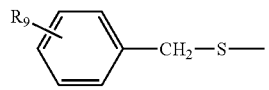
(12)

represents a group of substituted or non-substituted (phenylmethyl)sulfanyl groups in which $R_9$ represents a substituent on an aromatic ring and represents an H atom, a halogen atom, a CN group, a $NO_2$ group, a $COOR_{10}$ group, a $SO_2R_{11}$ group ($R_{10}$ represents either one of H, Na, K, $CH_3$ and $C_2H_5$; and $R_{11}$ represents either one of OH, ONa, OK, a halogen atom, $OCH_3$ and $OC_2H_5$), a $CH_3$ group, a $C_2H_5$ group, a $C_3H_7$ group, a $(CH_3)_2$—CH group or a $(CH_3)_3$—C group; and in case plural units are present, $R_9$ may be the same or different for each unit;

the chemical formula (13):

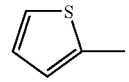
(13)

represents a 2-thienyl group;

the chemical formula (14)

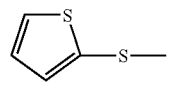
(14)

represents a 2-thienylsulfanyl group;

the chemical formula (15):

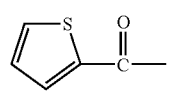
(15)

represents a 2-thienylcarbonyl group;

the chemical formula (16):

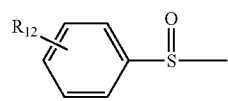
(16)

represents a group of substituted or non-substituted phenylsulfinyl groups in which $R_{12}$ represents a substituent on an aromatic ring and represents an H atom, a halogen atom, a CN group, a $NO_2$ group, a $COOR_{13}$ group, a $SO_2R_{14}$ group ($R_{13}$ represents either one of H, Na, K, $CH_3$ and $C_2H_5$; and $R_{14}$ represents either one of OH, ONa, OK, a halogen atom, $OCH_3$ and $OC_2H_5$), a $CH_3$ group, a $C_2H_5$ group, a $C_3H_7$ group, a $(CH_3)_2$—CH group or a $(CH_3)_3$—C group; and in case plural units are present, $R_{12}$ may be the same or different for each unit;

the chemical formula (17):

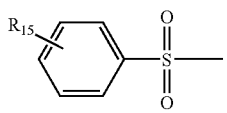

represents a group of substituted or non-substituted phenylsulfonyl groups in which $R_{15}$ represents a substituent on an aromatic ring and represents an H atom, a halogen atom, a CN group, a $NO_2$ group, a $COOR_{16}$ group, a $SO_2R_{17}$ group ($R_{16}$ represents either one of H, Na, K, $CH_3$ and $C_2H_5$; and $R_{17}$ represents either one of OH, ONa, OK, a halogen atom, $OCH_3$ and $OC_2H_5$), a $CH_3$ group, a $C_2H_5$ group, a $C_3H_7$ group, a $(CH_3)_2$—CH group or a $(CH_3)_3$—C group; and in case plural units are present, $R_{15}$ may be the same or different for each unit; and the chemical formula (18):

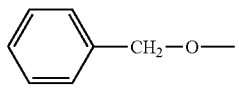

represents a (phenylmethyl)oxy group.

The producing methods therefor are mainly classified to:

a method of oxidizing a double bond portion in a polyhydroxy alkanoate copolymer (hereinafter also called a precursor vinyl PHA) including a 3-hydroxy-ω-alkenoic acid unit having a carbon-carbon double bond at an end of a side chain as represented in a chemical formula (1)

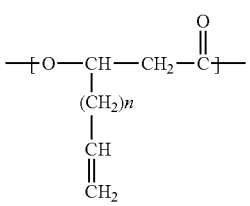

$n = 1–8$ in which n represents an integer selected within a range indicated in the chemical formula; and in case plural units are present, such units may be mutually different), and a unit represented by a chemical formula (2) or a chemical formula (3); and a method of hydrolyzing an alkoxycarbonyl portion in a polyhydroxy alkanoate copolymer (hereinafter also called an alkoxycarbonyl PHA) including a 3-hydroxy-ω-alkoxyalkanoic acid unit having an ester group at an end of a side chain as represented in a chemical formula (48):

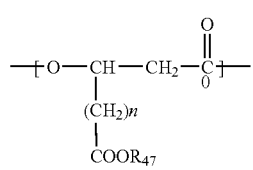

$n = 1–8$ in which n represents an integer selected within a range indicated in the chemical formula; $R_{47}$ represents any of residues indicated in the chemical formula; and in case plural units are present, n and $R_{41}$ may be the same or different for each unit, and a unit represented by a chemical formula (2) or a chemical formula (3). In the following, the precursor vinyl PHA and the precursor alkoxycarbonyl PHA may be collectively called a precursor PHA.

A producing method for such precursor PHA is not particularly restricted, but there can be employed a microbial production using microorganisms, a method using a genetically modified plant, or a chemical polymerization. Preferably a method by microbial production is employed.

The precursor vinyl PHA and the precursor ester (alkoxycarbonyl) PHA were synthesized for the first time by the present inventors, and the present invention therefore includes also the precursor vinyl PHA and the precursor ester PHA themselves, and a production process thereof by microorganisms. Also such precursor vinyl PHA and precursor ester PHA can be effectively utilized not only for the carboxyl PHA which is an object of the present invention but also for introducing other functional groups.

In the following, there will be explained a producing method employing each precursor PHA.

The precursor vinyl PHA can be producing by culturing a microorganism in a culture medium including an ω-alkenoic acid represented by a chemical formula (24) and a compound represented by a chemical formula (25) or an ω-cyclohexylalkanoic acid represented by a chemical formula (26).

Similarly, the precursor alkoxycarbonyl PHA can be producing by culturing a microorganism in a culture medium including a carboxylic acid monoester compound represented by a chemical formula (49) and a compound represented by the chemical formula (25) or an ω-cyclohexylalkanoic acid represented by the chemical formula (26).

The chemical formulas (24), (49), (25) and (26) are as follows:

Chemical Formula (24)

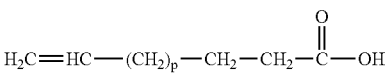

$p = 1–8$

Chemical Formula (49)

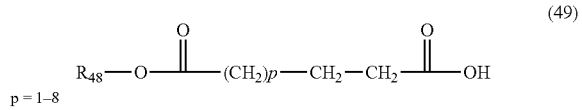

(wherein p is an integer selected within a range indicated in the chemical formula; and $R_{48}$ is either one of residues shown in the chemical formula.)

Chemical Formula (25)

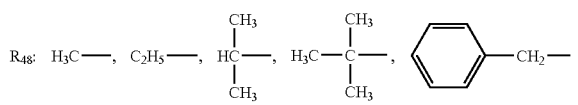

(wherein q is an integer selected within a range indicated in the chemical formula; and $R_{23}$ represents a residue including a phenyl structure or a thienyl structure.)

Chemical Formula (26)

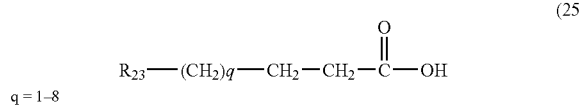

(wherein $R_{24}$ is a substituent on the cyclohexyl group and represents a hydrogen atom, a CN group, a $NO_2$ group, a halogen atom, a $CH_3$ group, a $C_2H_5$ group, a $C_3H_7$ group, a $CF_3$ group, a $C_2F_5$ group, or a $C_3F_7$ group; and r is an integer selected within a range indicated in the chemical formula.)

More specifically, each precursor PHA can be more advantageously prepared by culturing a microorganism in a culture medium containing respective raw material compounds, namely, for the precursor vinyl PHA, a combination of at least one ω-alkenoic acid represented by the chemical formula (24) and at least one compound represented by the chemical formula (25) or at least one ω-cyclohexylalkanoic acid represented by the chemical formula (26); and for the precursor alkoxycarbonyl PHA, a combination of at least one carboxylic acid monoester compound represented by the chemical formula (49) and at least one compound represented by the chemical formula (25) or at least one ω-cyclohexylalkanoic acid represented by the chemical formula (26), and further containing at least one of peptide, yeast extract, organic acid or salt thereof, amino acid or a salt thereof, sugar, and linear alkanoic acid with 4 to 12 carbon atoms or salt thereof.

As preferable nutrients to be added to the culture medium, the peptide being polypeptone; one or more organic acids selected from the group of pyruvic acid, oxaloacetic acid, citric acid, isocitric acid, ketoglutaric acid, succinic acid, fumaric acid, malic acid, lactic acid and salts thereof; one or more amino acids selected from the group of glutamic acid, aspartic acid and salts thereof; and one or more sugars selected from the group of glyceraldehyde, erythrose, arabinose, xylose, glucose, galactose, mannose, fructose, glycerol, erythritol, xylitol, gluconic acid, glucuronic acid, galacturonic acid, maltose, sucrose and lactose.

In the producing method of the precursor PHA copolymer of the present invention, detailed microbial culture conditions are as follows.

The following necessary substrates and nutrients are added to an inorganic salt culture medium based on a phosphate buffer and an ammonium salt or a nitrate salt.

The raw material compound for each precursor PHA, namely, for the precursor vinyl PHA, a combination of at least an ω-alkenoic acid represented by the chemical formula (24) and at least a compound represented by the chemical formula (25) or at least an ω-cyclohexylalkanoic acid represented by the chemical formula (26); or for the precursor alkoxycarbonyl PHA, a combination of at least a carboxylic acid monoester compound represented by the chemical formula (49) and at least a compound represented by the chemical formula (25) or at least an ω-cyclohexylalkanoic acid represented by the chemical formula (26), is preferably contained in the culture medium in a proportion of 0.01 to 1% (w/v), further preferably 0.02 to 0.2%.

The aforementioned nutrients as a carbon source and a nitrogen source for proliferation, and as an energy source for polyhydroxy alkanoate production are preferably added to the culture medium in a proportion of 0.1 to 5% (v/v) per medium, more preferably 0.2 to 2%.

It can be employed any inorganic salt culture medium containing a phosphate salt and a nitrogen source such as an ammonium salt or a nitrate salt, but the PHA productivity can be improved by regulating the concentration of the nitrogen source.

The culture temperature can be any temperature at which the microorganism can satisfactorily proliferate, and is usually within a range of 15 to 37° C., preferably 20 to 30° C.

The culture may be carried out by any culture method so long as the microorganisms can proliferate and produce PHA, such as a liquid culture or a solid culture. Also it may be batch culture, fed batch culture, semi-continuous culture or continuous culture. For example, for liquid batch culture, the oxygen supply method may be shaking using a shaking flask or agitation aeration in a jar fermenter.

In order to make the microorganism produce and accumulate PHA, there can be employed, in addition to the aforementioned method, a method of transferring the cell, after sufficient proliferation, to a culture medium limited in a nitrogen source such as ammonium chloride and to continue culture further in the presence of a compound being a substrate for the desired unit, thereby improving the productivity.

Thus the method for producing precursor vinyl PHA of the present invention may comprise the steps of: culturing a production microorganism under the aforementioned conditions, and recovering produced PHA from the cells, the PHA copolymer produced by the microorganism at least containing a 3-hydroxy-ω-alkenoic acid unit represented by the chemical formula (1), and a unit represented by the chemical formula (2) or an ω-cyclohexylalkanoic acid unit represented by the chemical formula (3) in the molecule.

Also the method for producing precursor alkoxycarbonyl PHA of the present invention may comprise the steps of: culturing a production microorganism under the aforementioned conditions, and recovering from the cells a polyhydroxy alkanoate copolymer produced by the microorganism which at least contains a 3-hydroxy-ω-alkoxycarbonylalkanoic acid unit represented by the chemical formula (48), and a unit represented by the chemical formula (2) or an ω-cyclohexylalkanoic acid unit represented by the chemical formula (3) in the molecule.

The object PHA can be recovered from the cells by an ordinarily employed method. For example, an extraction with an organic solvent such as chloroform, dichloromethane, ethyl acetate or acetone is most simple, but there may also be employed dioxane, tetrahydrofuran or acetonitrile. Also in a situation where an organic solvent is difficult to use, it is also possible to physically break the cells, for example by treating the cells with a surfactant such as SDS, chemicals such as hypochlorous acid and EDTA, or with an enzyme such as lysozyme, or by ultrasonic disruption, homogenizer disruption, pressure disruption, beads impulse, grinding or pounding or freeze-and-thawing, to remove cell components other than PHA and recover PHA.

A production microorganism to be employed in the production method of the present invention can be any microorganisms having an ability meeting the aforementioned conditions, but there are preferred those belonging to the *Pseudomonas* genus, and more preferably *Pseudomonas cichorii, Pseudomonas putida, Pseudomonas fluorescens, Pseudomonas oleovorans, Pseudomonas aeruginosa, Pseudomonas stutzeri* or *Pseudomonas jessenii*. More specific examples include *Pseudomonas cichorii* YN2 (FERM BP-7375), *Pseudomonas cichorii* H45 (FERM BP-7374), *Pseudomonas jessenii* P161 (FERM BP-7376), and *Pseudomonas putida* P91 (FERM BP-7373). These four types of strains are deposited on Nov. 20, 2000 at International Patent Organism Depositary, National Institute of Bioscience and Human-Technology, Agency of Industry Science and Technology (independent administrative corporation), Tsukuba Central 6, 1-1, Higashi 1-chome, Tsukuba-shi, Ibaraki-ken 305-8566, Japan, and described in the Japanese Patent Application Laid-Open No. 2002-80571.

In the present invention the methods for culture of the microorganism, PHA production and accumulation by the microorganism, and for PHA recovery from the cells are not limited to the methods explained above.

The following is a composition of an inorganic salt M9 culture medium employed in the method of the present invention.

| [M9 culture medium] | |
|---|---|
| $Na_2HPO_4$ | 6.3 |
| $KH_2PO_4$ | 3.0 |
| NaCl | 0.5 |
| $NH_4Cl$ | 1.0 |

(in g/L; pH 7.0)

For satisfactory proliferation and resulting PHA production, the above-mentioned inorganic culture medium has to be replenished with the essential trace elements by adding the following trace component solution by about 0.3% (v/v).

| [Minor component solution] | |
|---|---|
| nytrilotriacetic acid | 1.5; |
| $MgSO_4$ | 3.0; |
| $MnSO_4$ | 0.5; |
| NaCl | 1.0; |
| $FeSO_4$ | 0.1; |
| $CaCl_2$ | 0.1; |
| $CoCl_2$ | 0.1; |
| $ZnSO_4$ | 0.1; |
| $CuSO_4$ | 0.1; |
| $AlK(SO_4)_2$ | 0.1; |
| $H_3BO_3$ | 0.1; |
| $Na_2MoO_4$ | 0.1; |
| $NiCl_2$ | 0.1; |

(in g/L).

The polyhydroxy alkanoates synthesized by the aforementioned producing method, a polyhydroxy alkanoate copolymer including a unit represented by the chemical formula (1) and a unit represented by the chemical formula (2) or a unit represented by the chemical formula (3) can be oxidized at the carbon-carbon double bond portion to give a polyhydroxy alkanoate copolymer including a unit represented by the chemical formula (19), and a unit represented by the chemical formula (2) or a unit represented by the chemical formula (3). For obtaining a carboxylic acid by oxidizing a carbon-carbon double bond with an oxidant, there are known, for example, a method of utilizing a permanganate salt (J. Chem. Soc. Perkin. Trans. 1, 806(1973)); a method of utilizing a bichromate salt (Org. Synth., 4, 698(1963)); a method of utilizing a periodate salt (J. Org. Chem., 46, 19(1981)); a method of utilizing nitric acid (Japanese Patent Application Laid-Open No. S59-190945); a method of utilizing ozone (J. Am. Chem. Soc., 81, 4273(1959)) etc., and, on polyhydroxy alkanoate, Macromolecular chemistry, 4, 289-293(2001) reports a method of obtaining a carboxylic acid by oxidizing the carbon-carbon double bond at the end of the side chain of polyhydroxy alkanoate with potassium permanganate as an oxidant and under an acidic condition. A similar method can be utilized also in the present invention.

The oxidant to be employed in the present invention, though not particularly limited, is preferably a permanganate salt. Such permanganate salt to be employed as the oxidant is usually potassium permanganate. Since the oxidation reaction is a stoichiometric reaction, the amount of the permanganate salt is usually 1 molar equivalent or more with respect to 1 mole of the unit represented by the chemical formula (1), preferably 2 to 10 molar equivalents.

For executing the reaction under an acidic condition, there is usually employed an inorganic acid such as sulfuric acid, hydrochloric acid, acetic acid or nitric acid, or an organic acid. However the use of sulfuric acid, nitric acid or hydrochloric acid may cause cleavage of an ester bond in the main chain of polyhydroxy alkanoate, thereby resulting in a decrease in the molecular weight. It is therefore preferable to employ acetic acid. An amount of acid is usually within a range of 0.2 to 2000 molar equivalents per 1 mole of the unit represented by the chemical formula (1), preferably 0.4 to 1000 molar equivalents. An amount less than 0.2 molar equivalents results in a low yield, while an amount exceeding 2000 molar equivalents generates by-products by decomposition with acid. Also a crown ether may be employed for the purpose of accelerating the reaction. In this case, crown ether and permanganate salt form a complex, thereby providing an effect of increasing the reaction activity. As the crown ether, there is generally employed dibenzo-18-crown-6-ether, dicyclo-18-crown-6-ether, or 18-crown-6-ether. An amount of crown ether is generally within a range of 0.005 to 2.0 molar equivalents per 1 mole of permanganate salt, preferably 0.05 to 1.5 molar equivalents.

As a solvent to be employed in the oxidation reaction of the present invention, there may be employed any solvent inert to the reaction without particular limitation, for example water, acetone; an ether such as tetrahydrofuran or dioxane; an aromatic hydrocarbon such as benzene; an aliphatic hydrocarbon such as hexane or heptane; or a halogenated hydrocarbon such as methyl chloride, dichloromethane or chloroform. Among these solvents, in consideration of dissolving property for the polyhydroxy alkanoate, a halogenated hydrocarbon such as methyl chloride, dichloromethane or chloroform, or acetone is preferred.

In the aforementioned oxidation reaction of the present invention, a precursor vinyl PHA, a permanganate salt and an acid may be introduced into a solvent at a time from the beginning and reacted together, or they may be added to the reaction system one by one continuously or intermittently to be reacted. Or first a permanganate alone is dissolved or suspended in a solvent, followed by continuous or intermittent addition of a polyhydroxyalkanoate and an acid to the reaction system, or first a polyhydroxyalkanoate alone is dissolved or suspended in a solvent, followed by continuous or intermittent addition of a permanganate and an acid to the reaction system. Further, first a polyhydroxyalkanoate and an acid are introduced into a solvent and then a permanganate is added to the reaction system continuously or intermittently to be reacted, or first permanganate and an acid are introduced into a solvent and then polyhydroxyalkanoate is added to the reaction system continuously or intermittently, or first a polyhydroxyalkanoate and a permanganate are introduced into a solvent and then an acid is added to the reaction system continuously and intermittently to be reacted.

A reaction temperature is selected generally within a range from −40 to 40° C., preferably −10 to 30° C. A reaction time depends on a stoichiometric ratio of the unit represented by the chemical formula (1) and permanganate salt and the reaction temperature, but is generally selected within a range of 2 to 48 hours.

Also in the oxidation reaction of the present invention, in case $R_2$ in the unit represented by the chemical formula (2) is a residue represented by the chemical formula (11), a sulfide bond therein may be converted into a sulfoxide or a sulfone.

Next, there will be explained the producing method of the precursor ester PHA of the present invention employing, as a starting material, a polyhydroxy alkanoate copolymer including a unit represented by the chemical formula (48), and a unit represented by a chemical formula (2) or a unit represented by a chemical formula (3).

A precursor ester PHA synthesized can provide the carboxyl PHA by hydrolysis in the presence of an acid or an alkali or hydrogenolysis including catalytic reduction of an ester bond portion shown in the chemical formula (48). Such method of hydrolysis in the presence of an acid or an alkali can be carried out by employing, in a water-miscible organic solvent such as methanol, ethanol, tetrahydrofuran, dioxane, dimethylformamide or dimethylsulfoxide, an aqueous solution or an inorganic acid such as hydrochloric acid, sulfuric acid, nitric acid or phosphoric acid; an organic acid such as trifluoroacetic acid, trichlorbacetic acid, p-toluenesulfonic acid or methanesulfonic acid; an aqueous caustic alkali such as sodium hydroxide or potassium hydroxide; an.aqueous solution or an alkali carbonate such as sodium carbonate or potassium carbonate; or an alcoholic solution of a metal alkoxide such as sodium methoxide or sodium ethoxide. The reaction temperature is selected ordinarily from 0 to 40° C., preferably from 0 to 30° C. The reaction period is ordinarily selected from 0.5 to 48 hours. However, a hydrolysis with an acid or an alkali may also cause a cleavage of an ester bonding of the main molecular chain, thereby resulting in a decrease in the molecular weight.

Also the method of obtaining a carboxylic acid by hydrogenolysis including catalytic reduction is carried out in the following manner. Catalytic reduction is carried out in a suitable solvent and within a temperature range from −20° C. to the boiling point of the used solvent, preferably from 0 to 50° C., by reacting hydrogen under a normal pressure or an elevated pressure in the presence of a reducing catalyst. Examples of the usable solvent include water, methanol, ethanol, propanol, ethyl acetate, diethyl ether, tetrahydrofuran, dioxane, benzene, toluene, dimethylformamide and pyridine. In consideration of the solubility, tetrahydrofuran, toluene or dimethylformamide is particularly preferable. As the reducing catalyst, there can be employed palladium, platinum or rhodium either singly or held on a carrier, or Raney nickel. However, the catalytic reduction may also cause cleavage of an ester bonding of the main molecular chain to decrease the molecular weight.

In the following, the present invention will be explained in more details by examples thereof. These examples represent examples of the optimum embodiments of the present invention, but the present invention is by no means limited by these examples.

EXAMPLES

Example 1

0.5% of polypeptone (supplied by Wako Pure Chemical Co.), 6 mmol/L of 5-phenoxyvaleric acid, and 1 mmol/L of 10-undecenoic acid were dissolved in 200 ml of an aforementioned M9 culture medium, which was placed in a 200 ml shaking flask, then sterilized in an autoclave and cooled to the room temperature. Then 2 ml of a culture liquid of *Pseudomonas cichorii* YN2, shake cultured in advance in an M9 culture medium containing 0.5% of polypeptone for 8 hours at 30° C., was added to the prepared culture medium, and culture was conducted for 64 hours at 30° C. After the culture, the cells were collected by centrifugation, washed with methanol and dried. The dried cells, after weighing, were put in chloroform and stirred for 72 hours at 35° C. to extract a polymer. The chloroform extract was filtered, then concentrated on an evaporator, and a solid precipitate formed by an addition of cold methanol was collected and dried under a reduced pressure to obtain a desired polymer.

Structure of the obtained polymer was determined by $^1$H-NMR (FT-NMR: Bruker DPX400; resonance frequency: 400 MHz; measured nucleus species: $^1$H; solvent: CDCl$_3$; reference: capillary-sealed TMS/CDCl$_3$; measurement temperature: room temperature) and $^{13}$C-NMR (FT-NMR: Bruker DPX400; resonance frequency: 100 MHz; measured nucleus species: $^{13}$C; solvent: CDCl$_3$; reference: capillary-sealed TMS/CDCl$_3$; measurement temperature: room temperature).

FIG. 1 shows a $^1$H-NMR spectrum of the obtained polymer. As a result, the obtained polymer was confirmed being a polyhydroxy alkanoate copolymer including a unit represented by the following chemical formula (50) (A:B+C+D: others (linear 3-hydroxyalkanoic acid with 4 to 12 carbon atoms and 3-hydroxylalk-5-enoic acid with 10 or 12 carbon atoms)=87:9:4). Also $^{13}$C-NMR confirmed presence of the unit B which is a 3-hydroxy-10-undecenoic acid unit and both of the unit C which is a 3-hydroxy-8-nonenoic acid unit and the unit D which is a 3-hydroxy-6-heptenoic acid unit, but the ratio of the units B, C and D was not determined.

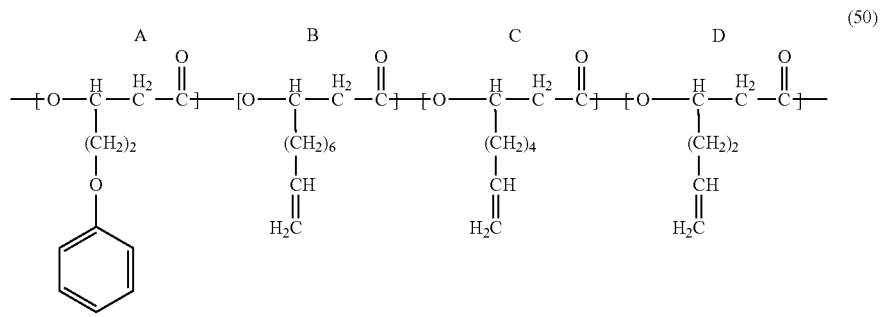

(50)

The molecular weight of the obtained polymer was measured by gel permeation chromatography (GPC) (Toso HLC-8220 GPC, column: Toso TSK-GEL Super HM-H, solvent: chloroform, molecular weight converted into polystyrene).

The obtained polymer dry weight (PDW) was 0.19 g/L and the number-averaged molecular weight was 30,000.

Example 2

A desired polymer was obtained in the same manner as in Example 1, except that 5-phenoxyvaleric acid employed in Example 1 was changed to 4-phenoxybutyric acid.

Structure of the obtained polymer was determined by $^1$H-NMR and $^{13}$C-NMR (FT-NMR: Bruker DPX400 as in Example 1. As a result, the obtained polymer was confirmed being a polyhydroxy alkanoate copolymer including units represented by the following chemical formula (51) (A:B+C+D: others (linear 3-hydroxyalkanoic acid with 4 to 12 carbon atoms and 3-hydroxylalk-5-enoic acid with 10 or 12 carbon atoms)=72:11:15). Also $^{13}$C-NMR confirmed the presence of the unit B which is a 3-hydroxy-10-undecenoic acid unit and both of the unit C which is a 3-hydroxy-8-nonenoic acid unit and the unit D which is a 3-hydroxy-6-heptenoic acid unit, but the ratio of the units B, C and D was not determined.

The molecular weight of the obtained polymer was measured by GPC as in Example 1.

The obtained polymer weighed (PDW) 0.05 g/L and a number-averaged molecular weight was 25,000.

Example 3

A desired polymer was obtained in the same manner as in Example 1, except that 5-phenoxyvaleric acid employed in Example 1 was changed to 4-cyclohexylbutyric acid.

Structure of the obtained polymer obtained by $^1$H-NMR and $^{13}$C-NMR as in Example 1 was determined to confirm that the polyhydroxy alkanoate copolymer includes units represented by the following chemical formula (52) (A+others (linear 3-hydroxyalkanoic acid with 4 to 12 carbon atoms and 3-hydroxylalk-5-enoic acid with 10 or 12 carbon atoms): B+C+D=89:11). Also $^{13}$C-NMR confirmed the presence of the unit B being a 3-hydroxy-10-undecenoic acid unit and both of the unit C being a 3-hydroxy-8-nonenoic acid unit and the unit D being a 3-hydroxy-6-heptenoic acid unit, but the ratio of the units B, C and D was not determined.

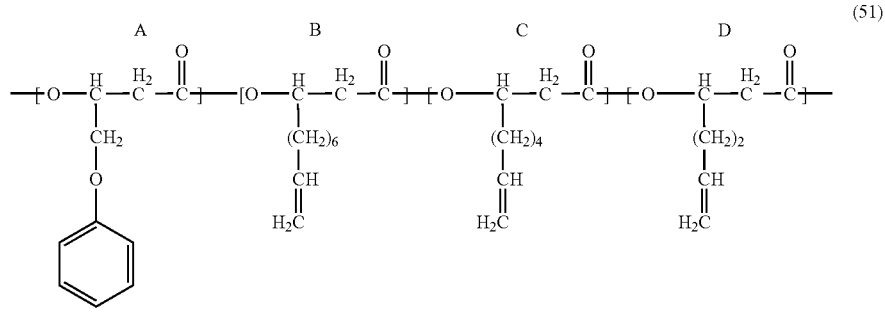

(51)

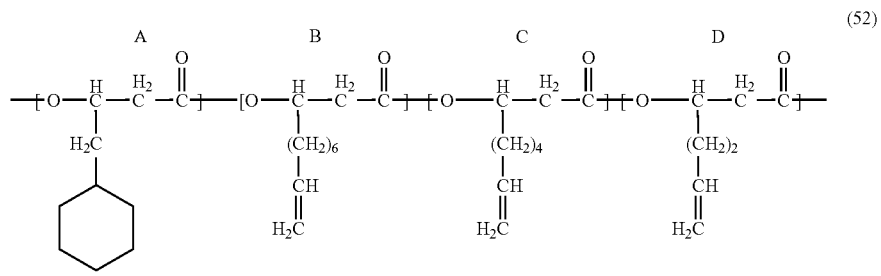

(52)

The molecular weight of the obtained polymer was measured by GPC as in Example 1.

The obtained polymer weighed (PDW) 0.52 g/L and the number-averaged molecular weight was 154,000.

Example 4

A desired polymer was obtained in the same manner as in Example 3, except that polypeptone employed in Example 3 was changed to yeast extract.

Structure of the obtained polymer was determined by $^1$H-NMR and $^{13}$C-NMR as in Example 1 to confirm the polymer being a polyhydroxy alkanoate copolymer including units represented by the following chemical formula (52) (A+others (linear 3-hydroxyalkanoic acid with 4 to 12 carbon atoms and 3-hydroxylalk-5-enoic acid with 10 or 12 carbon atoms): B+C+D=85:15). Also $^{13}$C-NMR confirmed the presence of the unit B is a 3-hydroxy-10-undecenoic acid unit and both of the unit C being a 3-hydroxy-8-nonenoic acid unit and the unit D being a 3-hydroxy-6-heptenoic acid unit, but the ratio of the units B, C and D was not determined.

The molecular weight of the obtained polymer was measured by GPC as in Example 1.

The obtained polymer weighed (PDW) 0.45 g/L and the number-averaged molecular weight was 132,000.

Example 5

A polymer was obtained in the same manner as in Example 3, except that the strain YN2 employed in Example 3 was replaced by *Pseudomonas cichorii* H45 and polypeptone was changed to glucose. Structure of the obtained polymer was determined by $^1$H-NMR and $^{13}$C-NMR as in Example 1 to confirm the polymer being a polyhydroxy alkanoate copolymer including units represented by the following chemical formula (52) (A+others (linear 3-hydroxyalkanoic acid with 4 to 12 carbon atoms and 3-hydroxylalk-5-enoic acid with 10 or 12 carbon atoms): B+C+D=83:17). Also $^{13}$C-NMR confirmed the presence of the unit B being a 3-hydroxy-10-undecenoic acid unit and both of the unit C being a 3-hydroxy-8-nonenoic acid unit and the unit D being a 3-hydroxy-6-heptenoic acid unit, but the ratio of the units B, C and D was not determined.

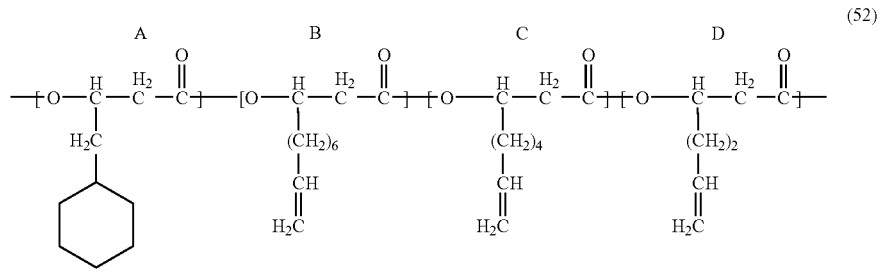

(52)

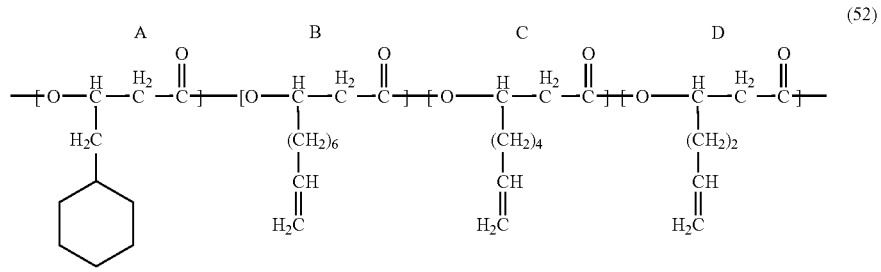

(52)

The molecular weight of the obtained polymer was measured by GPC as in Example 1.

The obtained polymer weighed (PDW) 0.41 g/L and the number-averaged molecular weight was 164,000.

Example 6

A polymer was obtained in the same manner as in Example 3, except that the strain YN2 employed in Example 3 was replaced by *Pseudomonas cichorii* H45 and polypeptone was changed to sodium pyruvate. A structure determination of the obtained polymer was conducted by $^1$H-NMR and $^{13}$C-NMR as in Example 1 to confirm the polymer being a polyhydroxyalkanoate copolymer including units represented by the following chemical formula (52) (A+others (linear 3-hydroxyalkanoic acid with 4 to 12 carbon atoms and 3-hydroxyalk-5-enoic acid with 10 or 12 carbon atoms): B+C+D=87:13). Also $^{13}$C-NMR confirmed the presence of the unit B being a 3-hydroxy-10-undecenoic acid unit and the unit C being a 3-hydroxy-8-nonenoic acid unit and the unit D being a 3-hydroxy-6-heptenoic acid unit, but the ratio of the units B, C and D was not determined.

The molecular weight of the obtained polymer was measured by GPC as in Example 1.

The weight of the obtained polymer (PDW) was 0.28 g/L and the number-averaged molecular weight was 156,000.

Example 7

A polymer was obtained in the same manner as in Example 3, except that the strain YN2 employed in Example 3 was replaced by *Pseudomonas jessenii* P161 and polypeptone was changed to sodium glutamate. Structure determination of the obtained polymer was conducted by $^1$H-NMR and $^{13}$C-NMR as in Example 1 to confirm the polymer being a polyhydroxyalkanoate copolymer including units represented by the following chemical formula (52) (A+others (linear 3-hydroxyalkanoic acid with 4 to 12 carbon atoms and 3-hydroxyalk-5-enoic acid with 10 or 12 carbon atoms): B+C+D=88:12). Also $^{13}$C-NMR confirmed the presence of the unit B being a 3-hydroxy-10-undecenoic acid unit and both of the unit C being a 3-hydroxy-8-nonenoic acid unit and the unit D being a 3-hydroxy-6-heptenoic acid unit, but the ratio of the units B, C and D was not determined.

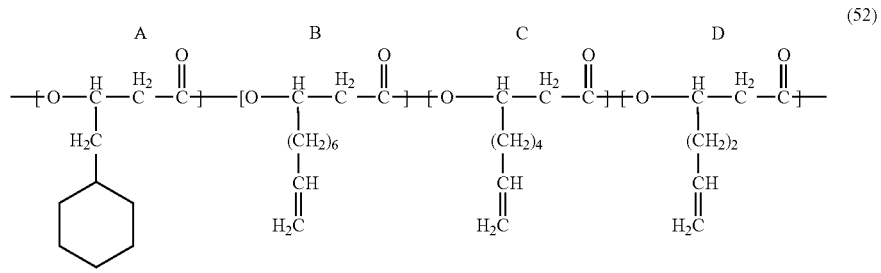

(52)

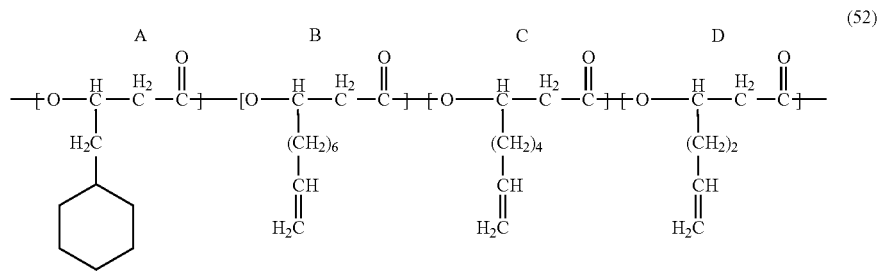

(52)

The molecular weight of the obtained polymer was measured by GPC as in Example 1.

The weight of the obtained polymer (PDW) was 0.38 g/L and the number-averaged molecular weight of 145,000.

Example 8

A polymer was obtained in the same manner as in Example 3, except that the strain YN2 employed in Example 3 was replaced by *Pseudomonas jessenii* P161 and 0.5% polypeptone was changed to 0.1% of nonanic acid. The structure determination of the obtained polymer was conducted by $^1$H-NMR and $^{13}$C-NMR as in Example 1 to confirm the polymer being a polyhydroxy alkanoate copolymer including units represented by the following chemical formula (52) (A+others (linear 3-hydroxyalkanoic acid with 4 to 12 carbon atoms and 3-hydroxylalk-5-enoic acid with 10 or 12 carbon atoms): B+C+D=80:20). Also $^{13}$C-NMR confirmed the presence of the unit B being a 3-hydroxy-10-undecenoic acid unit and both of the unit C being a 3-hydroxy-8-nonenoic acid unit and the unit D being a 3-hydroxy-6-heptenoic acid unit, but the ratio of the units B, C and D was not determined.

culture medium was placed, then sterilized in an autoclave and cooled to the room temperature. Then 2 ml of a culture liquid of *Pseudomonas cichorii* YN2, shake cultured in advance in an M9 culture medium containing 0.5% of polypeptone for 8 hours at 30° C., was added to each flask, and culture was conducted for 64 hours at 30° C. After the culture, all cells were collected by centrifugation, washed with methanol and dried. The dried cells, after weighing, were put in chloroform and stirred for 72 hours at 35° C. to extract a polymer. The chloroform extract was filtered, then concentrated on an evaporator, and a solid precipitate formed by an addition of cold methanol was collected and dried under a reduced pressure to obtain a desired polymer.

The obtained PHA polymer weighed 1528 mg (dry weight) in the present example.

The average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight

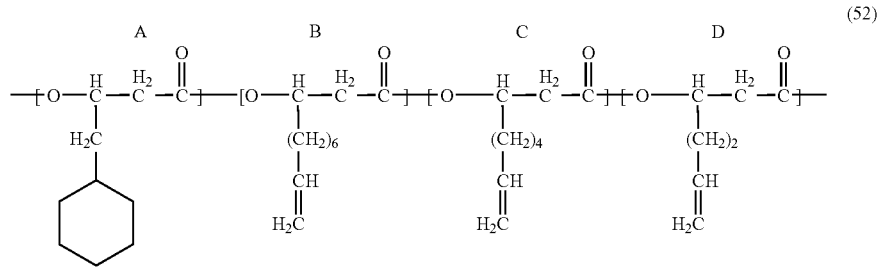

(52)

The molecular weight of the obtained polymer was measured by GPC as in Example 1.

The weight of the obtained polymer (PDW) was 0.18 g/L and the number-averaged molecular weight was 132,000.

Example 9

Twenty 200 ml shaking flasks were prepared, into which 0.5% of polypeptone (supplied by Wako Pure Chemical Co.), 6 mmol/L of 5-phenoxyvaleric acid, and 1 mmol/L of 10-undecenoic acid dissolved in 200 ml of an aforementioned M9

Mn=104000 and a weight-averaged molecular weight Mw=231000. The structure of the obtained polymer was determined by $^1$H-NMR and $^{13}$C-NMR as in Example 1.

As a result, confirmed was a polyhydroxy alkanoate copolymer including, as monomer units, 3-hydroxy-5-phenoxyvaleric acid represented by the following chemical formula (53), 3-hydroxy-10-undecenoic acid represented by a chemical formula (5), 3-hydroxy-8-nonenoic acid represented by a chemical formula (6) and 3-hydroxy-6-heptenoic acid represented by a chemical formula (7).

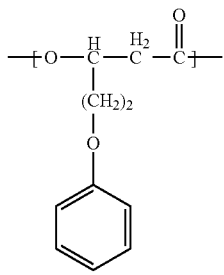
(53)

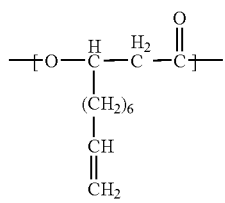
(5)

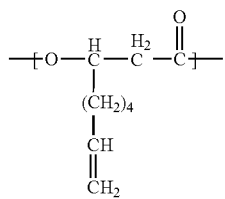
(6)

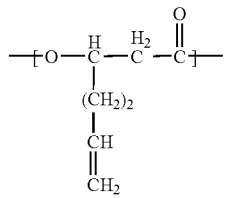
(7)

The proportion of such units confirmed by $^1$H-NMR was: 69 mol % of 3-hydroxy-5-phenoxyvaleric acid, 23 mol % of three units of 3-hydroxy-10-undecenoic acid, 3-hydroxy-8-nonenoic acid and 3-hydroxy-6-heptenoic acid in total, and 8 mol % of others (linear 3-hydroxyalkanoic acids of 4 to 12 carbon atoms and 3-hydroxyalk-5-enoic acids with 10 or 12 carbon atoms).

The polyhydroxy alkanoate thus obtained was utilized in the following reaction.

303 mg of polyhydroxy alkanoate were charged in a 200-ml eggplant-shaped flask and were dissolved by adding 20 ml of dichlordmethane. The solution was placed in an iced bath, and 3 ml of acetic acid and 300 mg of 18-crown-6-ether were added and agitated. Then, in an iced bath, 241 mg of potassium permanganate were slowly added and an agitation was carried out for 20 hours at the room temperature. After the reaction, 50 ml of water and 500 mg of sodium bisulfite were added. Then the liquid was brought to pH=1 by 1.0 N hydrochloric acid. After dichloromethane in the mixed solvent was distilled off in an evaporator, a polymer in the solution was recovered. The polymer was recovered by washing with 100 ml of methanol and washing three times with 100 ml of purified water. A drying under a reduced pressure provided 247 mg of the desired PHA.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=29400 and a weight-averaged molecular weight Mw=102800.

A structure determination of the obtained polymer carried out by $^1$H-NMR and $^{13}$C-NMR as in Example 1 confirmed a polyhydroxy alkanoate copolymer including, as monomer units, 3-hydroxy-5-phenoxyvaleric acid represented by the following chemical formula (53), 3-hydroxy-9-carboxynonanoic acid represented by a chemical formula (54), 3-hydroxy-7-carboxyheptanoic acid represented by a chemical formula (55) and 3-hydroxy-5-carboxyvaleric acid represented by a chemical formula (56).

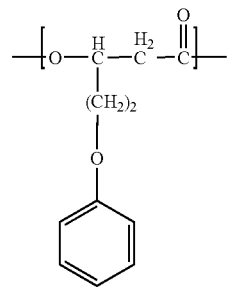
(53)

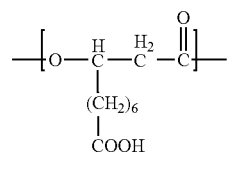
(54)

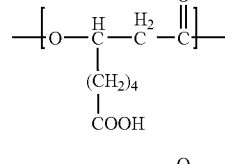
(55)

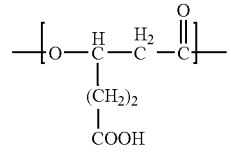
(56)

Also a proportion of the units of the obtained PHA was calculated by a methylesterification, utilizing trimethylsilyldiazomethane, of a carboxyl group at an end of a side chain of the PHA.

50 mg of the object PHA were charged in a 100-ml eggplant-shaped flask and were dissolved by adding 3.5 ml of chloroform and 0.7 ml of methanol. The solution was added with 2 ml of a 0.63 mol/L solution of trimethylsilyldiazomethane in hexane (supplied by Tokyo Kasei Kogyo Co.) and was agitated for 30 minutes at the room temperature. After the reaction, the solvent was distilled off in an evaporator to recover a polymer. The polymer was recovered by washing with 50 ml of methanol. A drying under a reduced pressure provided 49 mg of PHA.

NMR analysis as in Example 1 confirmed a proportion of the units in which 3-hydroxy-5-phenoxyvaleric acid was present by 83 mol %, a sum of three units of 3-hydroxy-9-carboxynonanoic acid, 3-hydroxy-7-carboxyheptanoic acid and 3-hydroxy-5-carboxyvaleric acid by 8 mol %, and others (linear 3-hydroxyalkanoic acid of 4 to 12 carbon atoms and 3-hydroxyalk-5-enoic acid with 10 or 12 carbon atoms) by 9 mol %.

Example 10

There were prepared twenty 500-ml shake flasks, and, in each, 0.5 wt. % of polypeptone (supplied by Wako Pure Chemical Co.), 6 mmol/L of 4-cyclohexylbutyric acid, and 3 mmol/L of 10-undecenoic acid were dissolved in 200 ml of an aforementioned M9 culture medium, which was placed in a 500 ml shake flask, then sterilized in an autoclave and cooled to the room temperature. Then 2 ml of a culture liquid of *Pseudomonas cichorii* YN2 strain, shake cultured in advance in an M9 culture medium containing 0.5% of polypeptone for 8 hours, was added to each prepared culture medium, and culture was conducted for 60 hours at 30° C. After the culture, the culture liquids were united, and the cells were recovered by centrifuging, rinsed with methanol and dried. The dried cells, after weighing, were agitated with chloroform for 72 hours at 25° C. to extract a polymer. The chloroform extract was filtered with a 0.45 μm membrane filter, then concentrated in an evaporator, and the polymer was recovered by a reprecipitation in cold methanol. A desired polymer was then obtained by drying under a reduced pressure.

According to a weighing of the obtained polymer, 1433 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=143000 and a weight-averaged molecular weight Mw=458000.

A structure of the obtained PHA was determined by a NMR analysis as in Example 1.

As a result, there was confirmed a polyhydroxy alkanoate copolymer including, as monomer units, 3-hydroxy-5-cyclohexylbutyric acid represented by the following chemical formula (57), 3-hydroxy-10-undecenoic acid represented by a chemical formula (5), 3-hydroxy-8-nonenoic acid represented by a chemical formula (6) and 3-hydroxy-6-heptenoic acid represented by a chemical formula (7).

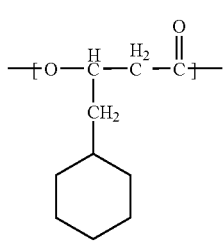
(57)

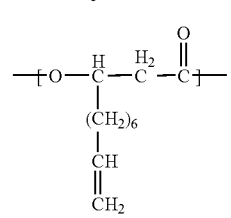
(5)

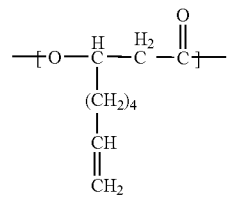
(6)

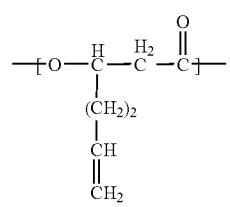
(7)

Also a proportion of such units was confirmed by $^1$H-NMR spectrum, where a sum of three units of 3-hydroxy-10-undecenoic acid, 3-hydroxy-8-nonenoic acid and 3-hydroxy-6-heptenoic acid was present by 37 mol %, and 3-hydroxy-4-cyclohexylbutyric acid and others (linear 3-hydroxyalkanoic acid of 4 to 12 carbon atoms and 3-hydroxyalk-5-enoic acid with 10 or 12 carbon atoms) by 63 mol %.

The polyhydroxy alkanoate thus obtained was utilized in the following reaction.

301 mg of polyhydroxy alkanoate were charged in a 200-ml eggplant-shaped flask and were dissolved by adding 20 ml of dichloromethane. The solution was placed in an iced bath, and 3 ml of acetic acid and 541 mg of 18-crown-6-ether were added and agitated. Then, in an iced bath, 430 mg of potassium permanganate were slowly added and an agitation was carried out for 20 hours at the room temperature. After the reaction, 50 ml of water and 1000 mg of sodium bisulfite were added. Then the liquid was brought to pH=1 by 1.0 N hydrochloric acid. After dichloromethane in the mixed solvent was distilled off in an evaporator, a polymer in the solution was recovered. The polymer was recovered by washing with 100 ml of methanol and washing three times with 100 ml of purified water. A drying under a reduced pressure provided 184 mg of the desired PHA.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=111800 and a weight-averaged molecular weight Mw=272800.

For specifying the structure of the obtained PHA, a NMR analysis was carried out under conditions same as in Example 1.

As a result, there was confirmed a polyhydroxy alkanoate copolymer including, as monomer units, 3-hydroxy-4-cyclohexylvaleric acid represented by the following chemical formula (57), 3-hydroxy-9-carboxynonanoic acid represented by a chemical formula (54), 3-hydroxy-7-carboxyheptanoic acid represented by a chemical formula (55) and 3-hydroxy-5-carboxyvaleric acid represented by a chemical formula (56).

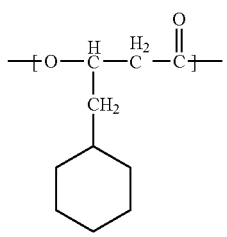
(57)

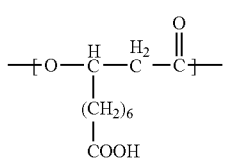
(54)

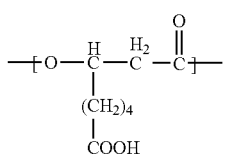
(55)

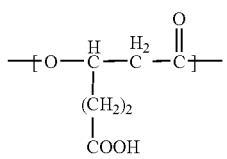
(56)

Also a proportion of the units of the obtained PHA was calculated by a methylesterification, utilizing trimethylsilyldiazomethane, of a carboxyl group at an end of a side chain of the PHA.

30 mg of the object PHA were charged in a 100-ml eggplant-shaped flask and were dissolved by adding 2.1 ml of chloroform and 0.4 ml of methanol. The solution was added with 0.9 ml of a 0.63 mol/L solution of trimethylsilyldiazomethane in hexane (supplied by Tokyo Kasei Kogyo Co.) and was agitated for 30 minutes at the room temperature. After the reaction, the solvent was distilled off in an evaporator to recover a polymer. The polymer was recovered by washing with 50 ml of methanol. A drying under a reduced pressure provided 31 mg of PHA.

A NMR analysis was carried out as in Example 1. As a result, there was confirmed a proportion of the units in which a sum of three units of 3-hydroxy-9-carboxynonanoic acid, 3-hydroxy-7-carboxyheptanoic acid and 3-hydroxy-5-carboxyvaleric acid was present by 9 mol %, and 3-hydroxy-4-cyclohexyl butyric acid and others (linear 3-hydroxyalkanoic acid of 4 to 12 carbon atoms and 3-hydroxyalk-5-enoic acid with 10 or 12 carbon atoms) by 91 mol %.

Example 11

There were prepared three 2000-ml shake flasks, and, in each, 0.5 wt. % of polypeptone (supplied by Wako Pure Chemical Co.), 4.8 mmol/L of 5-(phenylsulfanyl)valeric acid, and 2 mmol/L of 10-undecenoic acid were dissolved in 1000 ml of an aforementioned M9 culture medium, which was placed in a 2000 ml shake flask, then sterilized in an autoclave and cooled to the room temperature. Then 10 ml of a culture liquid of *Pseudomonas cichorii* YN2 strain, shake cultured in advance in an M9 culture medium containing 0.5% of polypeptone for 8 hours, was added to each prepared culture medium, and culture was conducted for 38 hours at 30° C. After the culture, the culture liquids were united, and the cells were recovered by centrifuging, rinsed with methanol and dried. The dried cells, after weighing, were agitated with chloroform for 25 hours at 35° C. to extract a polymer. The chloroform extract was filtered with a 0.45 μm membrane filter, then concentrated in an evaporator, and the polymer was recovered by a reprecipitation in cold methanol. A desired polymer was then obtained by drying under a reduced pressure.

According to a weighing of the obtained polymer, 1934 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=150000 and a weight-averaged molecular weight Mw=430000.

Figure 3:
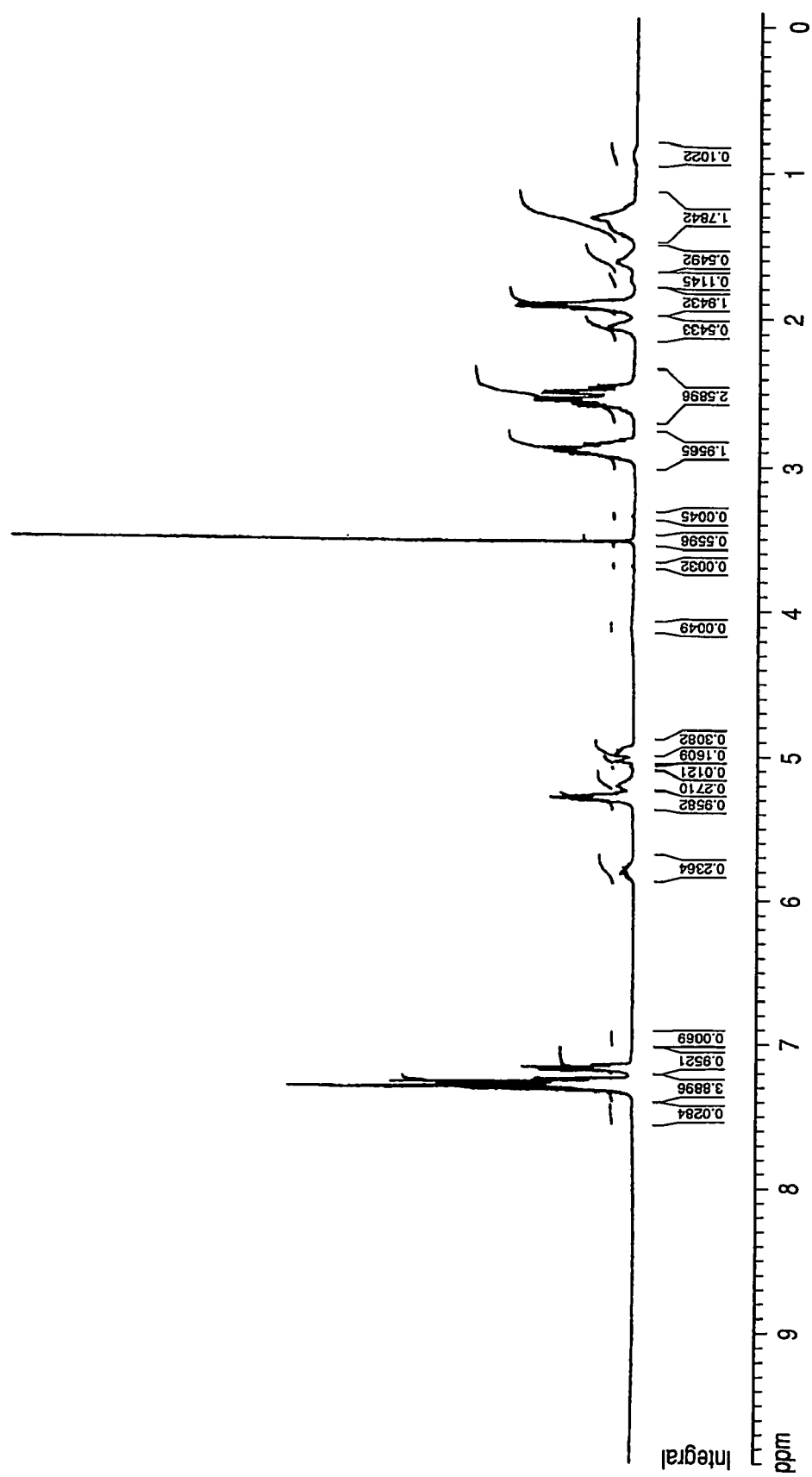
FIG. 3 is a $^1$H-NMR spectrum of a polyhydroxy alkanoate copolymer obtained in Example 11, and including 3-hydroxy-5-(phenylsulfanyl)valeric acid represented by a chemical formula (58), a 3-hydroxy-10-undecenoic acid represented by a chemical formula (5), 3-hydroxy-8-noneic acid represented by a chemical formula (6) and 3-hydroxy-6-heptenic acid represented by a chemical formula (7).

A structure of the obtained PHA was determined by a NMR analysis as in Example 1. An obtained $^1$H-NMR spectrum is shown in FIG. 3.

As a result, there was confirmed a polyhydroxy alkanoate copolymer including, as monomer units, 3-hydroxy-5-(phenylsulfanyl)valeric acid represented by the following chemical formula (58), 3-hydroxy-10-undecenoic acid represented by a chemical formula (5), 3-hydroxy-8-nonenoic acid represented by a chemical formula (6) and 3-hydroxy-6-heptenoic acid represented by a chemical formula (7).

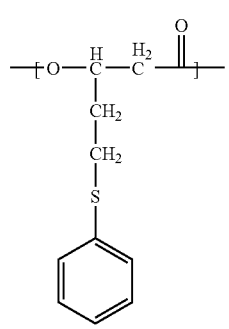
(58)

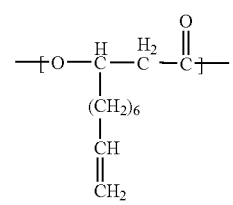
(5)

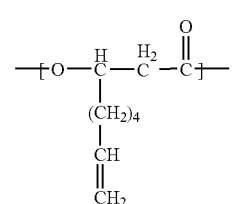
(6)

-continued

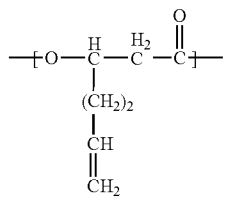
(7)

Also a proportion of such units was confirmed by $^1$H-NMR spectrum, where 3-hydroxy-5-(phenylsulfanyl)valeric acid was present by 78 mol %, a sum of three units of 3-hydroxy-10-undecenoic acid, 3-hydroxy-8-nonenoic acid and 3-hydroxy-6-heptenoic acid by 19 mol %, and others (linear 3-hydroxyalkanoic acid of 4 to 12 carbon atoms and 3-hydroxyalk-5-enoic acid with 10 or 12 carbon atoms) by 3 mol %.

The polyhydroxy alkanoate thus obtained was utilized in the following reaction. 302 mg of polyhydroxy alkanoate were charged in a 200-ml eggplant-shaped flask and were dissolved by adding 20 ml of dichloromethane. The solution was placed in an iced bath, and 3 ml of acetic acid and 1154 mg of 18-crown-6-ether were added and agitated. Then, in an iced bath, 917 mg of potassium permanganate were slowly added and an agitation was carried out for 19 hours at the room temperature. After the reaction, 50 ml of water and 3010 mg of sodium bisulfite were added. Then the liquid was brought to pH=1 by 1.0 N hydrochloric acid. After dichloromethane in the mixed solvent was distilled off in an evaporator, a polymer in the solution was recovered. The polymer was recovered by washing with 100 ml of methanol and washing three times with 100 ml of purified water. A drying under a reduced pressure provided 311 mg of the desired PHA.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=62000 and a weight-averaged molecular weight Mw=260000.

Figure 4:
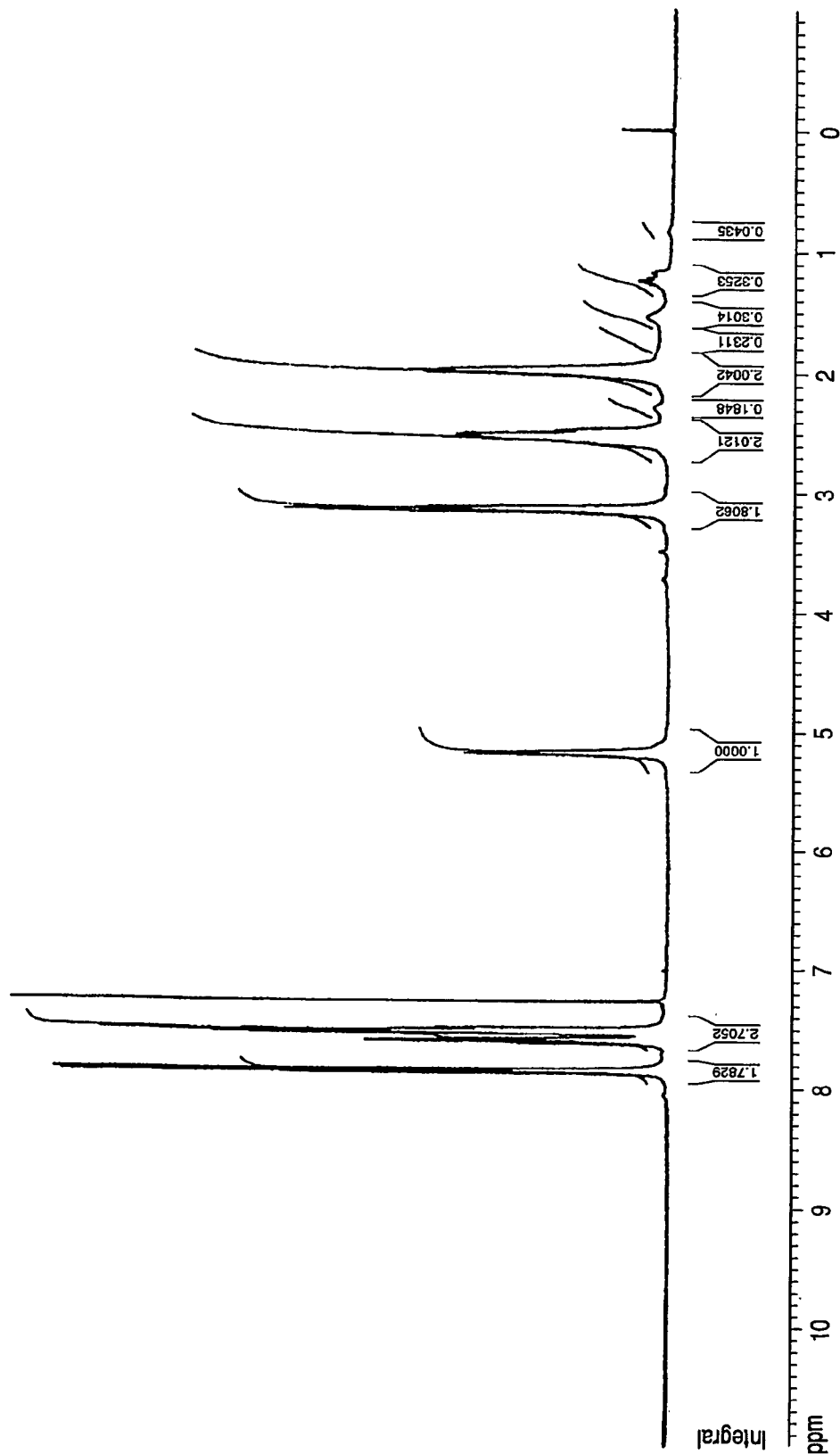
FIG. 4 is a $^1$H-NMR spectrum of a polyhydroxy alkanoate copolymer obtained in Example 11, and including 3-hydroxy-5-(phenylsulfonyl)valeric acid represented by a chemical formula (59), a 3-hydroxy-9-carboxynonanoic acid represented by a chemical formula (54), 3-hydroxy-7-carboxyheptanoic acid represented by a chemical formula (55) and 3-hydroxy-5-carboxyvaleric acid represented by a chemical formula (56).

For specifying the structure of the obtained PHA, a NMR analysis was carried out under conditions same as in Example 1. An obtained $^1$H-NMR spectrum is shown in FIG. 4.

As a result, there was confirmed a polyhydroxy alkanoate copolymer including, as monomer units, 3-hydroxy-5-(phenylsulfonyl)valeric acid represented by the following chemical formula (59), 3-hydroxy-9-carboxynonanoic acid represented by a chemical formula (54), 3-hydroxy-7-carboxyheptanoic acid represented by a chemical formula (55) and 3-hydroxy-5-carboxyvaleric acid represented by a chemical formula (56).

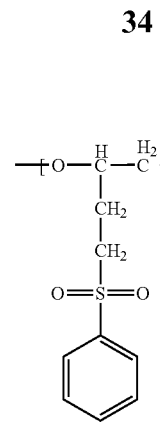
(59)

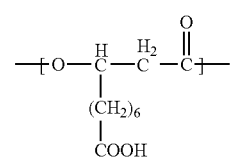
(54)

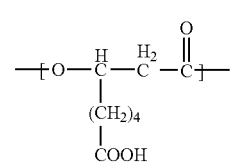
(55)

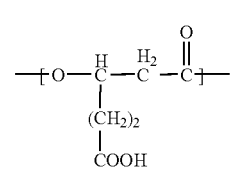
(56)

Also a proportion of the units of the obtained PHA was calculated by a methylesterification, utilizing trimethylsilyldiazomethane, of a carboxyl group at an end of a side chain of the PHA.

30 mg of the object PHA were charged in a 100-ml eggplant-shaped flask and were dissolved by adding 2.1 ml of chloroform and 0.7 ml of methanol. The solution was added with 0.5 ml of a 2 mol/L solution of trimethylsilyldiazomethane in hexane (supplied by Aldrich Inc.) and was agitated for 30 minutes at the room temperature. After the reaction, the solvent was distilled off in an evaporator to recover a polymer. The polymer was recovered by washing with 50 ml of methanol. A drying under a reduced pressure provided 31 mg of PHA.

A NMR analysis was carried out as in Example 1. As a result, $^1$H-NMR spectrum confirmed a proportion of the units in which 3-hydroxy-5-(phenylsulfonyl)valeric acid was present by 89 mol %, a sum of three units of 3-hydroxy-9-carboxynonanoic acid, 3-hydroxy-7-carboxyheptanoic acid and 3-hydroxy-5-carboxyvaleric acid by 8 mol %, and others (linear 3-hydroxyalkanoic acid of 4 to 12 carbon atoms and 3-hydroxyalk-5-enoic acid with 10 or 12 carbon atoms) by 3 mol %.

Example 12

There were prepared three 2000-ml shake flasks, and, in each, 0.5 wt. % of polypeptone (supplied by Wako Pure Chemical Co.), 6 mmol/L of 5-phenylvaleric acid, and 1.5 mmol/L of 10-undecenoic acid were dissolved in 1000 ml of an aforementioned M9 culture medium, which was placed in a 2000 ml shake flask, then sterilized in an autoclave and cooled to the room temperature. Then 10 ml of a culture liquid of *Pseudomonas cichorii* YN2 strain, shake cultured in advance in an M9 culture medium containing 0.5% of polypeptone for 8 hours, was added to each prepared culture medium, and culture was conducted for 60 hours at 30° C. After the culture, the culture liquids were united, and the cells were recovered by centrifuging, rinsed with methanol and dried. The dried cells, after weighing, were agitated with chloroform for 72 hours at 35° C. to extract a polymer. The chloroform extract was filtered with a 0.45 µm membrane filter, then concentrated in an evaporator, and the polymer was recovered by a reprecipitation in cold methanol. A desired polymer was then obtained by drying under a reduced pressure.

According to a weighing of the obtained polymer, 1533 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=72000 and a weight-averaged molecular weight Mw=170000.

A structure of the obtained PHA was determined by a NMR analysis as in Example 1.

As a result, there was confirmed a polyhydroxy alkanoate copolymer including, as monomer units, 3-hydroxy-5-phenylvaleric acid represented by the following chemical formula (60), 3-hydroxy-10-undecenoic acid represented by a chemical formula (5), 3-hydroxy-8-nonenoic acid represented by a chemical formula (6) and 3-hydroxy-6-heptenoic acid represented by a chemical formula (7).

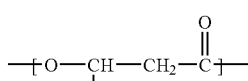

(60)

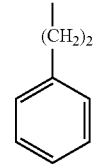

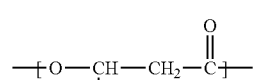

(5)

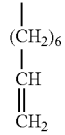

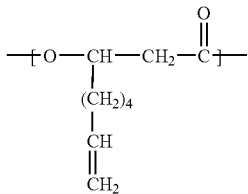

(6)

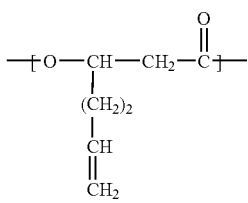

(7)

Also a proportion of such units was confirmed by $^1$H-NMR spectrum, where a sum of three units of 3-hydroxy-10-undecenoic acid, 3-hydroxy-8-nonenoic acid and 3-hydroxy-6-heptenoic acid was present by 12 mol %, 3-hydroxy-5-phenylvaleric acid by 85 mol % and others (linear 3-hydroxyalkanoic acid of 4 to 12 carbon atoms and 3-hydroxyalk-5-enoic acid with 10 or 12 carbon atoms) by 3 mol %.

The polyhydroxy alkanoate thus obtained was utilized in the following reaction.

1002 mg of polyhydroxy alkanoate were charged in a 500-ml eggplant-shaped flask and were dissolved by adding 60 ml of dichloromethane. The solution was placed in an iced bath, and 10 ml of acetic acid and 537 mg of 18-crown-6-ether were added and agitated. Then, in an iced bath, 429 mg of potassium permanganate were slowly added and an agitation was carried out for 2 hours in an iced bath and 18 hours at the room temperature. After the reaction, 40 ml of ethyl acetate, 30 ml of water and 1000 mg of sodium bisulfite were added. Then the liquid was brought to pH=1 by 1.0 N hydrochloric acid. A polymer was recovered by extraction followed by distilling off of the solvent. The polymer was recovered by washing with 300 ml of purified water, then with 200 ml of methanol, three times with 200 ml of purified water and finally with 200 ml of methanol. The obtained polymer was dissolved in 10 ml of tetrahydrofuran and dialyzed for 1 day with a dialysis film (manufactured by Spectrum Inc., Stectra/Por Standard Regenerated Cellulose Dialysis Membrane 3), in a 1-L beaker containing 500 ml of methanol. The polymer present in the dialysis film was recovered and dried under a reduced pressure to obtain 953 mg of a desired PHA.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=43000 and a weight-averaged molecular weight Mw=94000.

For specifying the structure of the obtained PHA, a NMR analysis was carried out under conditions same as in Example 1.

As a result, there was confirmed a polyhydroxy alkanoate copolymer including, as monomer units, 3-hydroxy-5-phenylvaleric acid represented by the following chemical formula (60), 3-hydroxy-9-carboxynonanoic acid represented by a chemical formula (54), 3-hydroxy-7-carboxyheptanoic acid represented by a chemical formula (55) and 3-hydroxy-5-carboxyvaleric acid represented by a chemical formula (56).

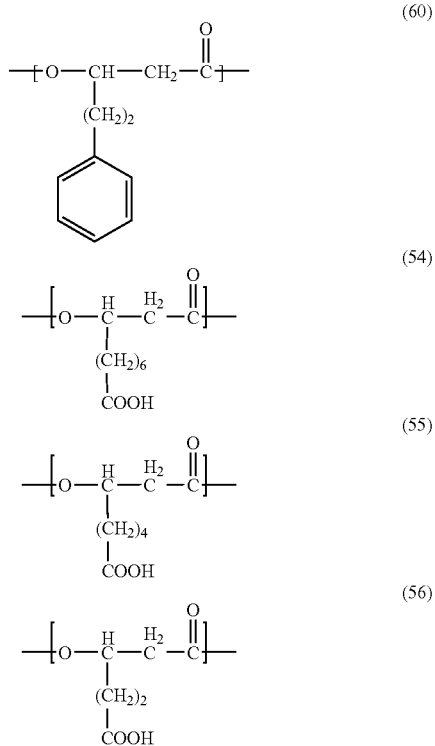

Also a proportion of the units of the obtained PHA was calculated by a. methylesterification, utilizing trimethylsilyl-diazomethane, of a carboxyl group at an end of a side chain of the PHA.

30 mg of the object PHA were charged in a 100-ml eggplant-shaped flask and were dissolved by adding 2.1 ml of chloroform and 0.7 ml of methanol. The solution was added with 0.5 ml of a 2 mol/L solution of trimethylsilyldiazomethane in hexane (supplied by Aldrich Inc.) and was agitated for 30 minutes at the room temperature. After the reaction, the solvent was distilled off in an evaporator to recover a polymer. The polymer was recovered by washing with 50 ml of methanol. Drying under a reduced pressure provided 30 mg of PHA.

A NMR analysis was carried out as in Example 1. As a result, $^1$H-NMR spectrum confirmed a proportion of the units in which 3-hydroxy-5-phenylvaleric acid was present by 86 mol %, a sum of three units of 3-hydroxy-9-carboxynonanoic acid, 3-hydroxy-7-carboxyheptanoic acid and 3-hydroxy-5-carboxyvaleric acid by 9 mol %, and others (linear 3-hydroxyalkanoic acid of 4 to 12 carbon atoms and 3-hydroxy-alk-5-enoic acid with 10 or 12 carbon atoms) by 5 mol %.

Example 13

500 mg of polyhydroxy alkanoate copolymer, including 3-hydroxy-5-phenylvaleric acid represented by the following chemical formula (60), 3-hydroxy-10-undecenoic acid represented by a chemical formula (5), 3-hydroxy-8-nonenoic acid represented by a chemical formula (6) and 3-hydroxy-6-heptenoic acid represented by a chemical formula (7) as monomer units used for the bacterial production in Example 12 were changed in a 500-ml three-necked flask, and were suspended by adding 150 ml of distilled water containing 50 ppm of hydrogen peroxide. Ozone was blown in with a rate of 50 mg/hr and the mixture was agitated for 3 hours at the room temperature.

After the reaction, the reaction liquid was filtered to recover a polymer. The polymer was resuspended in distilled water, and centrifuged to wash off remaining hydrogen peroxide. The obtained polymer was further dissolved in 5 ml of tetrahydrofuran and dialyzed for 1 day with a dialysis film (manufactured by Spectrum Inc., Stectra/Por Standard Regenerated Cellulose Dialysis Membrane 3), in a 300-ml beaker containing 250 ml of methanol. The polymer present in the dialysis film was recovered and dried under a reduced pressure to obtain 450 mg of a desired PHA.

An average molecular weight of the obtained PHA was measured by gel permeation chromatography (GPC: Tso HLC-8220 GPC, column: Toso TSK-GEL Super HM-H, solvent: chloroform, converted to polystyrene). As a result there were obtained a number-averaged molecular weight Mn=35000 and a weight-averaged molecular weight Mw=72000.

For specifying the structure of the obtained PHA, a NMR analysis was carried out under conditions same as in Example 1.

As a result, there was confirmed a polyhydroxy alkanoate copolymer including, as monomer units, 3-hydroxy-5-phenylvaleric acid represented by the following chemical formula (60), 3-hydroxy-9-carboxynonanoic acid represented by a chemical formula (54), 3-hydroxy-7-carboxyheptanoic acid represented by a chemical formula (55) and 3-hydroxy-5-carboxyvaleric acid represented by a chemical formula (56).

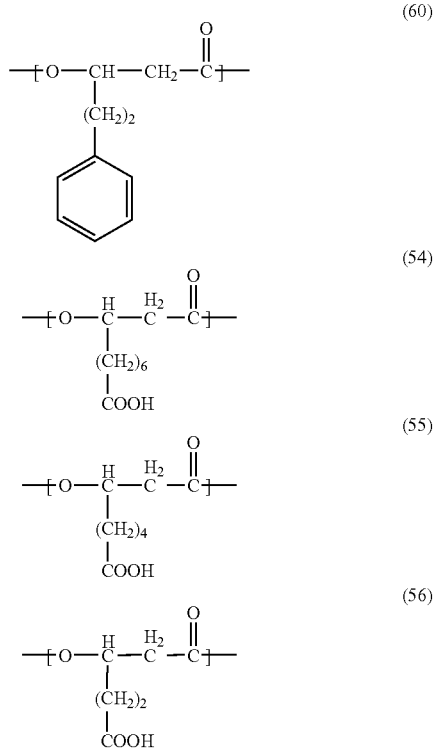

Also a proportion of the units of the obtained PHA was calculated by a methylesterification, utilizing trimethylsilyl-diazomethane, of a carboxyl group at an end of a side chain of the PHA.

30 mg of the object PHA were charged in a 100-ml egg-plant-shaped flask and were dissolved by adding 2.1 ml of chloroform and 0.7 ml of methanol. The solution was added with 0.3 ml of a 2 mol/L hexane solution of trimethylsilyl-diazomethane in hexane (supplied by Aldrich Inc.) and was agitated for 30 minutes at the room temperature. After the reaction, the solvent was distilled off in an evaporator to recover a polymer. The polymer was recovered by washing with 50 ml of methanol. A drying under a reduced pressure provided 30 mg of PHA.

A NMR analysis was carried out as in Example 1. As a result, there was confirmed a proportion of the units in which 3-hydroxy-5-phenylvaleric acid was present by 85 mol %, a sum of three units of 3-hydroxy-9-carboxynonanoic acid, 3-hydroxy-7-carboxyheptanoic acid and 3-hydroxy-5-carboxyvaleric acid by 10 mol %, and others (linear 3-hydroxyalkanoic acid of 4 to 12 carbon atoms and 3-hydroxyalk-5-enoic acid with 10 or 12 carbon atoms) by 5 mol %.

Example 14

There were prepared five 2000-ml shake flasks, and, in each, 0.5 wt. % of polypeptone (supplied by Wako Pure Chemical Co.), 6 mmol/L of 5-(4-vinylphenyl)valeric acid, and 1 mmol/L of 10-undecenoic acid were dissolved in 1000 ml of an aforementioned M9 culture medium, which was placed in a 2000 ml shake flask, then sterilized in an autoclave and cooled to the room temperature. Then 10 ml of a culture liquid of *Pseudomonas cichorii* YN2 strain, shake cultured in advance in an M9 culture medium containing 0.5% of polypeptone for 8 hours, was added to each prepared culture medium, and culture was conducted for 60 hours at 30° C. After the culture, the culture liquids were united, and the cells were recovered by centrifuging, rinsed with methanol and dried. The dried cells, after weighing, were agitated with chloroform for 72 hours at 25° C. to extract a polymer. The chloroform extract was filtered with a 0.45 μm membrane filter, then concentrated in an evaporator, and the polymer was recovered by a reprecipitation in cold methanol. A desired polymer was then obtained by drying under a reduced pressure.

According to a weighing of the obtained polymer, 1097 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=70000 and a weight-averaged molecular weight Mw=150000.

A structure of the obtained PHA was determined by a NMR analysis as in Example 1.

As a result, there was confirmed a polyhydroxy alkanoate copolymer including, as monomer units, 3-hydroxy-5-(4-vinylphenyl)valeric acid represented by the following chemical formula (61), 3-hydroxy-10-undecenoic acid represented by a chemical formula (5), 3-hydroxy-8-nonenoic acid represented by a chemical formula (6) and 3-hydroxy-6-heptenoic acid represented by a chemical formula (7).

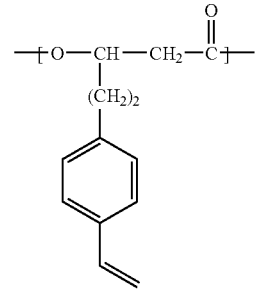

(61)

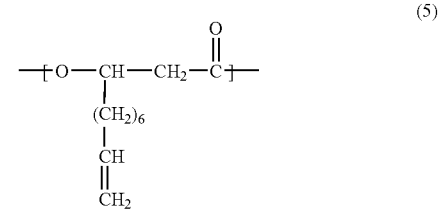

(5)

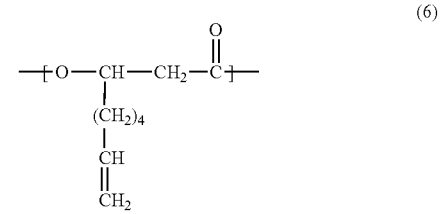

(6)

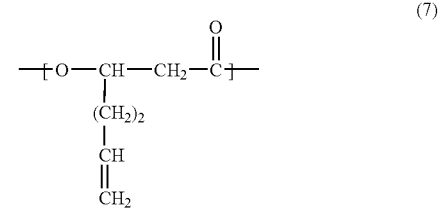

(7)

Also a proportion of such units was confirmed by $^1$H-NMR spectrum, where a sum of three units of 3-hydroxy-10-undecenoic acid, 3-hydroxy-8-nonenoic acid and 3-hydroxy-6-heptenoic acid was present by 9 mol %, 3-hydroxy-5-(4-vinylphenyl)valeric acid by 84 mol % and others (linear 3-hydroxyalkanoic acid of 4 to 12 carbon atoms and 3-hydroxyalk-5-enoic acid with 10 or 12 carbon atoms) by 7 mol %.

Example 15

There were prepared twenty 2000-ml shake flasks, and, in each, 0.5 wt. % of polypeptone (supplied by Wako Pure Chemical Co.), 6 mmol/L of 5-benzoylvaleric acid, and 1 mmol/L of 10-undecenoic acid were dissolved in 1000 ml of an aforementioned M9 culture medium, which was placed in a 2000 ml shake flask, then sterilized in an autoclave and cooled to the room temperature. Then 10 ml of a culture liquid of *Pseudomonas cichorii* YN2 strain, shake cultured in advance in an M9 culture medium containing 0.5% of polypeptone for 8 hours, was added to each prepared culture medium, and culture was conducted for 60 hours at 30° C. After the culture, the culture liquids were united, and the cells were recovered by centrifuging, rinsed with methanol and dried. The dried cells, after weighing, were agitated with chloroform for 72 hours at 25° C. to extract a polymer. The chloroform extract was filtered with a 0.45 μm membrane filter, then concentrated in an evaporator, and the polymer was recovered by a reprecipitation in cold methanol. A desired polymer was then obtained by drying under a reduced pressure.

According to a weighing of the obtained polymer, 1027 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=120000 and a weight-averaged molecular weight Mw=370000.

A structure of the obtained PHA was determined by a NMR analysis as in Example 1.

As a result, there was confirmed a polyhydroxy alkanoate copolymer including, as monomer units, 3-hydroxy-5-benzoylvaleric acid represented by the following chemical formula (62), 3-hydroxy-10-undecenoic acid represented by a chemical formula (5), 3-hydroxy-8-nonenoic acid represented by a chemical formula (6) and 3-hydroxy-6-heptenoic acid represented by a chemical formula (7).

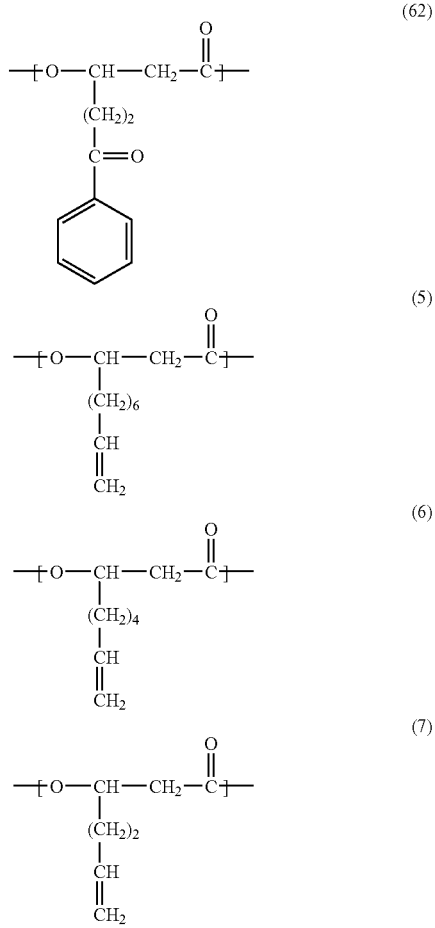

Also a proportion of such units was confirmed by $^1$H-NMR spectrum, where a sum of three units of 3-hydroxy-10-undecenoic acid, 3-hydroxy-8-nonenoic acid and 3-hydroxy-6-heptenoic acid was present by 11 mol %, 3-hydroxy-5-benzoylvaleric acid by 82 mol % and others (linear 3-hydroxyalkanoic acid of 4 to 12 carbon atoms and 3-hydroxyalk-5-enoic acid with 10 or 12 carbon atoms) by 7 mol %.

The polyhydroxy alkanoate thus obtained was utilized in the following reaction.

1003 mg of polyhydroxy alkanoate were charged in a 500-ml eggplant-shaped flask and were dissolved by adding 60 ml of dichloromethane. The solution was placed in an iced bath, and 10 ml of acetic acid and 410 mg of 18-crown-6-ether were added and agitated. Then, in an iced bath, 327 mg of potassium permanganate were slowly-added and an agitation was carried out for 2 hours in an iced bath and 18 hours at the room temperature. After the reaction, 100 ml of water and 1000 mg of sodium bisulfite were added. Then the liquid was brought to pH=1 by 1.0 N hydrochloric acid. After dichloromethane in the mixed solvent was distilled off in an evaporator, a polymer in the solution was recovered. The polymer was recovered by washing with 200 ml of purified water, then with 200 ml of methanol, three times with 200 ml of purified water and finally with 200 ml of methanol. The obtained polymer was dissolved in 10 ml of tetrahydrofuran and dialyzed for 1 day with a dialysis film (manufactured by Spectrum Inc., Stectra/Por Standard Regenerated Cellulose Dialysis Membrane 3), in a 1-L beaker containing 500 ml of methanol. The polymer present in the dialysis film was recovered and dried under a reduced pressure to obtain 948 mg of a desired PHA.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=76000 and a weight-averaged molecular weight Mw=235000.

For specifying the structure of the obtained PHA, a NMR analysis was carried out under conditions same as in Example 1.

As a result, there was confirmed a polyhydroxy alkanoate copolymer including, as monomer units, 3-hydroxy-5-benzoylvaleric acid represented by the following chemical formula (62), 3-hydroxy-9-carboxynonanoic acid represented by a chemical formula (54), 3-hydroxy-7-carboxyheptanoic acid represented by a chemical formula (55) and 3-hydroxy-5-carboxyvaleric acid represented by a chemical formula (56).

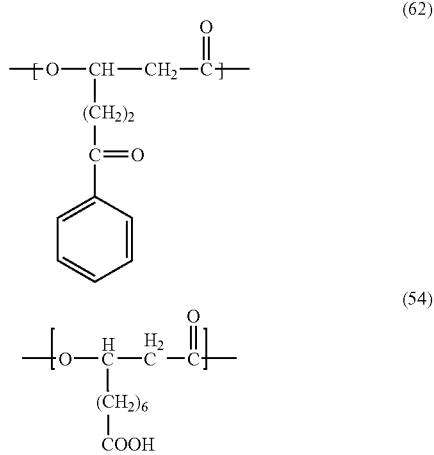

-continued

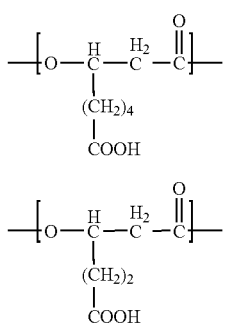

(55)

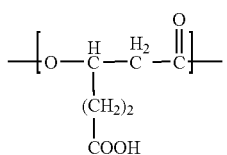

(56)

Also a proportion of the units of the obtained PHA was calculated by a methylesterification, utilizing trimethylsilyldiazomethane, of a carboxyl group at an end of a side chain of the PHA.

30 mg of the object PHA were charged in a 100-ml eggplant-shaped flask and were dissolved by adding 2.1 ml of chloroform and 0.7 ml of methanol. The solution was added with 0.3 ml of a 2.0 mol/L hexane solution of trimethylsilyldiazomethane in hexane (supplied by Aldrich Inc.) and was agitated for 30 minutes at the room temperature. After the reaction, the solvent was distilled off in an evaporator to recover a polymer. The polymer was recovered by washing with 50 ml of methanol. A drying under a reduced pressure provided 29 mg of PHA.

A NMR analysis was carried out as in Example 1. As a result, $^1$H-NMR spectrum confirmed a proportion of the units in which 3-hydroxy-5-benzoylvaleric acid was present by 84 mol %, a sum of three units of 3-hydroxy-9-carboxynonanoic acid, 3-hydroxy-7-carboxyheptanoic acid and 3-hydroxy-5-carboxyvaleric acid by 9 mol %, and others (linear 3-hydroxyalkanoic acid of 4 to 12 carbon atoms and 3-hydroxy-alk-5-enoic acid with 10 or 12 carbon atoms) by 7 mol %.

Example 16

There were prepared ten 2000-ml shake flasks, and, in each, 0.5 wt. % of polypeptone (supplied by Wako Pure Chemical Co.), 6 mmol/L of 5-[(phenylmethyl)sulfanyl]valeric acid, and 1.5 mmol/L of 10-undecenoic acid were dissolved in 1000 ml of an aforementioned M9 culture medium, which was placed in a 2000 ml shake flask, then sterilized in an autoclave and cooled to the room temperature. Then 10 ml of a culture liquid of Pseudomonas cichorii YN2 strain, shake cultured in advance in an M9 culture medium containing 0.5% of polypeptone for 8 hours, was added to each prepared culture medium, and culture was conducted for 60 hours at 30° C. After the culture, the culture liquids were united, and the cells were recovered by centrifuging, rinsed with methanol and dried. The dried cells, after weighing, were agitated with chloroform for 72 hours at 25° C. to extract a polymer. The chloroform extract was filtered with a 0.45 μm membrane filter, then concentrated in an evaporator, and the polymer was recovered by a reprecipitation in cold methanol. A desired polymer was then obtained by drying under a reduced pressure.

According to a weighing of the obtained polymer, 1714 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=110000 and a weight-averaged molecular weight Mw=380000.

For specifying the structure of the obtained PHA, a NMR analysis was conducted under conditions similar to those in Example 1.

As a result, there was confirmed a polyhydroxy alkanoate copolymer including, as monomer units, 3-hydroxy-5-[(phenylmethyl)sulfanyl]valeric acid represented by the following chemical formula (63), 3-hydroxy-10-undecenoic acid represented by a chemical formula (5), 3-hydroxy-8-nonenoic acid represented by a chemical formula (6) and 3-hydroxy-6-heptenoic acid represented by a chemical formula (7).

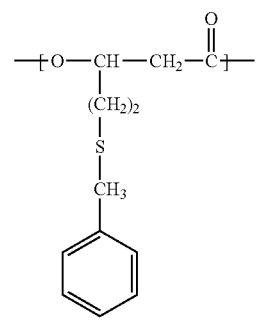

(63)

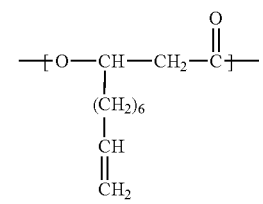

(5)

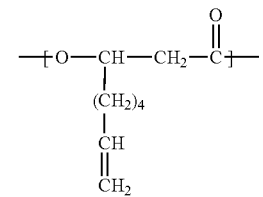

(6)

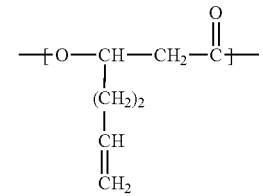

(7)

Also a proportion of such units was confirmed by $^1$H-NMR spectrum, where a sum of three units of 3-hydroxy-10-undecenoic acid, 3-hydroxy-8-nonenoic acid and 3-hydroxy-6-heptenoic acid was present by 12 mol %, 3-hydroxy-5-[(phenylmethyl)sulfanyl]valeric acid by 80 mol % and others (linear 3-hydroxyalkanoic acid of 4 to 12 carbon atoms and 3-hydroxyalk-5-enoic acid with 10 or 12 carbon atoms) by 8 mol %.

Example 17

There were prepared three 2000-ml shake flasks, and, in each, 0.5 wt. % of polypeptone (supplied by Wako Pure Chemical Co.), 6 mmol/L of 5-(2-thienyl)valeric acid, and 1.5 mmol/L of 10-undecenoic acid were dissolved in 1000 ml of an aforementioned M9 culture medium, which was placed in a 2000 ml shake flask, then sterilized in an autoclave and cooled to the room temperature. Then 10 ml of a culture liquid of *Pseudomonas cichorii* YN2 strain, shake cultured in advance in an M9 culture medium containing 0.5% of polypeptone for 8 hours, was added to each prepared culture medium, and culture was conducted for 60 hours at 30° C. After the culture, the culture liquids were united, and the cells were recovered by centrifuging, rinsed with methanol and dried. The dried cells, after weighing, were agitated with chloroform for 72 hours at 25° C. to extract a polymer. The chloroform extract was filtered with a 0.45 μm membrane filter, then concentrated in an evaporator, and the polymer was recovered by a reprecipitation in cold methanol. A desired polymer was then obtained by drying under a reduced pressure.

According to a weighing of the obtained polymer, 1171 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=74000 and a weight-averaged molecular weight Mw=180000.

For specifying the structure of the obtained PHA, a NMR analysis was conducted under conditions similar to those in Example 1.

As a result, there was confirmed a polyhydroxy alkanoate copolymer including, as monomer units, 3-hydroxy-5-(2-thienyl)valeric acid represented by the following chemical formula (64), 3-hydroxy-10-undecenoic acid represented by a chemical formula (5), 3-hydroxy-8-nonenoic acid represented by a chemical formula (6) and 3-hydroxy-6-heptenoic acid represented by a chemical formula (7).

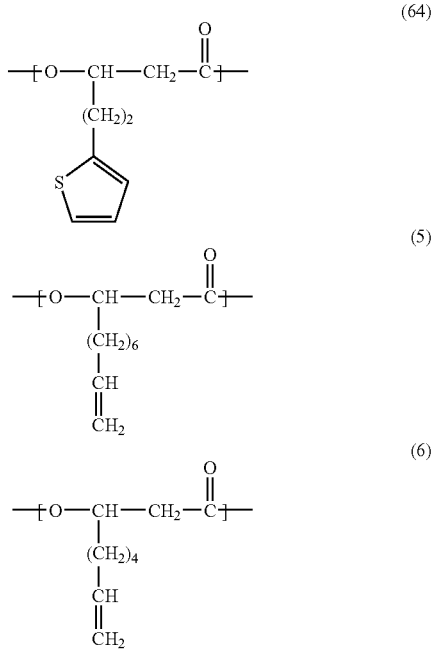

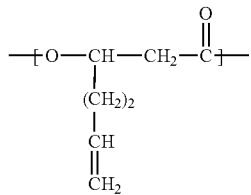

Also a proportion of such units was confirmed by $^1$H-NMR spectrum, where a sum of three units of 3-hydroxy-10-undecenoic acid, 3-hydroxy-8-nonenoic acid and 3-hydroxy-6-heptenoic acid was present by 12 mol %, 3-hydroxy-5-(2-thienyl)valeric acid by 85 mol % and others (linear 3-hydroxyalkanoic acid of 4 to 12 carbon atoms and 3-hydroxyalk-5-enoic acid with 10 or 12 carbon atoms) by 3 mol %.

The polyhydroxy alkanoate thus obtained was utilized in the following reaction.

1001 mg of polyhydroxy alkanoate were charged in a 500-ml eggplant-shaped flask and were dissolved by adding 60 ml of dichloromethane. The solution was placed in an iced bath, and 10 ml of acetic acid and 527 mg of 18-crown-6-ether were added and agitated. Then, in an iced bath, 420 mg of potassium permanganate were slowly added and an agitation was carried out for 2 hours in an iced bath and 18 hours at the room temperature. After the reaction, 100 ml of water and 1000 mg of sodium bisulfite were added. Then the liquid was brought to pH=1 by 1.0 N hydrochloric acid. After dichloromethane in the mixed solvent was distilled off in an evaporator, a polymer in the solution was recovered. The polymer was recovered by washing with 200 ml of purified water, then with 200 ml of methanol, three times with 200 ml of purified water and finally with 200 ml of methanol. The obtained polymer was dissolved in 10 ml of tetrahydrofuran and dialyzed for 1 day with a dialysis film (manufactured by Spectrum Inc., Stectra/Por Standard Regenerated Cellulose Dialysis Membrane 3), in a 1-L beaker containing 500 ml of methanol. The polymer present in the dialysis film was recovered and dried under a reduced pressure to obtain 946 mg of a desired PHA.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=45000 and a weight-averaged molecular weight Mw=95000.

For specifying the structure of the obtained PHA, a NMR analysis was carried out under conditions same as in Example 1.

As a result, there was confirmed a polyhydroxy alkanoate copolymer including, as monomer units, 3-hydroxy-5-(2-thienyl)valeric acid represented by the following chemical formula (64), 3-hydroxy-9-carboxynonanoic acid represented by a chemical formula (54), 3-hydroxy-7-carboxyheptanoic acid represented by a chemical formula (55) and 3-hydroxy-5-carboxyvaleric acid represented by a chemical formula (56).

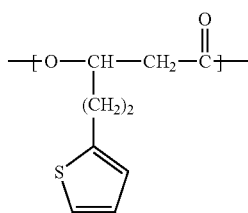
(64)

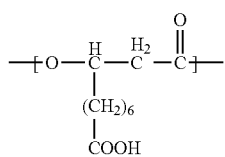
(54)

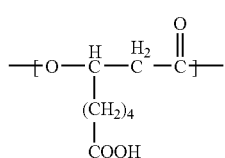
(55)

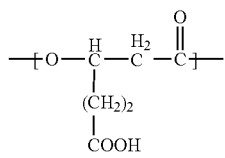
(56)

Also a proportion of the units of the obtained PHA was calculated by a methylesterification, utilizing trimethylsilyldiazomethane, of a carboxyl group at an end of a side chain of the PHA.

30 mg of the object PHA were charged in a 100-ml eggplant-shaped flask and were dissolved by adding 2.1 ml of chloroform and 0.7 ml of methanol. The solution was added with 0.3 ml of a 2.0 mol/L solution of trimethylsilyldiazomethane in hexane (supplied by Aldrich Inc.) and was agitated for 30 minutes at the room temperature. After the reaction, the solvent was distilled off in an evaporator to recover a polymer. The polymer was recovered by washing with 50 ml of methanol. A drying under a reduced pressure provided 30 mg of PHA.

A NMR analysis was carried out as in Example 1. As a result, $^1$H-NMR spectrum confirmed a proportion of the units in which 3-hydroxy-5-(2-thienyl)valeric acid was present by 85 mol %, a sum of three units of 3-hydroxy-9-carboxynonanoic acid, 3-hydroxy-7-carboxyheptanoic acid and 3-hydroxy-5-carboxyvaleric acid by 10 mol %, and others (linear 3-hydroxyalkanoic acid of 4 to 12 carbon atoms and 3-hydroxyalk-5-enoic acid with 10 or 12 carbon atoms) by 5 mol %.

Example 18

There were prepared three 2000-ml shake flasks, and, in each, 0.5 wt. % of polypeptone (supplied by Wako Pure Chemical Co.), 6 mmol/L of 5-(2-thienylsulfanyl)valeric acid, and 1 mmol/L of 10-undecenoic acid were dissolved in 1000 ml of an aforementioned M9 culture medium, which was placed in a 2000 ml shake flask, then sterilized in an autoclave and cooled to the room temperature. Then 10 ml of a culture liquid of *Pseudomonas cichorii* YN2 strain, shake cultured in advance in an M9 culture medium containing 0.5% of polypeptone for 8 hours, was added to each prepared culture medium, and culture was conducted for 60 hours at 30° C. After the culture, the culture liquids were united, and the cells were recovered by centrifuging, rinsed with methanol and dried. The dried cells, after weighing, were agitated with chloroform for 72 hours at 25° C. to extract a polymer. The chloroform extract was filtered with a 0.45 μm membrane filter, then concentrated in an evaporator, and the polymer was recovered by a reprecipitation in cold methanol. A desired polymer was then obtained by drying under a reduced pressure.

According to a weighing of the obtained polymer, 1257 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=68000 and a weight-averaged molecular weight Mw=160000.

For specifying the structure of the obtained PHA, a NMR analysis was conducted under conditions same as in Example 1.

As a result, there was confirmed a polyhydroxy alkanoate copolymer including, as monomer units, 3-hydroxy-5-(2-thienylsulfanyl)valeric acid represented by the following chemical formula (65), 3-hydroxy-10-undecenoic acid represented by a chemical formula (5), 3-hydroxy-8-nonenoic acid represented by a chemical formula (6) and 3-hydroxy-6-heptenoic acid represented by a chemical formula (7).

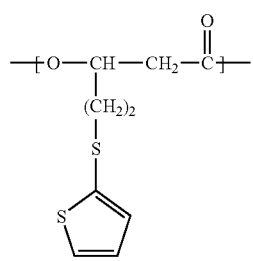
(65)

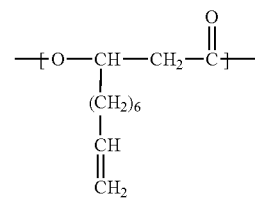
(5)

-continued

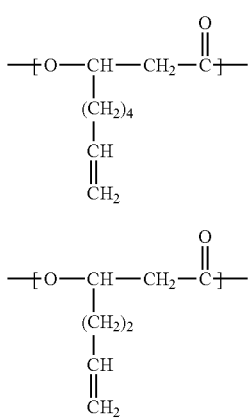

Also a proportion of such units was confirmed by $^1$H-NMR spectrum, where a sum of three units of 3-hydroxy-10-undecenoic acid, 3-hydroxy-8-nonenoic acid and 3-hydroxy-6-heptenoic acid was present by 9 mol %, 3-hydroxy-5-(2-thienylsulfanyl)valeric acid by 84 mol % and others (linear 3-hydroxyalkanoic acid of 4 to 12 carbon atoms and 3-hydroxyalk-5-enoic acid with 10 or 12 carbon atoms) by 7 mol %.

Example 19

There were prepared ten 2000-ml shake flasks, and, in each, 0.5 wt. % of polypeptone (supplied by Wako Pure Chemical Co.), 6 mmol/L of 5-(2-thienylcarbonyl)valeric acid, and 1 mmol/L of 10-undecenoic acid were dissolved in 1000 ml of an aforementioned M9 culture medium, which was placed in a 2000 ml shake flask, then sterilized in an autoclave and cooled to the room temperature. Then 10 ml of a culture liquid of *Pseudomonas cichorii* YN2 strain, shake cultured in advance in an M9 culture medium containing 0.5% of polypeptone for 8 hours, was added to each prepared culture medium, and culture was conducted for 60 hours at 30° C. After the culture, the culture liquids were united, and the cells were recovered by centrifuging, rinsed with methanol and dried. The dried cells, after weighing, were agitated with chloroform for 72 hours at 25° C. to extract a polymer. The chloroform extract was filtered with a 0.45 μm membrane filter, then concentrated in an evaporator, and the polymer was recovered by a reprecipitation in cold methanol. A desired polymer was then obtained by drying under a reduced pressure.

According to a weighing of the obtained polymer, 1251 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=75000 and a weight-averaged molecular weight Mw=180000.

For specifying the structure of the obtained PHA, a NMR analysis was conducted under conditions similar to those in Example 1.

As a result, there was confirmed a polyhydroxy alkanoate copolymer including, as monomer units, 3-hydroxy-5-(2-thienylcarbonyl)valeric acid represented by the following chemical formula (66), 3-hydroxy-10-undecenoic acid represented by a chemical formula (5), 3-hydroxy-8-nonenoic acid represented by a chemical formula (6) and 3-hydroxy-6-heptenoic acid represented by a chemical formula (7).

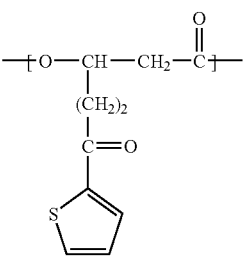

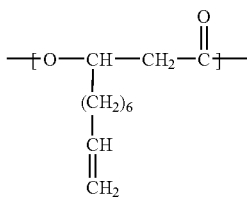

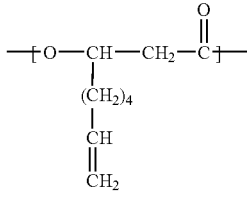

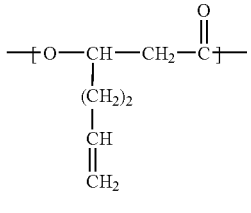

Also a proportion of such units was confirmed by $^1$H-NMR spectrum, where a sum of three units of 3-hydroxy-10-undecenoic acid, 3-hydroxy-8-nonenoic acid and 3-hydroxy-6-heptenoic acid was present by 10 mol %, 3-hydroxy-5-(2-thienylcarbonyl)valeric acid by 81 mol % and others (linear 3-hydroxyalkanoic acid of 4 to 12 carbon atoms and 3-hydroxyalk-5-enoic acid with 10 or 12 carbon atoms) by 9 mol %.

The polyhydroxy alkanoate thus obtained was utilized in the following reaction.

999 mg of polyhydroxy alkanoate were charged in a 500-ml eggplant-shaped flask and were dissolved by adding 60 ml of dichloromethane. The solution was placed in an iced bath, and 10 ml of acetic acid and 382 mg of 18-crown-6-ether were added and agitated. Then, in an iced bath, 304 mg of potassium permanganate were slowly added and an agitation was carried out for 2 hours in an iced bath and 18 hours at the room temperature. After the reaction, 100 ml of water and 1000 mg of sodium bisulfite were added. Then the liquid was brought to pH=1 by 1.0 N hydrochloric acid. After dichloromethane in the mixed solvent was distilled off in an evaporator, a polymer in the solution was recovered. The polymer was recovered by washing with 200 ml of purified water, then with 200 ml of methanol, three times with 200 ml of purified water and finally with 200 ml of methanol. The obtained polymer was dissolved in 10 ml of tetrahydrofuran and dialyzed for 1 day with a dialysis film (manufactured by Spectrum Inc., Stectra/Por Standard Regenerated Cellulose Dialysis Membrane 3), in a 1-L beaker containing 500 ml of methanol. The polymer present in the dialysis film was recovered and dried under a reduced pressure to obtain 935 mg of a desired PHA.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=45000 and a weight-averaged molecular weight Mw=99000.

For specifying the structure of the obtained PHA, a NMR analysis was carried out under conditions same as in Example 1.

As a result, there was confirmed a polyhydroxy alkanoate copolymer including, as monomer units, 3-hydroxy-5-(2-thienylcarbonyl)valeric acid represented by the following chemical formula (66), 3-hydroxy-9-carboxynonanoic acid represented by a chemical formula (54), 3-hydroxy-7-carboxyheptanoic acid represented by a chemical formula (55) and 3-hydroxy-5-carboxyvaleric acid represented by a chemical formula (56).

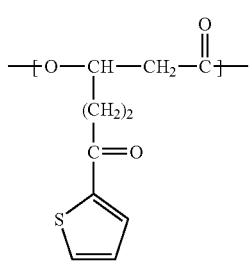

(66)

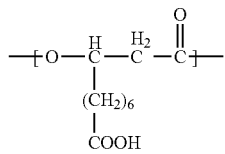

(54)

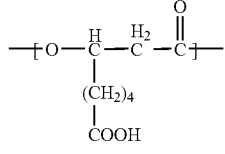

(55)

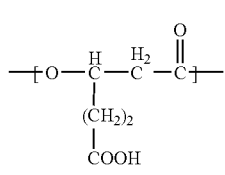

(56)

Also a proportion of the units of the obtained PHA was calculated by a methylesterification, utilizing trimethylsilyldiazomethane, of a carboxyl group at an end of a side chain of the PHA.

31 mg of the object PHA were charged in a 100-ml eggplant-shaped flask and were dissolved by adding 2.1 ml of chloroform and 0.7 ml of methanol. The solution was added with 0.3 ml of a 2.0 mol/L solution of trimethylsilyldiazomethane in hexane (supplied by Aldrich Inc.) and was agitated for 30 minutes at the room temperature. After the reaction, the solvent was distilled off in an evaporator to recover a polymer. The polymer was recovered by washing with 50 ml of methanol. A drying under a reduced pressure provided 30 mg of PHA.

A NMR analysis was carried out as in Example 1. As a result, $^1$H-NMR spectrum confirmed a proportion of the units in which 3-hydroxy-5-(2-thienylcarbonyl)valeric acid was present by 83 mol %, a sum of three units of 3-hydroxy-9-carboxynonanoic acid, 3-hydroxy-7-carboxyheptanoic acid and 3-hydroxy-5-carboxyvaleric acid by 7 mol %, and others (linear 3-hydroxyalkanoic acid of 4 to 12 carbon atoms and 3-hydroxyalk-5-enoic acid with 10 or 12 carbon atoms) by 10 mol %.

Example 20

There were prepared fifteen 2000-ml shake flasks, and, in each, 0.5 wt. % of polypeptone (supplied by Wako Pure Chemical Co.), 6 mmol/L of 5-[(phenylmethyl)oxy]valeric acid, and 1 mmol/L of 10-undecenoic acid were dissolved in 1000 ml of an aforementioned M9 culture medium, which was placed in a 2000 ml shake flask, then sterilized in an autoclave and cooled to the room temperature. Then 10 ml of a culture liquid of *Pseudomonas cichorii* YN2 strain, shake cultured in advance in an M9 culture medium containing 0.5% of polypeptone for 8 hours, was added to each prepared culture medium, and culture was conducted for 60 hours at 30° C. After the culture, the culture liquids were united, and the cells were recovered by centrifuging, rinsed with methanol and dried. The dried cells, after weighing, were agitated with chloroform for 72 hours at 25° C. to extract a polymer. The chloroform extract was filtered with a 0.45 μm membrane filter, then concentrated in an evaporator, and the polymer was recovered by a reprecipitation in cold methanol. A desired polymer was then obtained by drying under a reduced pressure.

According to a weighing of the obtained polymer, 1348 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=79000 and a weight-averaged molecular weight Mw=190000.

For specifying the structure of the obtained PHA, a NMR analysis was conducted under conditions similar to those in Example 1.

As a result, there was confirmed a polyhydroxy alkanoate copolymer including, as monomer units, 3-hydroxy-5-[(phenylmethyl)oxy]valeric acid represented by the following chemical formula (67), 3-hydroxy-10-undecenoic acid represented by a chemical formula (5), 3-hydroxy-8-nonenoic acid represented by a chemical formula (6) and 3-hydroxy-6-heptenoic acid represented by a chemical formula (7).

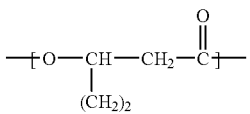
(67)

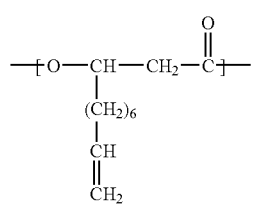
(5)

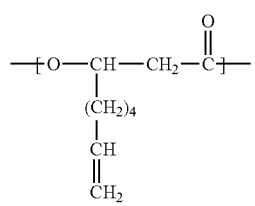
(6)

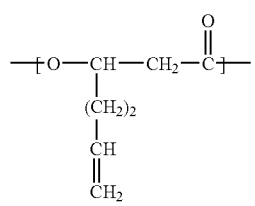
(7)

Also a proportion of 'such units was confirmed by $^1$H-NMR spectrum, where a sum of three units of 3-hydroxy-10-undecenoic acid, 3-hydroxy-8-nonenoic acid and 3-hydroxy-6-heptenoic acid was present by 10 mol %, 3-hydroxy-5-[(phenylmethyl)oxy]valeric acid by 82 mol % and others (linear 3-hydroxyalkanoic acid of 4 to 12 carbon atoms and 3-hydroxyalk-5-enoic acid with 10 or 12 carbon atoms) by 8 mol %.

The polyhydroxy alkanoate thus obtained was utilized in the following reaction.

1004 mg of polyhydroxy alkanoate were charged in a 500-ml eggplant-shaped flask and were dissolved by adding 60 ml of dichloromethane. The solution was placed in an iced bath, and 10 ml of acetic acid and 389 mg of 18-crown-6-ether were added and agitated. Then, in an iced bath, 310 mg of potassium permanganate were slowly added and an agitation was carried out for 2 hours in an iced bath and 18 hours at the room temperature. After the reaction, 100 ml of water and 1000 mg of sodium bisulfite were added. Then the liquid was brought to pH=1 by 1.0 N hydrochloric acid. After dichloromethane in the mixed solvent was distilled off in an evaporator, a polymer in the solution was recovered. The polymer was recovered by washing with 200 ml of purified water, then with 200 ml of methanol, three times with 200 ml of purified water and finally with 200 ml of methanol. The obtained polymer was dissolved in 10 ml of tetrahydrofuran and dialyzed for 1 day with a dialysis film (manufactured by Spectrum Inc., Stectra/Por Standard Regenerated Cellulose Dialysis Membrane 3), in a 1-L beaker containing 500 ml of methanol. The polymer present in the dialysis film was recovered and dried under a reduced pressure to obtain 940 mg of a desired PHA.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=48000 and a weight-averaged molecular weight Mw=106000.

For specifying the structure of the obtained PHA, a NMR analysis was carried out under conditions same as in Example 1.

As a result, there was confirmed a polyhydroxy alkanoate copolymer including, as monomer units, 3-hydroxy-5-[(phenylmethyl)oxy]valeric acid represented by the following chemical formula (67), 3-hydroxy-9-carboxynonanoic acid represented by a chemical formula (54), 3-hydroxy-7-carboxyheptanoic acid represented by a chemical formula (55) and 3-hydroxy-5-carboxyvaleric acid represented by a chemical formula (56).

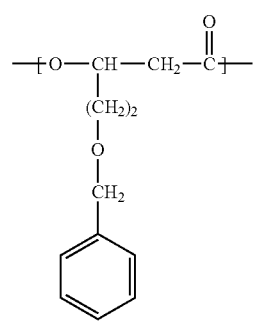
(67)

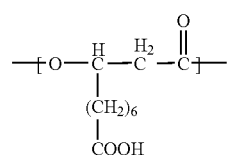
(54)

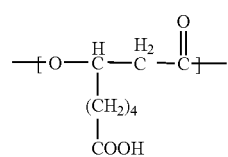
(55)

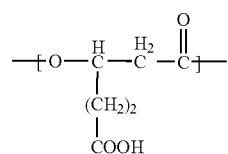
(56)

Also a proportion of the units of the obtained PHA was calculated by a methylesterification, utilizing trimethylsilyldiazomethane, of a carboxyl group at an end of a side chain of the PHA.

30 mg of the object PHA were charged in a 100-ml eggplant-shaped flask and were dissolved by adding 2.1 ml of chloroform and 0.7 ml of methanol. The solution was added with 0.3 ml of a 2.0 mol/L solution of trimethylsilyldiazomethane in hexane (supplied by Aldrich Inc.) and was agitated for 30 minutes at the room temperature. After the reaction, the solvent was distilled off in an evaporator to recover a polymer. The polymer was recovered by washing with 50 ml of methanol. A drying under a reduced pressure provided 29 mg of PHA.

A NMR analysis was carried out as in Example 1. As a result, $^1$H-NMR spectrum confirmed a proportion of the units in which 3-hydroxy-5-[(phenylmethyl)oxy]valeric acid was present by 84 mol %, a sum of three units of 3-hydroxy-9-carboxynonanoic acid, 3-hydroxy-7-carboxyheptanoic acid and 3-hydroxy-5-carboxyvaleric acid by 8 mol %, and others (linear 3-hydroxyalkanoic acid of 4 to 12 carbon atoms and 3-hydroxyalk-5-enoic acid with 10 or 12 carbon atoms) by 8 mol %.

Example 21

There were prepared five 2000-ml shake flasks, and, in each, 0.5 wt. % of polypeptone (supplied by Wako Pure Chemical Co.), 3 mmol/L of 5-phenoxyvaleric acid, 3 mmol/L of 5-cyclohexylvaleric acid and 1 mmol/L of 10-undecenoic. acid were dissolved in 1000 ml of an aforementioned M9 culture medium, which was placed in a 2000 ml shake flask, then sterilized in an autoclave and cooled to the room temperature. Then 10 ml of a culture liquid of *Pseudomonas cichorii* YN2 strain, shake cultured in advance in an M9 culture medium containing 0.5% of polypeptone for 8 hours, was added to each prepared culture medium, and culture was conducted for 60 hours at 30° C. After the culture, the culture liquids were united, and the cells were recovered by centrifuging, rinsed with methanol and dried. The dried cells, after weighing, were agitated with chloroform for 72 hours at 25° C. to extract a polymer. The chloroform extract was filtered with a 0.45 µm membrane filter, then concentrated in an evaporator, and the polymer was recovered by a reprecipitation in cold methanol. A desired polymer was then obtained by drying under a reduced pressure.

According to a weighing of the obtained polymer, 1285 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=86000 and a weight-averaged molecular weight Mw=230000.

For specifying the structure of the obtained PHA, a NMR analysis was conducted under conditions similar to those in Example 1.

As a result, there was confirmed a polyhydroxy alkanoate copolymer including, as monomer units, 3-hydroxy-5-phenoxyvaleric acid represented by the following chemical formula (53), 3-hydroxy-5-cyclohexylvaleric acid represented by the following chemical formula (68), 3-hydroxy-10-undecenoic acid represented by a chemical formula (5), 3-hydroxy-8-nonenoic acid represented by a chemical formula (6) and 3-hydroxy-6-heptenoic acid represented by a chemical formula (7).

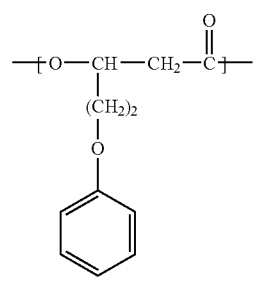

(53)

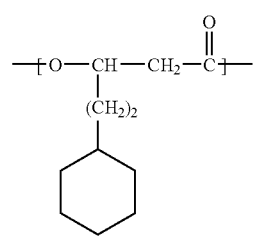

(68)

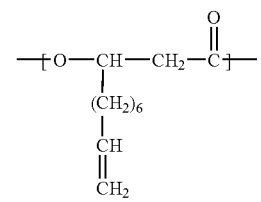

(5)

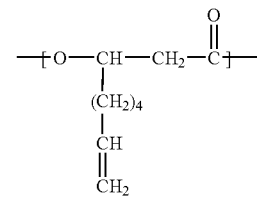

(6)

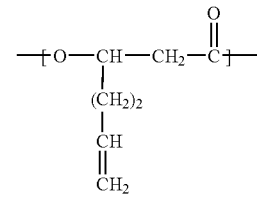

(7)

Also a proportion of such units was confirmed by $^1$H-NMR spectrum, where a sum of three units of 3-hydroxy-10-undecenoic acid, 3-hydroxy-8-nonenoic acid and 3-hydroxy-6-heptenoic acid was present by 7 mol %, 3-hydroxy-5-phenoxyvaleric acid by 48 mol %, 3-hydroxy-5-cyclohexylvaleric acid by 41 mol %, and others (linear 3-hydroxyalkanoic acid of 4 to 12 carbon atoms and 3-hydroxyalk-5-enoic acid with 10 or 12 carbon atoms) by 4 mol %.

The polyhydroxy alkanoate thus obtained was utilized in the following reaction.

1002 mg of polyhydroxy alkanoate were charged in a 500-ml eggplant-shaped flask and were dissolved by adding 60 ml of dichloromethane. The solution was placed in an iced bath, and 10 ml of acetic acid and 288 mg of 18-crown-6-ether were added and agitated. Then, in an iced bath, 230 mg of potassium permanganate were slowly added and an agitation was carried out for 2 hours in an iced bath and 18 hours at the room temperature. After the reaction, 100 ml of water and 1000 mg of sodium bisulfite were added. Then the liquid was brought to pH=1 by 1.0 N hydrochloric acid. After dichloromethane in the mixed solvent was distilled off in an evaporator, a polymer in the solution was recovered. The polymer was recovered by washing with 200 ml of purified water, then with 200 ml of methanol, three times with 200 ml of purified water and finally with 200 ml of methanol. The obtained polymer was dissolved in 10 ml of tetrahydrofuran and dialyzed for 1 day with a dialysis film (manufactured by Spectrum Inc., Stectra/Por Standard Regenerated Cellulose Dialysis Membrane 3), in a 1-L beaker containing 500 ml of methanol. The polymer present in the dialysis film was recovered and dried under a reduced pressure to obtain 967 mg of a desired PHA.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=51000 and a weight-averaged molecular weight Mw=108000.

For specifying the structure of the obtained PHA, a NMR analysis was carried out under conditions same as in Example 1.

As a result, there was confirmed a polyhydroxy alkanoate copolymer including, as monomer units, 3-hydroxy-5-phenoxyvaleric acid represented by the following chemical formula (53), 3-hydroxy-5-cyclohexylvaleric acid represented by the following chemical formula (68), 3-hydroxy-9-carboxynonanoic acid represented by a chemical formula (54), 3-hydroxy-7-carboxyheptanoic acid represented by a chemical formula (55) and 3-hydroxy-5-carboxyvaleric acid represented by a chemical formula (56).

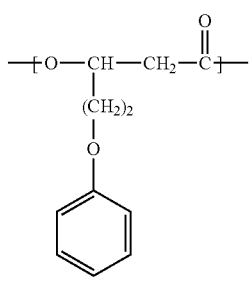

(53)

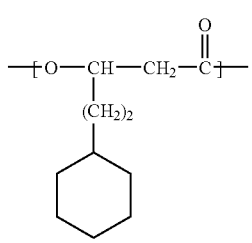

(68)

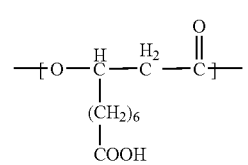

(54)

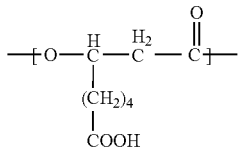

(55)

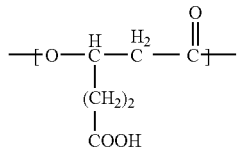

(56)

Also a proportion of the units of the obtained PHA was calculated by a methylesterification, utilizing trimethylsilyldiazomethane, of a carboxyl group at an end of a side chain of the PHA.

30 mg of the object PHA were charged in a 100-ml eggplant-shaped flask and were dissolved by adding 2.1 ml of chloroform and 0.7 ml of methanol. The solution was added with 0.3 ml of a 2.0 mol/L solution of trimethylsilyldiazomethane in hexane (supplied by Aldrich Inc.) and was agitated for 30 minutes at the room temperature. After the reaction, the solvent was distilled off in an evaporator to recover a polymer. The polymer was recovered by washing with 50 ml of methanol. A drying under a reduced pressure provided 28 mg of PHA.

A NMR analysis was carried out as in Example 1. As a result, $^1$H-NMR spectrum confirmed a proportion of the units in which 3-hydroxy-5-phenoxyvaleric acid was present by 49 mol %, 3-hydroxy-5-cyclohexylvaleric acid by 42 mol %, a sum of three units of 3-hydroxy-9-carboxynonanoic acid, 3-hydroxy-7-carboxyheptanoic acid and 3-hydroxy-5-carboxyvaleric acid by 6 mol %, and others (linear 3-hydroxyalkanoic acid of 4 to 12 carbon atoms and 3-hydroxyalk-5-enoic acid with 10 or 12 carbon atoms) by 3 mol %.

Example 22

There were prepared two 2000-ml shake flasks, and, in each, 0.5 wt. % of polypeptone (supplied by Wako Pure Chemical Co.), 4 mmol/L of 5-phenylvaleric acid, and 1 mmol/L of dodecanedioic acid monoethyl ester were dissolved in 1000 ml of an aforementioned M9 culture medium, which was placed in a 2000 ml shake flask, then sterilized in an autoclave and cooled to the room temperature. Then 5 ml of a culture liquid of *Pseudomonas cichorii* YN2 strain, shake cultured in advance in an M9 culture medium containing 0.5% of polypeptone for 8 hours at 30° C., was added to each prepared culture medium, and culture was conducted for 41 hours at 30° C. After the culture, the cells were recovered by centrifuging, rinsed with methanol and lyophilized. The dried cells, after weighing, were agitated with chloroform for 48 hours at 50° C. to extract a polymer. The chloroform extract was filtered, then concentrated in an evaporator, and a solid precipitate formed with cold methanol was collected and dried under a reduced pressure to obtain a desired polymer. According to a weighing of the obtained polymer, 910 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=78000 and a weight-averaged molecular weight Mw=157000.

For specifying the structure of the obtained PHA, a NMR analysis was conducted under same conditions as in Example 1.

As a result, there was confirmed a polyhydroxy alkanoate copolymer including, as monomer units, 3-hydroxy-5-phenylvaleric acid represented by the following chemical formula (60) by 78 mol %, three units of 3-hydroxy-11-ethoxycarbonylundecanoic acid represented by the following chemical formula (69), 3-hydroxy-9-ethoxycarbonylnonanoic acid represented by a chemical formula (70), and 3-hydroxy-7-ethoxycarbonylheptanoic acid represented by a chemical formula (71) collectively by 14 mol %, and others (linear 3-hydroxyalkanoic acid of 4 to 12 carbon atoms and 3-hydroxyalk-5-enoic acid with 10 or 12 carbon atoms) by 8 mol %.

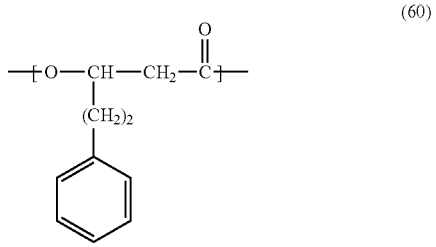

(60)

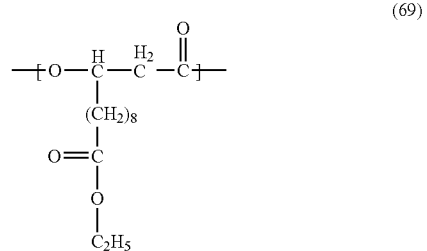

(69)

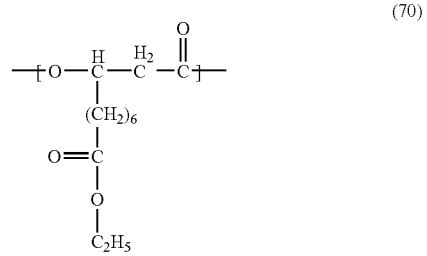

(70)

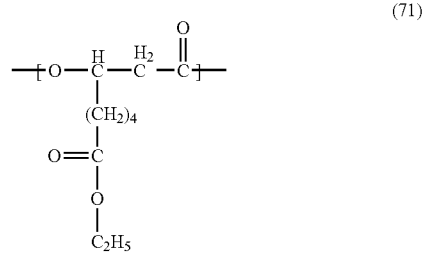

(71)

Example 23

There were prepared two 2000-ml shake flasks, and, in each, 0.5 wt. % of yeast extract (supplied by DIFCO), 4 mmol/L of 5-phenylvaleric acid, and 1 mmol/L of dodecanedioic acid monoethyl ester were dissolved in 1000 ml of an aforementioned M9 culture medium, which was placed in a 2000 ml shake flask, then sterilized in an autoclave and cooled to the room temperature. Then 5 ml of a culture liquid of *Pseudomonas cichorii* YN2 strain, shake cultured in advance in an M9 culture medium containing 0.5% of polypeptone for 8 hours at 30° C., was added to each prepared culture medium, and culture was conducted for 40 hours at 30° C. After the culture, the cells were recovered by centrifuging, rinsed with methanol and lyophilized. The dried cells, after weighing, were agitated with chloroform for 48 hours at 50° C. to extract a polymer. The chloroform extract was filtered, then concentrated in an evaporator, and a solid precipitate formed with cold methanol was collected and dried under a reduced pressure to obtain a desired polymer. According to a weighing of the obtained polymer, 250 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=75000 and a weight-averaged molecular weight Mw=152000.

For specifying the structure of the obtained PHA, a NMR analysis was conducted under same conditions as in Example 1.

As a result, there was confirmed a polyhydroxy alkanoate copolymer including, as monomer units, 3-hydroxy-5-phenylvaleric acid represented by the following chemical formula (60) by 75 mol %, three units of 3-hydroxy-11-ethoxycarbonylundecanoic acid represented by the following chemical formula (69), 3-hydroxy-9-ethoxycarbonylnonanoic acid represented by a chemical formula (70), and 3-hydroxy-7-ethoxycarbonylheptanoic acid represented by a chemical formula (71) collectively by 15 mol %, and others (linear 3-hydroxyalkanoic acid of 4 to 12 carbon atoms and 3-hydroxyalk-5-enoic acid with 10 or 12 carbon atoms) by 10 mol %.

(60)

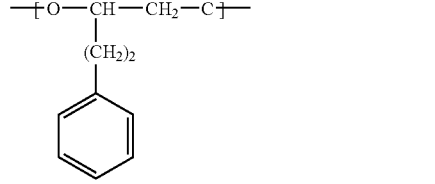

(69)

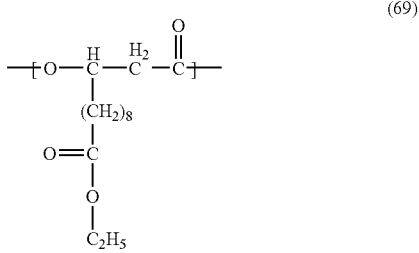

-continued

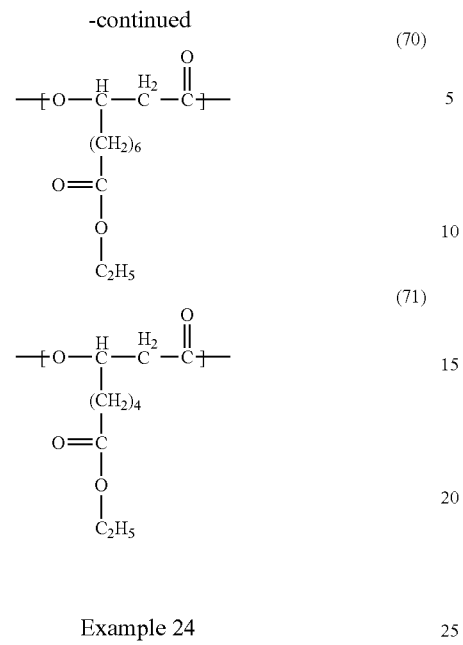

Example 24

There were prepared two 2000-ml shake flasks, and, in each, 0.5 wt. % of D-glucose (supplied by Kishida Kagaku), 4 mmol/L of 5-phenylvaleric acid, and 1 mmol/L of dodecanedioic acid monoethyl ester were dissolved in 1000 ml of an aforementioned M9 culture medium, which was placed in a 2000 ml shake flask, then sterilized in an autoclave and cooled to the room temperature. Then 5 ml of a culture liquid of Pseudomonas jessenii P161 strain, shake cultured in advance in an M9 culture medium containing 0.5% of polypeptone for 8 hours at 30° C., was added to each prepared culture medium, and culture was conducted for 40 hours at 30° C. After the culture, the cells were recovered by centrifuging, rinsed with methanol and lyophilized. The dried cells, after weighing, were agitated with chloroform for 48 hours at 50° C. to extract a polymer. The chloroform extract was filtered, then concentrated in an evaporator, and a solid precipitate formed with cold methanol was collected and dried under a reduced pressure to obtain a desired polymer. According to a weighing of the obtained polymer, 300 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=71000 and a weight-averaged molecular weight Mw=149000.

For specifying the structure of the obtained PHA, a NMR analysis was conducted under same conditions as in Example 1.

As a result, there was confirmed a polyhydroxy alkanoate copolymer including, as monomer units, 3-hydroxy-5-phenylvaleric acid represented by the following chemical formula (60) by 78 mol %, three units of 3-hydroxy-11-ethoxycarbonylundecanoic acid represented by the following chemical formula (69), 3-hydroxy-9-ethoxycarbonylnonanoic acid represented by a chemical formula (70), and 3-hydroxy-7-ethoxycarbonylheptanoic acid represented by a chemical formula (71) collectively by 14 mol %, and others (linear 3-hydroxyalkanoic acid of 4 to 12 carbon atoms and 3-hydroxyalk-5-enoic acid with 10 or 12 carbon atoms) by 8 mol %.

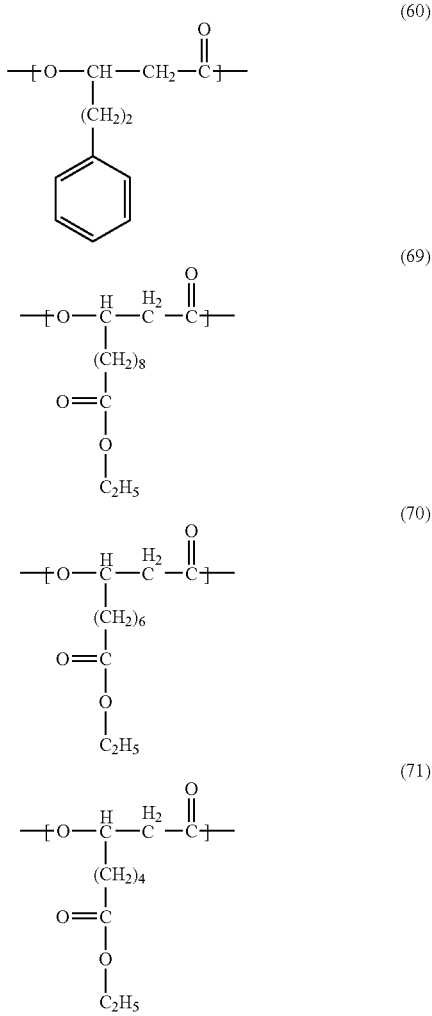

Example 25

There were prepared two 2000-ml shake flasks, and, in each, 0.5 wt. % of polypeptone (supplied by Wako Pure Chemicals Co.), 4 mmol/L of 5-phenoxyvaleric acid, and 1 mmol/L of dodecanedioic acid monoethyl ester were dissolved in 1000 ml of an aforementioned M9 culture medium, which was placed in a 2000 ml shake flask, then sterilized in an autoclave and cooled to the room temperature. Then 5 ml of a culture liquid of Pseudomonas cichorii YN2 strain, shake cultured in advance in an M9 culture medium containing 0.5% of polypeptone for 8 hours at 30° C., was added to each prepared culture medium, and culture was conducted for 41 hours at 30° C. After the culture, the cells were recovered by centrifuging, rinsed with methanol and lyophilized. The dried cells, after weighing, were agitated with chloroform for 48 hours at 50° C. to extract a polymer. The chloroform extract was filtered, then concentrated in an evaporator, and a solid precipitate formed with cold methanol was collected and dried under a reduced pressure to obtain a desired polymer. According to a weighing of the obtained polymer, 680 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=69000 and a weight-averaged molecular weight Mw=135000.

For specifying the structure of the obtained PHA, a NMR analysis was conducted under same conditions as in Example 1.

As a result, there was confirmed a polyhydroxy alkanoate copolymer including, as monomer units, 3-hydroxy-5-phenoxyvaleric acid represented by the following chemical formula (53) by 74 mol %, three units of 3-hydroxy-11-ethoxycarbonylundecanoic acid represented by the following chemical formula (69), 3-hydroxy-9-ethoxycarbonylnonanoic acid represented by a chemical formula (70), and 3-hydroxy-7-ethoxycarbonylheptanoic acid represented by a chemical formula (71) collectively by 17 mol %, and others (linear 3-hydroxyalkanoic acid of 4 to 12 carbon atoms and 3-hydroxyalk-5-enoic acid with 10 or 12 carbon atoms) by 9 mol %.

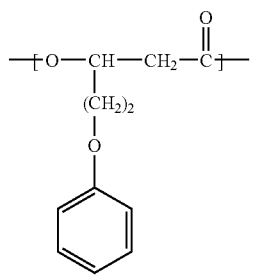

(53)

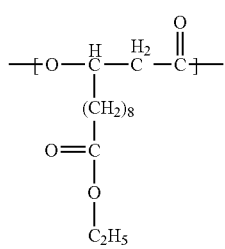

(69)

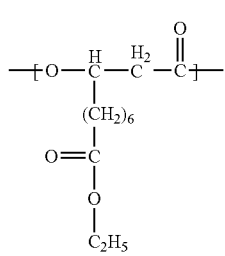

(70)

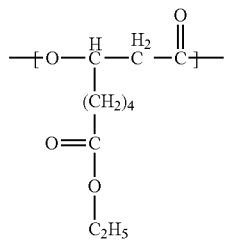

(71)

Example 26

There were prepared two 2000-ml shake flasks, and, in each, 0.5 wt. % of polypeptone (supplied by Wako Pure Chemicals Co.), 4 mmol/L of 4-cyclohexylbutyric acid, and 1 mmol/L of dodecanedioic acid monoethyl ester were dissolved in 1000 ml of an aforementioned M9 culture medium, which was placed in a 2000 ml shake flask, then sterilized in an autoclave and cooled to the room temperature. Then 5 ml of a culture liquid of *Pseudomonas cichorii* YN2 strain, shake cultured in advance in an M9 culture medium containing 0.5% of polypeptone for 8 hours at 30° C., was added to each prepared culture medium, and culture was conducted for 41 hours at 30° C. After the culture, the cells were recovered by centrifuging, rinsed with methanol and lyophilized. The dried cells, after weighing, were agitated with chloroform for 48 hours at 50° C. to extract a polymer. The chloroform extract was filtered, then concentrated in an evaporator, and a solid precipitate formed with cold methanol was collected and dried under a reduced pressure to obtain a desired polymer. According to a weighing of the obtained polymer, 720 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=81000 and a weight-averaged molecular weight Mw=160000.

For specifying the structure of the obtained PHA, a NMR analysis was conducted under same conditions as in Example 1.

As a result, there was confirmed a polyhydroxy alkanoate copolymer including, as monomer units, 3-hydroxy-4-cyclohexylbutyric acid represented by the following chemical formula (57) by 76 mol %, three units of 3-hydroxy-11-ethoxycarbonylundecanoic acid represented by the following chemical formula (69), 3-hydroxy-9-ethoxycarbonylnonanoic acid represented by a chemical formula (70), and 3-hydroxy-7-ethoxycarbonylheptanoic acid represented by a chemical formula (71) collectively by 16 mol %, and others (linear 3-hydroxyalkanoic acid of 4 to 12 carbon atoms and 3-hydroxyalk-5-enoic-acid with 10 or 12 carbon atoms) by 8 mol %.

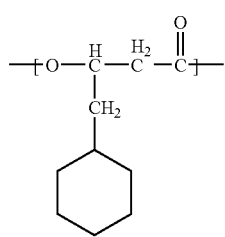

(57)

-continued

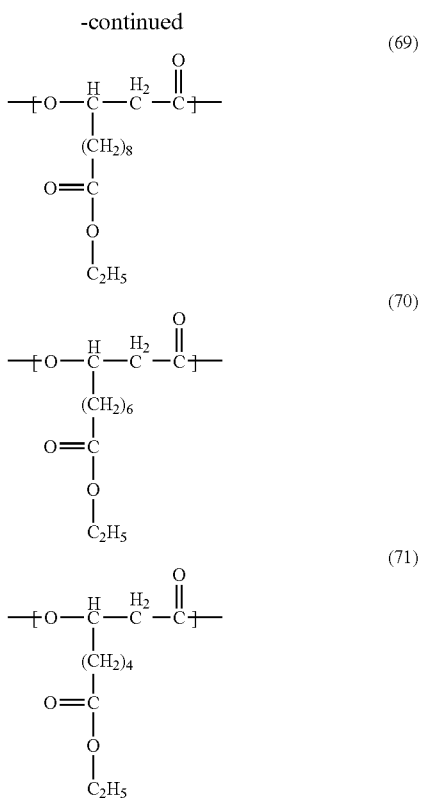

Example 27

There were prepared two 2000-ml shake flasks, and, in each, 0.5 wt. % of polypeptone (supplied by Wako Pure Chemicals Co.), 4 mmol/L of 5-(phenylsulfanyl)valeric acid, and 1 mmol/L of dodecanedioic acid monoethyl ester were dissolved in 1000 ml of an aforementioned M9 culture medium, which was placed in a 2000 ml shake flask, then sterilized in an autoclave and cooled to the room temperature. Then 5 ml of a culture liquid of *Pseudomonas cichorii* YN2 strain, shake cultured in advance in an M9 culture medium containing 0.5% of polypeptone for 8 hours at 30° C., was added to each prepared culture medium, and culture was conducted for 42 hours at 30° C. After the culture, the cells were recovered by centrifuging, rinsed with methanol and lyophilized. The dried cells, after weighing, were agitated with chloroform for 48 hours at 50° C. to extract a polymer. The chloroform extract was filtered, then concentrated in an evaporator, and a solid precipitate formed with cold methanol was collected and dried under a reduced pressure to obtain a desired polymer. According to a weighing of the obtained polymer, 890 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=84000 and a weight-averaged molecular weight Mw=169000.

For specifying the structure of the obtained PHA, a NMR analysis was conducted under same conditions as in Example 1.

As a result, there was confirmed a polyhydroxy alkanoate copolymer including, as monomer units, 3-hydroxy-5-(phenylsulfanyl)valeric acid represented by the following chemical formula (58) by 80 mol %, three units of 3-hydroxy-11-ethoxycarbonylundecanoic acid represented by the following chemical formula (69), 3-hydroxy-9-ethoxycarbonylnonanoic acid represented by a chemical formula (70), and 3-hydroxy-7-ethoxycarbonylheptanoic acid represented by a chemical formula (71) collectively by 14 mol %, and others (linear 3-hydroxyalkanoic acid of 4 to 12 carbon atoms and 3-hydroxyalk-5-enoic acid with 10 or 12 carbon atoms) by 6 mol %.

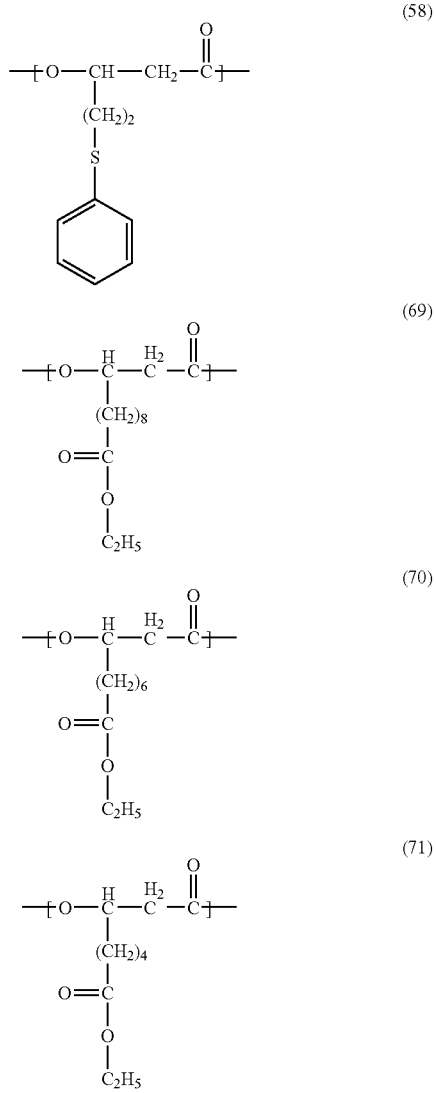

Example 28

There were prepared two 2000-ml shake flasks, and, in each, 0.5 wt. % of polypeptone (supplied by Wako Pure Chemicals Co.), 4 mmol/L of 5-benzoylvaleric acid, and 1 mmol/L of dodecanedioic acid monoethyl ester were dissolved in 1000 ml of an aforementioned M9 culture medium, which was placed in a 2000 ml shake flask, then sterilized in an autoclave and cooled to the room temperature. Then 5 ml of a culture liquid of *Pseudomonas cichorii* YN2 strain, shake cultured in advance in an M9 culture medium containing 0.5% of polypeptone for 8 hours at 30° C., was added to each prepared culture medium, and culture was conducted for 41 hours at 30° C. After the culture, the cells were recovered by centrifuging, rinsed with methanol and lyophilized. The dried cells, after weighing, were agitated with chloroform for 48 hours at 50° C. to extract a polymer. The chloroform extract was filtered, then concentrated in an evaporator, and a solid precipitate formed with cold methanol was collected and dried under a reduced pressure to obtain a desired polymer. According to a weighing of the obtained polymer, 450 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=156000 and a weight-averaged molecular weight Mw=325000.

For specifying the structure of the obtained PHA, a NMR analysis was conducted under same conditions as in Example 1.

As a result, there was confirmed a polyhydroxy alkanoate copolymer including, as monomer units, 3-hydroxy-5-benzoylvaleric acid represented by the following chemical formula (62) by 69 mol %, three units of 3-hydroxy-11-ethoxycarbonylundecanoic acid represented by the following chemical formula (69), 3-hydroxy-9-ethoxycarbonylnonanoic acid represented by a chemical formula (70), and 3-hydroxy-7-ethoxycarbonylheptanoic acid represented by a chemical formula (71) collectively by 18 mol %, and others (linear 3-hydroxyalkanoic acid of 4 to 12 carbon atoms and 3-hydroxyalk-5-enoic acid with 10 or 12 carbon atoms) by 13 mol %.

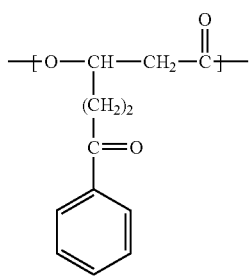

(62)

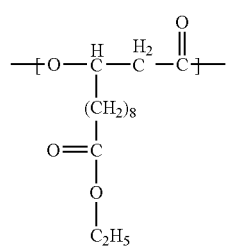

(69)

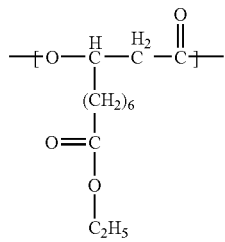

(70)

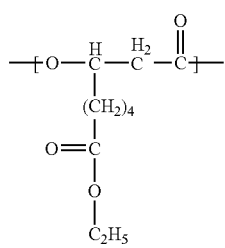

(71)

Example 29

There were prepared two 2000-ml shake flasks, and, in each, 0.5 wt. % of polypeptone (supplied by Wako Pure Chemicals Co.), 4 mmol/L of 5-(4-cyanophenoxy)valeric acid, and 1 mmol/L of sebacic acid monomethyl ester were dissolved in 1000 ml of an aforementioned M9 culture medium, which was placed in a 2000 ml shake flask, then sterilized in an autoclave and cooled to the room temperature. Then 5 ml of a culture liquid of *Pseudomonas cichorii* YN2 strain, shake cultured in advance in an M9 culture medium containing 0.5% of polypeptone for 8 hours at 30° C., was added to each prepared culture medium, and culture was conducted for 41 hours at 30° C. After the culture, the cells were recovered by centrifuging, rinsed with methanol and lyophilized. The dried cells, after weighing, were agitated with chloroform for 48 hours at 50° C. to extract a polymer. The chloroform extract was filtered, then concentrated in an evaporator, and a solid precipitate formed with cold methanol was collected and dried under a reduced pressure to obtain a desired polymer. According to a weighing of the obtained polymer, 450 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=68000 and a weight-averaged molecular weight Mw=129000.

For specifying the structure of the obtained PHA, a NMR analysis was conducted under same conditions as in Example 1.

As a result, there was confirmed a polyhydroxy alkanoate copolymer including, as monomer units, 3-hydroxy-5-(4-cyanophenoxy)valeric acid represented by the following chemical formula (72) by 34 mol %, two units of 3-hydroxy-9-methoxycarbonylnonanoic acid represented by the following chemical formula (73) and 3-hydroxy-7-methoxycarbonylheptanoic acid represented by a chemical formula (74) collectively by 16 mol %, and others (linear 3-hydroxyalkanoic acid of 4 to 12 carbon atoms and 3-hydroxyalk-5-enoic acid with 10 or 12 carbon atoms) by 50 mol %.

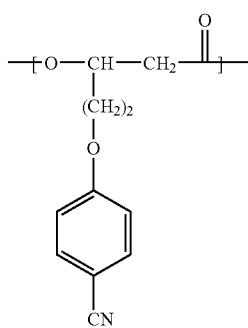

(72)

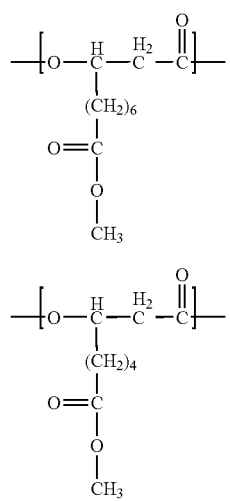

(73)

(74)

Example 30

There were prepared two 2000-ml shake flasks, and, in each, 0.1 wt. % of n-nonanoic acid (supplied by Kishida Kagaku), 4 mmol/L of 5-(4-nitrophenyl)valeric acid, and 1 mmol/L of sebacic acid monomethyl ester were dissolved in 1000 ml of an aforementioned M9 culture medium, which was placed in a 2000 ml shake flask, then sterilized in an autoclave and cooled to the room temperature. Then 5 ml of a culture liquid of *Pseudomonas cichorii* YN2 strain, shake cultured in advance in an M9 culture medium containing 0.5% of polypeptone for 8 hours at 30° C., was added to each prepared culture medium, and culture was conducted for 72 hours at 30° C. After the culture, the cells were recovered by centrifuging, rinsed with methanol and lyophilized. The dried cells, after weighing, were agitated with chloroform for 48 hours at 50° C. to extract a polymer. The chloroform extract was filtered, then concentrated in an evaporator, and a solid precipitate formed with cold methanol was collected and dried under a reduced pressure to obtain a desired polymer. According to a weighing of the obtained polymer, 170 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=59000 and a weight-averaged molecular weight Mw=125000.

For specifying the structure of the obtained PHA, a NMR analysis was conducted under same conditions as in Example 1.

As a result, there was confirmed a polyhydroxy alkanoate copolymer including, as monomer units, 3-hydroxy-5-(4-nitrophenyl)valeric acid represented by the following chemical formula (75) by 8 mol %, two units of 3-hydroxy-9-methoxycarbonylnonanoic acid represented by the following chemical formula (73) and 3-hydroxy-7-methoxycarbonylheptanoic acid represented by a chemical formula (74) collectively by 18 mol %, and others (linear 3-hydroxyalkanoic acid of 4 to 12 carbon atoms and 3-hydroxyalk-5-enoic acid with 10 or 12 carbon atoms) by 74 mol %.

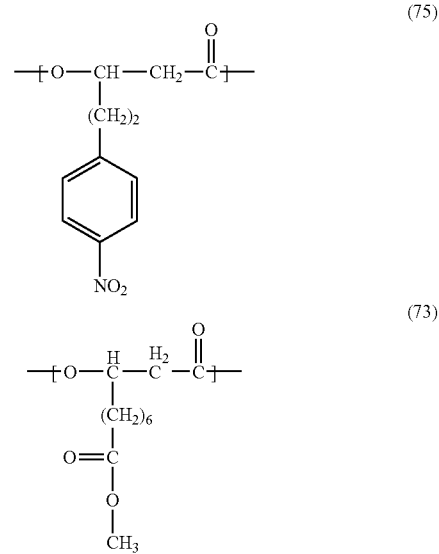

(75)

(73)

(74)

Example 31

There were prepared two 2000-ml shake flasks, and, in each, 0.1 wt. % of n-nonanoic acid (supplied by Kishida Kagaku), 4 mmol/L of 5-[(phenylmethyl)oxy]valeric acid, and 1 mmol/L of sebacic acid monomethyl ester were dissolved in 10000 ml of an aforementioned M9 culture medium, which was placed in a 2000 ml shake flask, then sterilized in an autoclave and cooled to the room temperature. Then 5 ml of a culture liquid of *Pseudomonas cichorii* YN2 strain, shake cultured in advance in an M9 culture medium containing 0.5% of polypeptone for 8 hours at 30° C., was added to each prepared culture medium, and culture was conducted for 40 hours at 30° C. After the culture, the cells were recovered by centrifuging, rinsed with methanol and lyophilized. The dried cells, after weighing, were agitated with chloroform for 48 hours at 50° C. to extract a polymer. The chloroform extract was filtered, then concentrated in an evaporator, and a solid precipitate formed with cold methanol was collected and dried under a reduced pressure to obtain a desired polymer. According to a weighing of the obtained polymer, 330 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=79000 and a weight-averaged molecular weight Mw=152000.

For specifying the structure of the obtained PHA, a NMR analysis was conducted under same conditions as in Example 1.

As a result, there was confirmed a polyhydroxy alkanoate copolymer including, as monomer units, 3-hydroxy-5-[(phenylmethyl)oxy]valeric acid represented by the following chemical formula (68) by 81 mol %, two units of 3-hydroxy-9-methoxycarbonylnonanoic acid represented by the following chemical formula (73) and 3-hydroxy-7-methoxycarbonylheptanoic acid represented by a chemical formula (74) collectively by 13 mol %, and others (linear 3-hydroxyalkanoic acid of 4 to 12 carbon atoms and 3-hydroxyalk-5-enoic acid with 10 or 12 carbon atoms) by 6 mol %.

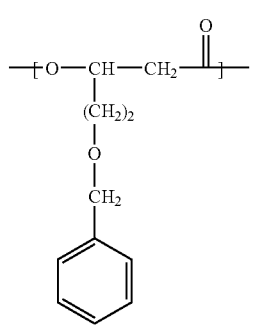

(68)

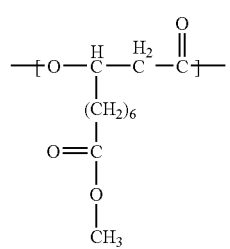

(73)

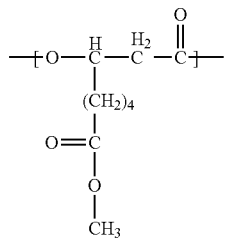

(74)

Example 32

There were prepared two 2000-ml shake flasks, and, in each, 0.5 wt. % of polypeptone (supplied by Wako Pure Chemical Co.), 4 mmol/L of 5-5-phenylvaleric acid, and 1 mmol/L of sebacic acid monomethyl ester were dissolved in 1000 ml of an aforementioned M9 culture medium, which was placed in a 2000 ml shake flask, then sterilized in an autoclave and cooled to the room temperature. Then 5 ml of a culture liquid of *Pseudomonas cichorii* YN2 strain, shake cultured in advance in an M9 culture medium containing 0.5% of polypeptone for 8 hours at 30° C., was added to each prepared culture medium, and culture was conducted for 40 hours at 30° C. After the culture, the cells were recovered by centrifuging, rinsed with methanol and lyophilized. The dried cells, after weighing, were agitated with chloroform for 48 hours at 50° C. to extract a polymer. The chloroform extract was filtered, then concentrated in an evaporator, and a solid precipitate formed with cold methanol was collected and dried under a reduced pressure to obtain a desired polymer. According to a weighing of the obtained polymer, 1340 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=81000 and a weight-averaged molecular weight Mw=159000.

For specifying the structure of the obtained PHA, a NMR analysis was conducted under same conditions as in Example 1.

As a result, there was confirmed a polyhydroxy alkanoate copolymer including, as monomer units, 3-hydroxy-5-phenylvaleric acid represented by the following chemical formula (60) by 77 mol %, two units of 3-hydroxy-9-methoxycarbonylnonanoic acid represented by the following chemical formula (73) and 3-hydroxy-7-methoxycarbonylheptanoic acid represented by a chemical formula (74) collectively by 19 mol %, and others (linear 3-hydroxyalkanoic acid of 4 to 12 carbon atoms and 3-hydroxyalk-5-enoic acid with 10 or 12 carbon atoms) by 4 mol %.

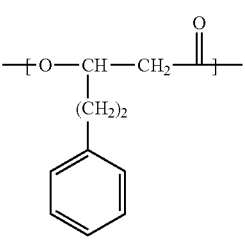

(60)

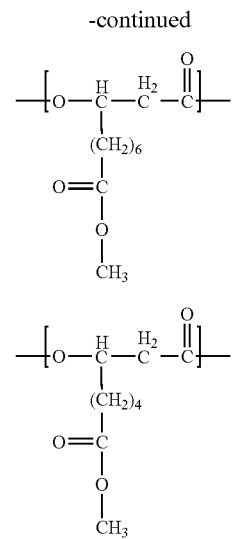

(73)

(74)

The polyhydroxy alkanoate thus obtained was utilized in the following reaction.

The synthesized polyhydroxy alkanoate was formed into a film, and 500 mg of such film was placed on a Petri dish and was let to stand for 5 hours in 100 ml of a 0.1N aqueous solution of sodium hydroxide. After the reaction, the sodium hydroxide solution was removed, and the polymer was washed three times with 100 ml of distilled water. Then the polymer was dissolved in 200 ml of ethyl acetate, and, after an addition of 100 ml of a 1.0N aqueous solution of hydrochloric acid, the solution was agitated for 1 hour at the room temperature. Then the polymer was extracted, washed with distilled water and the solvent was distilled off to recover the polymer. Thereafter, a drying under a reduced pressure was carried out to obtain 350 mg of a desired polymer.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=9500 and a weight-averaged molecular weight Mw=32000.

For specifying the structure of the obtained PHA, a NMR analysis was conducted under same conditions as in Example 1.

As a result, there was confirmed a polyhydroxy alkanoate copolymer including, as monomer units, 3-hydroxy-5-phenylvaleric acid represented by the following chemical formula (60), 3-hydroxy-9-carboxynonanoic acid represented by the following chemical formula (54) and 3-hydroxy-7-carboxyheptanoic acid represented by a chemical formula (55).

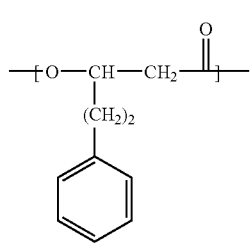

(60)

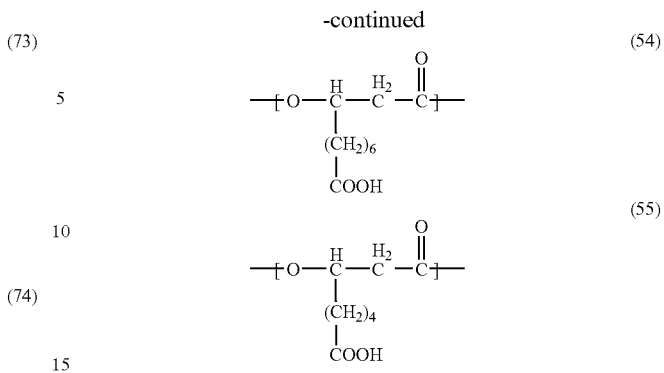

Also a proportion of the units in the obtained polymer was calculated from a decrease in ester groups, and confirmed as 3-hydroxy-5-phenylvaleric acid by 78 mol %, 3-hydroxy-9-carboxylnonanoic acid and 3-hydroxy-7-carboxylheptanoic acid collectively by 12 mol %, 3-hydroxy-9-methoxycarbonylnonanoic acid and 3-hydroxy-7-methoxycarbonylheptanoic acid collectively by 6 mol %, and others (linear 3-hydroxyalkanoic acid of 4 to 12 carbon atoms and 3-hydroxyalk-5-enoic acid with 10 or 12 carbon atoms) by 4 mol %.

Example 33

There were prepared two 2000-ml shake flasks, and, in each, 0.5 wt. % of polypeptone (supplied by Wako Pure Chemical Co.), 4 mmol/L of 5-phenoxyvaleric acid, and 1 mmol/L of sebacic acid monomethyl ester were dissolved in 1000 ml of an aforementioned M9 culture medium, which was placed in a 2000 ml shake flask, then sterilized in an autoclave and cooled to the room temperature. Then 5 ml of a culture liquid of Pseudomonas cichorii YN2 strain, shake cultured in advance in an M9 culture medium containing 0.5% of polypeptone for 8 hours at 30° C., was added to each prepared culture medium, and culture was conducted for 40 hours at 30° C. After the culture, the cells were recovered by centrifuging, rinsed with methanol and lyophilized. The dried cells, after weighing, were agitated with chloroform for 48 hours at 50° C. to extract a polymer. The chloroform extract was filtered, then concentrated in an evaporator, and a solid precipitate formed with cold methanol was collected and dried under a reduced pressure to obtain a desired polymer. According to a weighing of the obtained polymer, 710 mg (dry weight) of PHA were obtained in the present example.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=71000 and a weight-averaged molecular weight Mw=148000.

For specifying the structure of the obtained PHA, a NMR analysis was conducted under same conditions as in Example 1.

As a result, there was confirmed a polyhydroxy alkanoate copolymer including, as monomer units, 3-hydroxy-5-phenoxyvaleric acid represented by the following chemical formula (53) by 74 mol %, two units of 3-hydroxy-9-methoxycarbonylnonanoic acid represented by the following chemical formula (73) and 3-hydroxy-7-methoxycarbonylheptanoic acid represented by a chemical formula (74) collectively by 18 mol %, and others (linear 3-hydroxyalkanoic acid of 4 to 12 carbon atoms and 3-hydroxyalk-5-enoic acid with 10 or 12 carbon atoms) by 8 mol %.

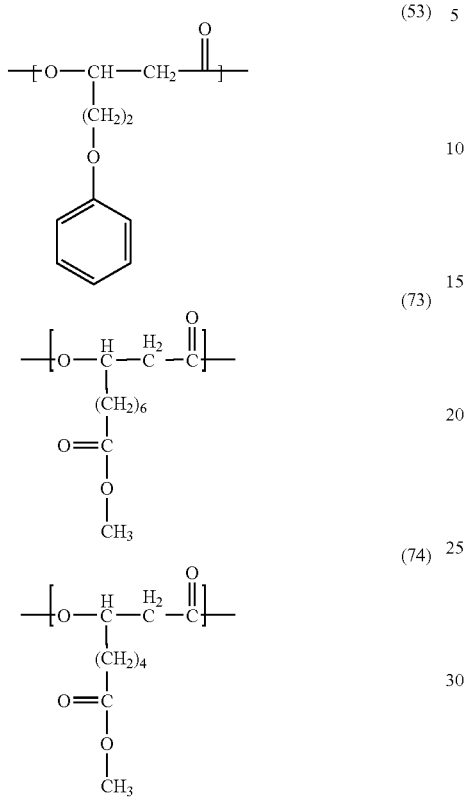

The polyhydroxy alkanoate thus obtained was utilized in the following reaction.

The synthesized polyhydroxy alkanoate was formed into a film, and 500 mg of such film was placed on a Petri dish and was let to stand for 5 hours in 100 ml of a 0.1N aqueous solution of sodium hydroxide. After the reaction, the sodium hydroxide solution was removed, and the polymer was washed three times with 100 ml of distilled water. Then the polymer was dissolved in 200 ml of ethyl acetate, and, after an addition of 100 ml of a 1.0N aqueous solution of hydrochloric acid, the solution was agitated for 1 hour at the room temperature. Then the polymer was extracted, washed with distilled water and the solvent was distilled off to recover the polymer. Thereafter, a drying under a reduced pressure was carried out to obtain 370 mg of a desired polymer.

An average molecular weight of the obtained PHA was measured by gel permeation chromatography (GPC: Toso HLC-8220 GPC, column: Toso TSK-GEL Super HM-H, solvent: chloroform, converted to polystyrene). As a result there were obtained a number-averaged molecular weight Mn=8700 and a weight-averaged molecular weight Mw=30900.

For specifying the structure of the obtained PHA, a NMR analysis was conducted under same conditions as in Example 1.

As a result, there was confirmed a polyhydroxy alkanoate copolymer including, as monomer units, 3-hydroxy-5-phenoxyvaleric acid represented by the following chemical formula (53), 3-hydroxy-9-carboxynonanoic acid represented by the following chemical formula (54) and 3-hydroxy-7-carboxyheptanoic acid represented by a chemical formula (55).

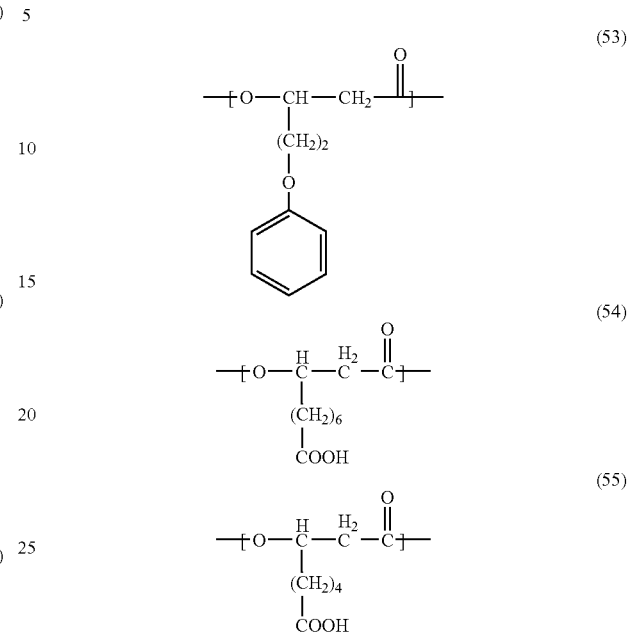

Also a proportion of the units in the obtained polymer was calculated from a decrease in ester groups, and confirmed as 3-hydroxy-5-phenoxyvaleric acid by 73 mol %, 3-hydroxy-9-carboxynbnanoic acid and 3-hydroxy-7-carboxyheptanoic acid collectively by 10 mol %, 3-hydroxy-9-methoxycarbonylnonanoic acid and 3-hydroxy-7-methoxycarbonylheptanoic acid collectively by 8 mol %, and others (linear 3-hydroxyalkanoic acid of 4 to 12 carbon atoms and 3-hydroxyalk-5-enoic acid with 10 or 12 carbon atoms) by 9 mol %.

Example 34

In 1000 mL of an aforementioned M9 culture medium, there were added 0.5 wt. % of polypeptone (supplied by Wako Pure Chemical Co.), and 5-phenylvaleric acid and sebacic acid monomethyl ester so as to obtain final concentrations of 4 and 1 mmol/L respectively, and the solution was placed in a 2000 ml shake flask, then sterilized in an autoclave and cooled to the room temperature. Then 5 ml of a culture liquid of *Pseudomonas cichorii* YN2 strain, shake cultured in advance in an M9 culture medium containing 0.5% of polypeptone for 8 hours at 30° C., was added to each prepared culture medium, and culture was conducted for 40 hours at 30° C. After the culture, the cells were recovered by centrifuging, rinsed with methanol and lyophilized. The dried cells, after weighing, were agitated with chloroform for 48 hours at 50° C. to extract a polymer. The chloroform extract was filtered, then concentrated in an evaporator, and a solid precipitate formed with cold methanol was collected and dried under a reduced pressure to obtain a desired polymer.

Figures 5, 6:
FIG. 5 is a GC-MS TIC spectrum of a methylation decomposite of a polyester obtained in Example 34.
FIG. 6 is a mass spectrum of a peak derived from a unit shown by a chemical formula (80) of a methylation decomposite of the polyester, obtained in Example 34.
Figure 7:
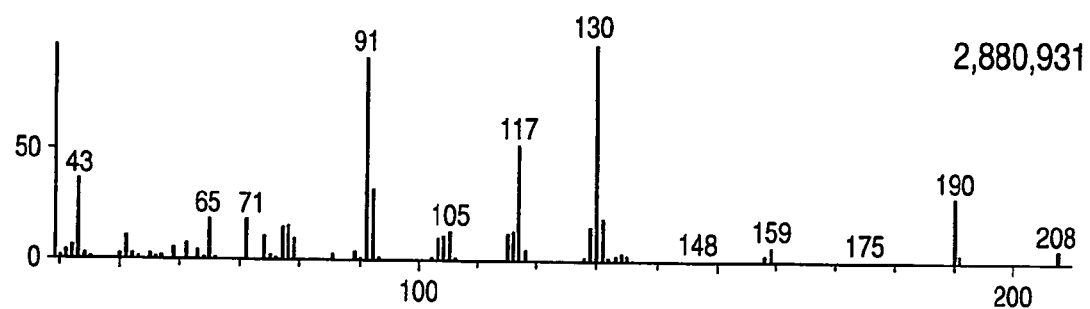
FIG. 7 is a mass spectrum of a peak derived from a unit shown by a chemical formula (81) of a methylation decomposite of the polyester obtained in Example 34.
Figure 8:
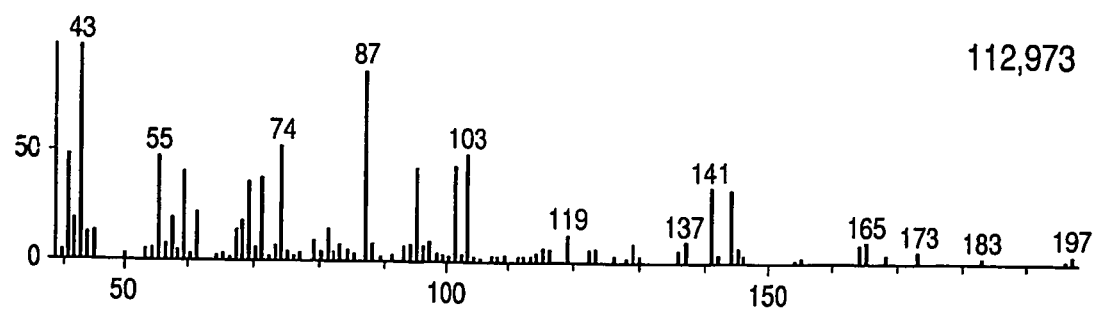
FIG. 8 is a mass spectrum of a peak derived from a unit shown by a chemical formula (82) of a methylation decomposite of the polyester obtained in Example 34.

A structure determination of the obtained polymer was carried out by a methynolysis-GC/MS method to be explained in the following. 5 mg of the polymer were dissolved in 2 mL of chloroform, then added with 2 mL of a 3% methanol solution of sulfuric acid and refluxed for 3.5 hours at 100° C. After the reaction, the reaction mixture was cooled to the room temperature and separated by adding 10 mL of deionized water under agitation. Then an organic layer was dehydrated with magnesium sulfate (anhydrous) and the reaction liquid was subjected to a measurement by a gas chromatography-mass spectrometer (GC/MS: Shimadzu QP-5050A, column: DB-WAXETR 0.32 mm×30 m). An obtained total ion chromatogram (TIC) is shown in FIG. 5. There were observed three main peaks at 35.6, 38.0 and 45.8 minutes. A mass spectrum (MS) of the peak at 35.6 minutes is shown in FIG. 6; a MS of the peak at 38.0 minutes is shown in FIG. 7; and a MS of the peak at 45.8 minutes is shown in FIG. 8.

As a result, the peak at 35.6 minutes was derived from a unit shown in a chemical formula (80):

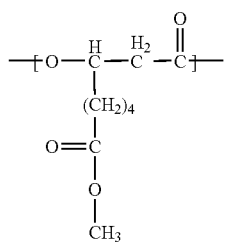
(80)

the peak at 38.0 minutes was derived from a unit shown in a chemical formula (81):

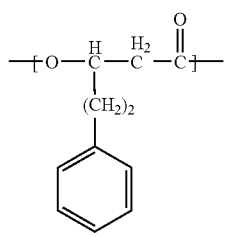
(81)

and the peak at 35.6 minutes was derived from a unit shown in a chemical formula (82):

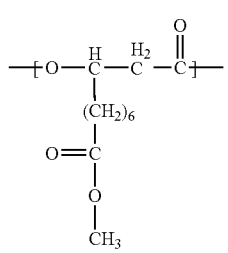
(82)

Also proportions of the units, calculated from ratios of the peak areas of TIC, were 12.0%, 77.7% and 6.7% respectively.

The molecular weight of the polymer was measured by gel permeation chromatography (GPC: Toso HLC-8220 GPC, column: Toso TSK-GEL Super HM-H, solvent: chloroform, converted to polystyrene). Table 1 shows weights of the obtained cells and the obtained polymer, a polymer weight ratio per cell, The molecular weight and The molecular weight distribution of the obtained polymer.

TABLE 1

| CDW (mg/L) | PDW (mg/L) | P/C % | Mn (×10⁴) | Mw (×10⁴) | Mw/Mn |
|---|---|---|---|---|---|
| 1358 | 671 | 49.4 | 8.1 | 15.9 | 2.0 |

CDW: cell dry weight,
PDW: polymer dry weight,
P/C: cell dry weight/polymer dry weight,
Mn: number-averaged molecular weight,
Mw: weight-averaged molecular weight,
Mw/Mn: molecular weight distribution.

Example 35

A desired polymer was obtained in the same manner as in Example 34, except that the YN2 strain employed in Example 34 was replaced by *Pseudomonas jessenii* P161 strain.

A structure determination of the obtained polymer carried out by a methanolysis-GC/MS method as in Example 34 confirmed that the polymer was a polyhydroxy alkanoate copolymer constituted of units represented by chemical formulas (80), (81) and (82):

chemical formula (80):

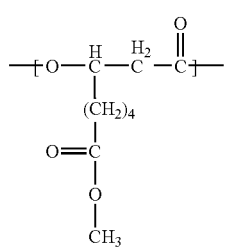
(80)

chemical formula (81):

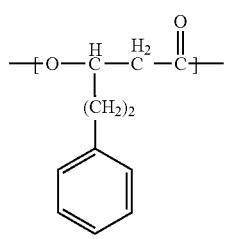
(81)

chemical formula (82):

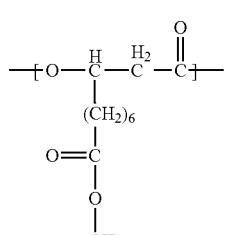
(82)

and the proportions of the units, calculated from the ratios of the peak areas of TIC, were 15.5%, 75.2% and 9.3% respectively.

The molecular weight of the polymer was measured by gel permeation chromatography as in Example 34.

Table 2 shows weights of the obtained cells and the obtained polymer, a polymer weight ratio per cell, the molecular weight and the molecular weight distribution of the obtained polymer.

TABLE 2

| CDW (mg/L) | PDW (mg/L) | P/C % | Mn (×10$^4$) | Mw (×10$^4$) | Mw/Mn |
|---|---|---|---|---|---|
| 821 | 271 | 33.0 | 6.6 | 13.9 | 2.1 |

CDW: cell dry weight,
PDW: polymer dry weight,
P/C: cell dry weight/polymer dry weight,
Mn: number-averaged molecular weight,
Mw: weight-averaged molecular weight,
Mw/Mn: molecular weight distribution.

Example 36

A desired polymer was obtained in the same manner as in Example 34, except that the YN2 strain employed in Example 34 was replaced by *Pseudomonas cichorii* H45 strain and polypeptone was replaced by yeast extract (DIFCO).

A structure determination of the obtained polymer carried out by a methanolysis-GC/MS method as in Example 34 confirmed that the polymer was a polyhydroxy alkanoate copolymer constituted of units represented by chemical formulas (80), (81) and (82):

chemical formula (80):

$$-\!\!\left[\mathrm{O}-\underset{\mathrm{H}}{\mathrm{C}}-\underset{\mathrm{H_2}}{\mathrm{C}}-\overset{\mathrm{O}}{\underset{\|}{\mathrm{C}}}\right]\!\!- \quad (80)$$
$(CH_2)_4$
$O=C$
$O$
$CH_3$ chemical formula (81):

$$-\!\!\left[\mathrm{O}-\underset{\mathrm{H}}{\mathrm{C}}-\underset{\mathrm{H_2}}{\mathrm{C}}-\overset{\mathrm{O}}{\underset{\|}{\mathrm{C}}}\right]\!\!- \quad (81)$$
$(CH_2)_2$
(phenyl)

chemical formula (82):

$$-\!\!\left[\mathrm{O}-\underset{\mathrm{H}}{\mathrm{C}}-\underset{\mathrm{H_2}}{\mathrm{C}}-\overset{\mathrm{O}}{\underset{\|}{\mathrm{C}}}\right]\!\!- \quad (82)$$
$(CH_2)_6$
$O=C$
$O$
$CH_3$ and the proportions of the units calculated from the ratios of the peak areas of TIC were 16.1%, 72.3% and 11.6% respectively.

The molecular weight of the polymer was measured by gel permeation chromatography as in Example 34.

Table 3 shows weights of the obtained cells and the obtained polymer, polymer weight ratio per cell, the molecular weight and the molecular weight distribution of the obtained polymer.

TABLE 3

| CDW (mg/L) | PDW (mg/L) | P/C % | Mn (×10$^4$) | Mw (×10$^4$) | Mw/Mn |
|---|---|---|---|---|---|
| 779 | 230 | 29.5 | 7.2 | 14.9 | 2.1 |

CDW: cell dry weight,
PDW: polymer dry weight,
P/C: cell dry weight/polymer dry weight,
Mn: number-averaged molecular weight,
Mw: weight-averaged molecular weight,
Mw/Mn: molecular weight distribution.

Example 37

A desired polymer was obtained in the same manner as in Example 34, except that the YN2 strain employed in Example 34 was replaced by *Pseudomonas putida* P91 strain and polypeptone was replaced by n-nonanoic acid (Kishida Kagaku, concentration: 0.1%).

A structure determination of the obtained polymer carried out by a methanolysis-GC/MS method as in Example 34 confirmed that the polymer was a polyhydroxy alkanoate copolymer constituted of units represented by chemical formulas (80), (81), (82), (83), (84) and (85):

chemical formula (80)

$$-\!\!\left[\mathrm{O}-\underset{\mathrm{H}}{\mathrm{C}}-\underset{\mathrm{H_2}}{\mathrm{C}}-\overset{\mathrm{O}}{\underset{\|}{\mathrm{C}}}\right]\!\!- \quad (80)$$
$(CH_2)_4$
$O=C$
$O$
$CH_3$ chemical formula (81):

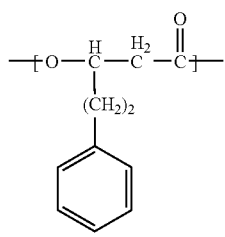

chemical formula (82)

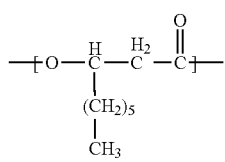

chemical formula (83):

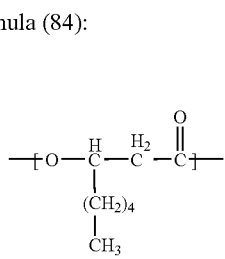

chemical formula (84):

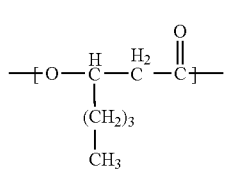

chemical formula (85):

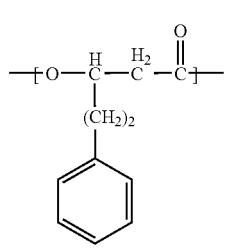

and the proportions of the units calculated from the ratios of the peak areas of TIC were 5.1%, 52.1%, 6.6%, 11.3%, 4.9% and 20.0% respectively.

The molecular weight of the polymer was measured by gel permeation chromatography as in Example 34.

Table 4 shows weights of the obtained cells and the obtained polymer, a polymer weight ratio per cell, a molecular weight and a molecular weight distribution of the obtained polymer.

TABLE 4

| CDW (mg/L) | PDW (mg/L) | P/C % | Mn (×10⁴) | Mw (×10⁴) | Mw/Mn |
|---|---|---|---|---|---|
| 528 | 110 | 20.8 | 8.2 | 16.9 | 2.1 |

CDW: cell dry weight,
PDW: polymer dry weight,
P/C: cell dry weight/polymer dry weight,
Mn: number-averaged molecular weight,
Mw: weight-averaged molecular weight,
Mw/Mn: molecular weight distribution.

Example 38

A desired polymer was obtained in the same manner as in Example 34, except that polypeptone was replaced by D-glucose (Kishida Kagaku).

A structure determination of the obtained polymer carried out by a methanolysis-GC/MS method as in Example 34 confirmed that the polymer was a polyhydroxy alkanoate copolymer constituted of units represented by chemical formulas (80), (81) and (82):

chemical formula (80):

chemical formula (81):

chemical formula (82):

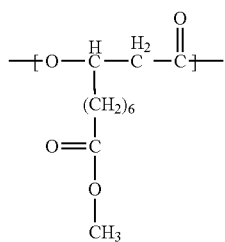
(82)

and the proportions of the units calculated from the ratios of the peak areas of TIC were 13.1%, 80.3% and 6.6% respectively.

The molecular weight of the polymer was measured by gel permeation chromatography as in Example 34.

Table 5 shows weights of the obtained cells and the obtained polymer, a polymer weight ratio per cell, a molecular weight and a molecular weight distribution of the obtained polymer.

TABLE 5

| CDW (mg/L) | PDW (mg/L) | P/C % | Mn ($\times 10^4$) | Mw ($\times 10^4$) | Mw/Mn |
|---|---|---|---|---|---|
| 910 | 425 | 46.7 | 7.9 | 15.4 | 1.9 |

CDW: cell dry weight,
PDW: polymer dry weight,
P/C: cell dry weight/polymer dry weight,
Mn: number-averaged molecular weight,
Mw: weight-averaged molecular weight,
Mw/Mn: molecular weight distribution.

Example 39

A desired polymer was obtained in the same manner as in Example 34, except that polypeptone was replaced by sodium pyruvate (Kishida Kagaku).

A structure determination of the obtained polymer carried out by a methanolysis-GC/MS method as in Example 34 confirmed that the polymer was a polyhydroxy alkanoate copolymer constituted of units represented by chemical formulas (80), (81) and (82):

chemical formula (80):

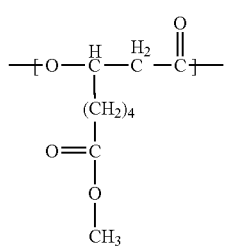
(80)

chemical formula (81):

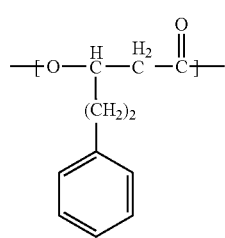
(81)

chemical formula (82):

(82)

and the proportions of the units calculated from the ratios of the peak areas of TIC were 11.9%, 82.2% and 5.9% respectively.

The molecular weight of the polymer was measured by gel permeation chromatography as in Example 34.

Table 6 shows weights of the obtained cells and the obtained polymer, a polymer weight ratio per cell, a molecular weight and a molecular weight distribution of the obtained polymer.

TABLE 6

| CDW (mg/L) | PDW (mg/L) | P/C % | Mn ($\times 10^4$) | Mw ($\times 10^4$) | Mw/Mn |
|---|---|---|---|---|---|
| 1120 | 585 | 52.2 | 8.0 | 15.9 | 2.0 |

CDW: cell dry weight,
PDW: polymer dry weight,
P/C: cell dry weight/polymer dry weight,
Mn: number-averaged molecular weight,
Mw: weight-averaged molecular weight, Mw/Mn: molecular weight distribution.

Example 40

A desired polymer was obtained in the same manner as in Example 34, except that polypeptone employed in Example 34 was replaced by sodium L-glutamate (Kishida Kagaku) and sebacic acid monomethyl ester, which is one of substrates for polymer synthesis was replaced by suberic acid monomethyl ester.

A structure determination of the obtained polymer carried out by a methanolysis-GC/MS method as in Example 34 confirmed that the polymer was a polyhydroxy alkanoate copolymer constituted of units represented by chemical formulas (86), (80) and (81):

chemical formula (86):

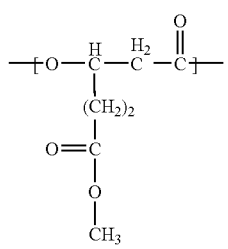
(86)

chemical formula (80):

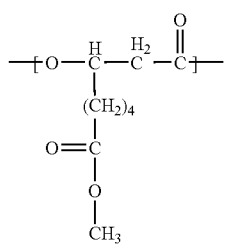
(80)

chemical formula (81):

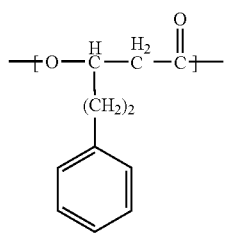
(81)

and the proportions of the units calculated from the ratios of the peak areas of TIC were 8.2%, 84.2% and 8.6% respectively.

The molecular weight of the polymer was measured by gel permeation chromatography as in Example 34.

Table 7 shows weights of the obtained cells and the obtained polymer, a polymer weight ratio per cell, a molecular weight and a molecular weight distribution of the obtained polymer.

TABLE 7

| CDW (mg/L) | PDW (mg/L) | P/C % | Mn (×10$^4$) | Mw (×10$^4$) | Mw/Mn |
|---|---|---|---|---|---|
| 985 | 440 | 44.7 | 7.8 | 14.6 | 1.9 |

CDW: cell dry weight,
PDW: polymer dry weight,
P/C: cell dry weight/polymer dry weight,
Mn: number-averaged molecular weight,
Mw: weight-averaged molecular weight,
Mw/Mn: molecular weight distribution.

The invention claimed is:

1. A polyhydroxy alkanoate copolymer comprising at least a 3-hydroxy-ω-alkenoic acid unit represented by a chemical formula (1) in a molecule, and simultaneously at least a 3-hydroxy-ω-alkanoic acid unit represented by a chemical formula (2) or a 3-hydroxy-ω-cyclohexylalkanoic acid unit represented by a chemical formula (3) in the molecule:

chemical formula (1)

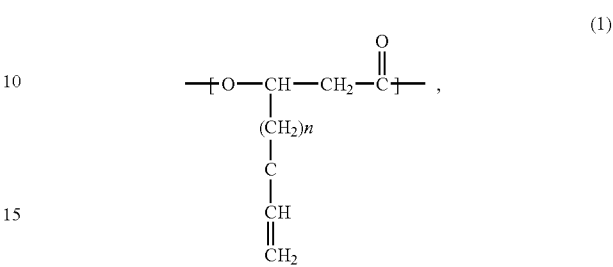
(1)

$n = 1\text{–}8$ in which n represents an integer selected within a range indicated in the chemical formula; and in case plural units are present, n is the same or different for each unit;

chemical formula (2)

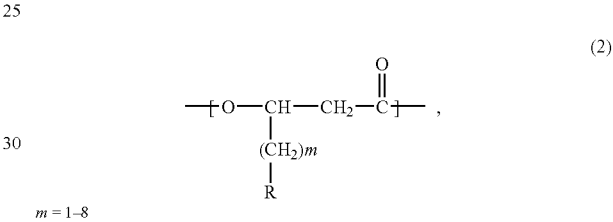
(2)

$m = 1\text{–}8$ in which m represents an integer selected within a range indicated in the chemical formula; R represents a residue having any of a phenyl structure or a thienyl structure; and in case plural units are present, m and R are the same or different for each unit;

chemical formula (3)

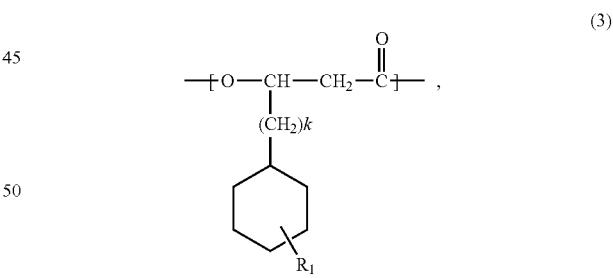
(3)

$k = 0\text{–}8$ in which $R_1$ being a substituent on a cyclohexyl group represents a hydrogen atom, a CN group, a $NO_2$ group, a halogen atom, a $CH_3$ group, a $C_2H_5$ group, a $C_3H_7$ group, a $CF_3$ group, a $C_2F_5$ group, or a $C_3F_7$ group; k represents an integer selected within a range indicated in the chemical formula; and in case plural units are present, $R_1$ and k may be the same or different for each unit, wherein the polyhydroxy alkanoate copolymer is biosynthesized by using a microorganism capable of producing it with at least an ω-alkenoic acid represented by a chemical formula (24) and at least a compound represented by a chemical formula (25) or at least an ω-cyclohexylalkanoic acid represented by a chemical formula (26) as starting materials:
chemical formula (24)

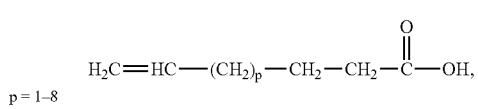

(24)

in which p represents an integer selected within a range indicated in the chemical formula:
chemical formula (25)

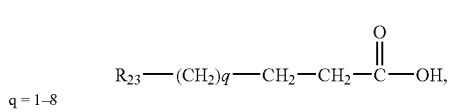

(25)

in which q represents an integer selected within a range indicated in the chemical formula: and $R_{23}$ is a residue having a phenyl structure or a thienyl structure; and
chemical formula (26)

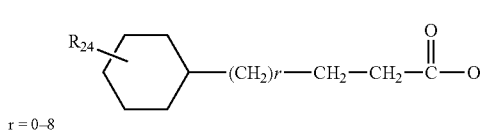

(26)

in which $R_{24}$ is a substituent on a cyclohexyl group and represents an H atom, a CN group, a $NO_2$ group, a halogen atom, a $CH_3$ group, a $C_2H_5$ group, a $C_3H_7$ group, a $CF_3$ group, a $C_2F_5$ group, or a $C_3F_7$ group: and r represents an integer selected within a range indicated in the chemical formula.

2. The polyhydroxy alkanoate copolymer according to claim 1, wherein the residue having a phenyl structure or a thienyl structure of R in the chemical formula (2) and of $R_{23}$ in the chemical formula (25) is selected from the group consisting of chemical formulas (8), (9), (10), (11), (12), (13), (14), (15), (16), (17) and (18):
the chemical formula (8):

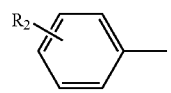

(8)

represents a group of unsubstituted or substituted phenyl groups in which $R_2$ is a substituent on an aromatic ring and represents an H atom, a halogen atom, a CN group, a $NO_2$ group, a $CH_3$ group, a $C_2H_5$ group, a $C_3H_7$ group, a $CH\!=\!CH_2$ group, a $COOR_3$ group ($R_3$ represents an H atom, a Na atom or a K atom), a $CF_3$ group, a $C_2F_5$ group, or a $C_3F_7$ group; and in case plural units are present, $R_2$ is the same or different for each unit;

the chemical formula (9):

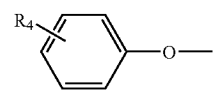

(9)

represents a group of unsubstituted or substituted phenoxy groups in which $R_4$ is a substituent on an aromatic ring and represents an H atom, a halogen atom, a CN group, a $NO_2$ group, a $CH_3$ group, a $C_2H_5$ group, a $C_3H_7$ group, a $SCH_3$ group, a CF3 group, a $C_2F_5$ group, or a $C_3F_7$ group; and in case plural units are present, $R_4$ may be the same or different for each unit;

the chemical formula (10):

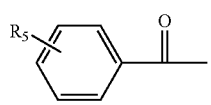

(10)

represents a group of unsubstituted or substituted benzoyl groups in which $R_5$ is a substituent on an aromatic ring and represents an H atom, a halogen atom, a CN group, a $NO_2$ group, a $CH_3$ group, a $C_2H_5$ group, a $C_3H_7$ group, a $CF_3$ group, a $C_2F_5$ group, or a $C_3F7$ group; and in case plural units are present, $R_5$ may be the same or different for each unit;

the chemical formula (11)

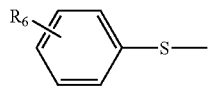

(11)

represents a group of substituted or unsubstituted phenylsulfanyl groups in which $R_6$ is a substituent on an aromatic ring and represents an H atom, a halogen atom, a CN group, a $NO_2$ group, a $COOR_7$ group, a $SO_2R_8$ group ($R_7$ represents either one of H, Na, K, $CH_3$ and $C_2H_5$; and $R_8$ represents either one of OH, ONa, OK, a halogen atom, $OCH_3$ and $OC_2H_5$), a $CH_3$ group, a $C_2H_5$ group, a $C_3H_7$ group, a $(CH_3)_2$—CH group or a $(CH_3)_3$—C group; and in case plural units are present, $R_6$ may be the same or different for each unit;

the chemical formula (12):

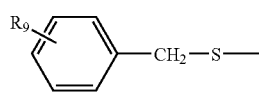

(12)

represents a group of substituted or unsubstituted (phenylmethyl)sulfanyl groups in which $R_9$ is a substituent on an aromatic ring and represents an H atom, a halogen atom, a CN group, a $NO_2$ group, a $COOR_{10}$ group, a $SO_2R_{11}$ group ($R_{10}$ represents either one of H, Na, K, $CH_3$ and $C_2H_5$; and $R_{11}$ represents either one of OH, ONa, OK, a halogen atom, $OCH_3$ and $OC_2H_5$), a $CH_3$ group, a $C_2H_5$ group, a $C_3H_7$ group, a $(CH_3)_2$—CH group or a $(CH_3)_3$—C group; and in case plural units are present, $R_9$ may be the same or different for each unit;

the chemical formula (13):

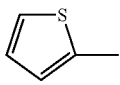
(13)

represents a 2-thienyl group;
the chemical formula (14)

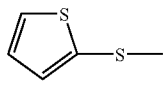
(14)

represents a 2-thienylsulfanyl group;
the chemical formula (15):

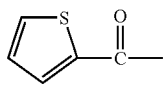
(15)

represents a 2-thienylcarbonyl group;
the chemical formula (16):

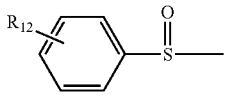
(16)

represents a group of substituted or non-substituted phenylsulfinyl groups in which $R_{12}$ is a substituent on an aromatic ring and represents an H atom, a halogen atom, a CN group, a $NO_2$ group, a $COOR_{13}$ group, a $SO_2R_{14}$ group ($R_{13}$ represents either one of H, Na, K, $CH_3$ and $C_2H_5$; and $R_{14}$ represents either one of OH, ONa, OK, a halogen atom, $OCH_3$ and $OC_2H_5$), a $CH_3$ group, a $C_2H_5$ group, a $C_3H_7$ group, a $(CH_3)_2$—CH group or a $(CH_3)_3$—C group; and in case plural units are present, $R_{12}$ may be the same or different for each unit;
the chemical formula (17):

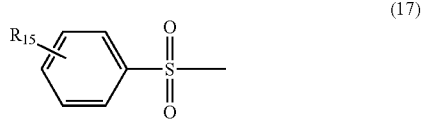
(17)

represents a group of substituted or non-substituted phenylsulfonyl groups in which $R_{15}$ is a substituent on an aromatic ring and represents an H atom, a halogen atom, a CN group, a $NO_2$ group, a $COOR_{16}$ group, a $SO_2R_{17}$ group ($R_{16}$ represents either one of H, Na, K, $CH_3$ and $C_2H_5$; and $R_{17}$ represents either one of OH, ONa, OK, a halogen atom, $OCH_3$ and $OC_2H_5$), a $CH_3$ group, a $C_2H_5$ group, a $C_3H_7$ group, a $(CH_3)_2$—CH group or a $(CH_3)_3$—C group; and in case plural units are present, $R_{15}$ may be the same or different for each unit; and
the chemical formula (18):

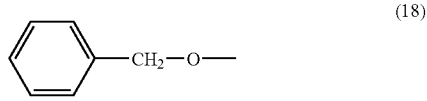
(18)

represents a (phenylmethyl)oxy group.

3. The polyhydroxy alkanoate copolymer according to claim 1, which has a number-averaged molecular weight within a range from 1000 to 1000000.

* * * * *